(12) United States Patent
Dawson et al.

(10) Patent No.: US 7,592,308 B2
(45) Date of Patent: Sep. 22, 2009

(54) F3W VARIANTS OF THE LANTIBIOTIC MERSACIDIN AND ITS USE

(75) Inventors: Michael John Dawson, Hatfield (GB); Jesus Cortes Bargallo, Hatfield (GB); Antony Nicholas Appleyard, Hatfield (GB); Brian Arthur Michael Rudd, Hatfield (GB); Steven Boakes, Hatfield (GB); Gabriele Bierbaum, Bonn (DE); Anja Hoffmann, Bonn (DE); Stephanie Schmitz, Bonn (DE)

(73) Assignee: Novacta Biosystems Limited, Welwyn Garden City (GB)

( * ) Notice: Subject to any disclaimer, the term of this patent is extended or adjusted under 35 U.S.C. 154(b) by 0 days.

(21) Appl. No.: 11/526,225

(22) Filed: Sep. 25, 2006

(65) Prior Publication Data

US 2007/0117749 A1    May 24, 2007

Related U.S. Application Data

(63) Continuation-in-part of application No. PCT/GB2005/001055, filed on Mar. 21, 2005.

(60) Provisional application No. 60/720,464, filed on Sep. 27, 2005.

(30) Foreign Application Priority Data

Mar. 26, 2004    (GB) ................. 0406870.6

(51) Int. Cl.
  *A61K 38/00*    (2006.01)
(52) U.S. Cl. .......................... 514/9; 530/317
(58) Field of Classification Search ........ None
See application file for complete search history.

(56) References Cited

U.S. PATENT DOCUMENTS 5,667,991 A    9/1997    Koller et al.

FOREIGN PATENT DOCUMENTS

| EP | 0 700 998 A1 | 3/1996 |
|---|---|---|
| WO | WO 03/099862 | 12/2003 |
| WO | WO 2005/093069 | 10/2005 |

OTHER PUBLICATIONS

Cotter et al (Current Protein and Peptide Science, 6:61-75, Feb. 2005).*
Szekat et al, "Construction of an Expression System for Site-Directed Mutagenesis of the Lantibiotic Mersacidin", Applied and Environmental Microbiology, Jul. 2003, vol. 69, No. 7, pp. 3777-3783.
International Search Report dated Mar. 6, 2007, issued in connection with PCT/GB2006/003570.
Britton et al, "Genome-Wide Analysis of the Stationary-Phase Sigma Factor (Sigma-H) Regulon of *Bacillus subtilis*", Journal of Bacteriology, Sep. 2002, vol. 184, No. 17, pp. 4881-4890.
Altena et al, "Biosynthesis of the Lantibiotic Mersacidin: Organization of a Type B Lantibiotic Gene Cluster", Applied and Environmental Microbiology, Jun. 2000, vol. 66, No. 6, pp. 2565-2571.
Guber et al, "Role of the Single Regulator MrsR1 and the Two-Component System MrsR2/K2 in the Regulation of Mersacidin Production and Immunity", Applied and Environmental Microbiology, Jan. 2002, vol. 68, No. 1, pp. 106-113.

* cited by examiner

*Primary Examiner*—Patricia A Duffy
(74) *Attorney, Agent, or Firm*—Nixon & Vanderhye P.C.

(57) ABSTRACT

The present invention relates to methods and products for improved production of the lantibiotic mersacidin. There is provided a method of producing a mersacidin variant which comprises introducing into a cell which is a ΔMrsA host cell an expression vector encoding said variant, and recovering said variant from the cell culture. Preferred variants include the novel variants of Table 1, e.g. mersacidin F3W, said mersacidin F3W optionally having a further one or more variations, e.g. mersacidin F3W G8A. Also provided is a *Bacillus* cell which is a SigH deficient strain of *Bacillus* sp. HIL Y-85,54728 (NCIMB Accession Number NCIMB 41211); this cell may also be used in the production of mersacidin and its variants. Further aspects of the invention include a DNA cassette which comprises a nucleotide sequence encoding the mersacidin mrsA propeptide, and a method to transform a *Bacillus* HIL host cell with plasmid, which method includes the step of electroporation.

12 Claims, 10 Drawing Sheets

```
  M   S   Q   E   A   I   I   R   S   W   K   D   P   F   S   R   E   N   S   T   Q   N
 atg agt caa gaa gct atc att cgt tca tgg aaa gat cct ttt tcc cgt gaa aat tct aca caa aat
                             aga tct         g gat cc   c tcg aga
                              BglII           BamHI       XhoI
                             cga tcg                    tcg cga
                              PvuI                       NruI
                                                        tct aga
                                                         XbaI
                                                        cc cgg g
                                                         Xma I
                                                                         g aat tc
                                                                          EcoRI P   A   G   N   P   F   S   E   L   K   E   A   Q   M   D   K   L   V   G   A   G   D
 cca gct ggt aac cca ttc agt gag ctg aaa gaa gca caa atg gat aag tta gta ggt gcg gga gac
 ca gct g                   gag ctc                         aag ctt         ggc gcc
  PvuII                      SacI                            HindIII         NarI
 cc gcg g                                                           a cta gt    gcc ggc
  SacII                                                              SpeI       NaeI
 cg gcc g
  EagI M   E   A   A   C   T   F   T   L   P   G   G   G   V   C   T   L   T   S   E   C
 atg gaa gca gca tgt act ttt aca ttg cct ggt ggc ggt gtt tgt act cta act tct gaa tgt
             gca tgc                     ctc ccg gg          tgt aca        act agt     c
              SphI                         XmaI               BsrGI          SpeI
            g tgc ac                      ccc ggg                    g tta ac
              ApaLI                        XmaI                       HpaI I   C   *
 att tgt taa
 ata tg  aag ctt
  NdeI    HindIII
```

Figure 9

F3W VARIANTS OF THE LANTIBIOTIC MERSACIDIN AND ITS USE

REFERENCE TO EARLIER APPLICATIONS

This application claims the benefit of priority of U.S. 60/720,464 filed Sep. 27, 2005 (pending), and is a continuation-in part of PCT/GB2005/001055 filed Mar. 21, 2005 (pending) designating the US and claiming priority from GB 0406870.6 filed Mar. 26, 2004. The disclosures of U.S. 60/720,464, PCT/GB2005/001055 and GB 0406870.6 are incorporated herein by reference in their entirety.

FIELD OF THE INVENTION

The present invention relates to a bacterial cell, particularly of the genus *Bacillus*, which has improved properties for the production of an antibiotic. The invention further relates to novel variants of the lantibiotic, mersacidin.

BACKGROUND TO THE INVENTION

Mersacidin belongs to a group of bactericidal peptides that are called lantibiotics. The name signifies that these peptides contain the amino acids lanthionine and/or 3-methyllanthionine. Mersacidin has activity against methicillin-resistant *Staphylococcus aureus* (MRSA) and is therefore of considerable interest in medicine.

Mersacidin is produced by a specific species of the genus *Bacillus*, which has been designated HIL Y-85,54728 ("HIL"). The cloning of the mersacidin gene is disclosed by Bierbaum et al, 1995.

Mersacidin is produced by processing of a small protein of 68 amino acids. The N-terminal 48 amino acids of the protein form a leader sequence, and the C-terminal 20 amino acids are a propeptide sequence which is processed by modifying enzymes to produce mersacidin. The sequence of the mersacidin gene, mrsA, is provided as SEQ ID NO:1 and its translation as SEQ ID NO:2.

The mrsA gene forms part of the mrs gene cluster of about 12.3 kb (Altena et al, 2000). The gene cluster includes regulatory genes which control the production of mersacidin by regulating the expression of the mrsA gene and/or its modifying enzymes. The mrsA gene is expressed in early stationary phase of the growth of the *Bacillus* HIL strain.

A problem with the use of *Bacillus* HIL as a host cell for the production of products of interest is the fact that under certain conditions the host cell sporulates. For larger scale production presence of spores potentially causes significant handling difficulties especially if the producer strain is a GMO, as is likely to be the case for a producer of a variant mersacidin. In case of a spillage, *bacillus* spores are difficult to kill with most disinfecting chemicals. Removal of spores in process streams would be difficult without expensive microfiltration. A sporulating GMO is therefore likely to require a higher cost and complexity of engineering for containment and processing.

At a research level, the presence of spores can make the development of alternative lantibiotics based upon engineering of the wild-type gene cluster difficult. For example, overlay assays for anti-bacterial activity can be spoiled by outgrowth of spores.

A further problem generally with the *Bacillus* HIL strain is that it—in common with many other *Bacillus* strains—produces other products with anti-bacterial activity. These products can interfere with the development of assays designed to investigate the properties of variant *Bacillus* HIL strains.

Sigma H is the product of the sigH (or spo0H) gene. It is essential for transcription of genes that function in the transition from exponential to stationary phase and in the induction of sporulation. Mutants deficient in SigH do not sporulate. SigmaH activates transcription of a number of other regulatory proteins e.g. spo0A, spo0F, kinA, spo0M, spoVG, spoVS and the spoIIA family as well as the phr family of secreted peptide pheromones. For further details see Britton et al. J Bacteriol. 184, 4881-90; 2002.

Directly or indirectly Sigma H influences transcription of about 10% of all genes of *Bacillus* (Britton et al., 2002). Early results showed that sigma H is involved in the biosynthesis of gramicidin S (Marahiel et al. Mol. Microbiol. 7, 631-636; 1993), and Britton et al. found that the following antibiotic production genes are downregulated in a sigH deficient mutant: cotN (tasA, antimicrobial spore component), pksC-DEFGHIKLMNR (polyketide synthesis), pnbA (paranitrobenzyl esterase), srfAB (surfactin synthetase), ywhP (albD) and ywiA (albA, both involved in antilisterial bacteriocin production), thus knockout affects multiple antibiotic biosynthesis pathways.

Szekat et al. (2003) Appl. Env. Microbiol. 69, 3777-3783 describe the construction of an expression system for generation of variant mersacidins. Modified mrsA genes are generated by site-directed mutagenesis using a commercial phagemid system. The modified genes are then excised and ligated into a temperature sensitive plasmid which replicates in Gram-positive bacteria such as *Bacillus* sp. The plasmids are introduced into *Staphylococcus carnosus* by protoplast transformation and then introduced into the mersacidin-producing *bacillus* again by protoplast transformation. The bacilli are then grown at elevated temperature so that the plasmid cannot replicate autonomously and thus integrates into the chromosome by homologous recombination in the mrsA region. At this stage the *bacillus* now contains the entire expression plasmid inserted into the mersacidin biosynthetic pathway and hence has two copies of the mrsA gene, one of which is mutated and the other wild-type.

These constructs do not produce either mersacidin or the engineered variant presumably due to disruption of other elements of the biosynthetic pathway. The next stage is to grow these constructs for a large number of generations without selection for the plasmid in order to allow a second recombination event to occur to excise the plasmid and to leave a single copy of the mrsA gene. Depending on where the recombination events occur this can either reconstruct the wild-type mrsA gene or generate the engineered variant and clones need to be screened to identify one in which the desired event has occurred. The net result is a direct replacement of the wild-type mrsA gene by a mutant gene in the chromosome. This procedure is lengthy and relatively inefficient for the production of large numbers of variants of mersacidin.

Three variants of mersacidin were produced by Szekat et al. (ibid); F3L, S16I and E17A (where the numbers refer to the numbering of the mature mersacidin peptide sequence and the letters are the 1-letter amino acid code).

Of these three variants, both the S16I and E17A were essentially inactive (about 1,000-fold greater Minimum Inhibitory Concentration (MIC) measured against *M. luteus*) while the F3L peptide was weakly active (MIC of 12.5 mg/l against *M. luteus*, compared to wild-type of 0.195). The data of Szekat et al thus suggest that mersacidin is very sensitive to alterations and variation of the primary sequence is likely to be deleterious.

Another problem associated with the production of mersacidin variants is that the *Bacillus* HIL has only been transformable at low frequencies using protoplast transformation.

In order to investigate large numbers of mersacidin derivatives, a more efficient transformation system is required.

Variants of naturally occurring antibiotics can be useful in medicine. Variants can be produced synthetically, semi-synthetically (e.g. by chemical modification of fermented products) or by genetic changes to the organisms which produce them. Potentially, mersacidin could be varied by all three routes, with the latter two being of particular interest. For example, modification of amino acids could be used to produce variants which have altered activity profiles, as well as properties such as bioavailability, biodistribution or the ability to overcome resistance mechanisms to mersacidin itself. Altered amino acids may also be useful to introduce reactive side-chains allowing modification of the peptide by chemical means.

DISCLOSURE OF THE INVENTION

The present inventors have produced a version of the HIL strain in which the SigH gene has been inactivated. Surprisingly, it has been found that the production of mersacidin is not affected by this change. In the SigH negative derivative mersacidin production was unaffected though both sporulation and production of an antibacterial substance or substances other than mersacidin were both suppressed.

The features of the novel strain thus provide a useful attribute for development of a system for generation and screening of variants of mersacidin. The lack of sporulation and of secreted antibiotics other than mersacidin will also be of benefit for larger-scale production of mersacidin and related lantibiotics expressed from the mrs gene cluster.

Accordingly, the present invention provides a *Bacillus* which is a SigH deficient strain of the *Bacillus* sp. HIL Y-85, 54728 (NCIMB Accession Number NCIMB 41211, deposited 19th Mar. 2004). The strain of the invention is referred to herein as "ΔSigH HIL".

The invention further provides a method of producing a lantibiotic which comprises culturing the bacterial strain of the invention in a culture medium and recovering the lantibiotic from the medium. The lantibiotic may be mersacidin or a derivative thereof.

In another aspect, the invention provides a method of making a ΔSigH HIL, which method comprises introducing into a *Bacillus* HIL a recombinant DNA construct containing a SigH mutant gene, and integrating said mutant gene at the SigH locus in the genome of the cell.

In another aspect, the inventors have developed a vector system useful for producing and screening lantibiotic derivatives of MrsA. This has been achieved by introducing one or more restriction endonuclease recognition sites into the mrsA gene in order to produce an expression cassette system. Thus in another aspect, the invention provides a recombinant DNA cassette which comprises a nucleotide sequence encoding the mersacidin mrsA propeptide, wherein said sequence comprises a first restriction site at or adjacent the N-terminal encoding region of the encoding sequence;
optionally a second restriction site downstream of the first restriction site and within the encoding sequence; and
a third restriction site at or adjacent the C-terminal encoding region of the encoding sequence,
wherein at least one of said restriction sites does not occur within the mrsA sequence shown as SEQ ID NO:1.

Generally, all two or three sites will be different from each other. It is also desirable that when the cassette is carried by a vector, the sites are unique for that vector.

In a preferred aspect, the non-naturally occurring restriction enzyme site is the second restriction site and is located between codons 8 and 16 of the encoding sequence.

The cassette will desirably also include the mrsA leader sequence and mrsA promoter, and may include in addition or alternatively a mrsR1 gene.

The cassette of the invention described above may be engineered in a variety of ways. For example, the fragment obtained by cleaving the cassette between the first and second, first and third, or second and third, restriction sites may be replaced with a variant coding sequence encoding a mersacidin derivative. Thus the invention provides a variant of the cassette of the invention wherein said variant has from 1 to 15 nucleotide substitutions within the encoding region of the encoding sequence.

As an intermediate to the production of such a variant, the sequence of between the first and second, first and third, or second and third, restriction sites may be replaced by a larger stuffer fragment.

In another aspect, the cassette encoding a mersacidin derivative may be used to transform a *Bacillus* HIL host cell to express the mersacidin derivative, for example to assess its anti-bacterial properties.

In one aspect, a multiplicity of expression cassettes may be made to provide a library of different mersacidin derivatives, which may then be screened for activity.

The cassettes may be transformed into the HIL *Bacillus* or the SigH deficient HIL of the present invention. An alternative expression host is the HIL *Bacillus* which comprises a mrsA mutation such that the MrsA gene product is either inactive or not produced. Such a *Bacillus* is referred to herein a "ΔMrsA HIL". Optionally, this *Bacillus* may be deficient in SigH. This is referred to herein as a "ΔMrsA ΔSigH HIL".

In another aspect, the invention provides a ΔMrsA HIL cell, wherein the cell further comprises a construct encoding a mersacidin derivative operably linked to a promoter such as a mrsA promoter. The construct may be on an autonomously replicating vector, or integrated into the genome of the host cell at a site outside the mrs gene cluster. The construct may additionally comprise the mrsR1 gene.

The mersacidin derivative may be encoded by an expression cassette of the invention.

The invention also provides a method of making a mersacidin derivative which method comprises introducing into a ΔMrsA HIL host cell a construct encoding said mersacidin derivative operably linked to a promoter such as a mrsA promoter and culturing said host cell or progeny thereof in a culture medium and recovering the mersacidin derivative from the medium. The construct may additionally comprise the mrsR1 gene.

The invention thus further comprises a method of making a mersacidin derivative which method comprises culturing a ΔMrsA HIL host cell which contains a construct encoding said mersacidin derivative operably linked to a promoter such as a mrsA promoter in a culture medium and recovering the mersacidin derivative from the medium.

In another aspect, the invention provides method of producing a mersacidin derivative-producing strain of HIL, said method comprising:
transforming a ΔMrsA HIL with a vector comprising said mersacidin derivative coding region which is operably linked to a mrsA promoter, said coding region joined to a downstream mrsR1 gene, wherein said vector further comprises a selectable marker;
culturing said ΔMrsA HIL under conditions for integration of said vector into said target region;

selecting a transfomant in which the mersacidin derivative coding region has been integrated into the target region operably linked to the mrsA promoter.

The ΔMrsA HIL may also be a ΔMrsA ΔSigH HIL. Alternatively the cell may be a host cell comprising the mrs gene cluster in which the mrsA gene has been inactivated, wherein the host cell is optionally also a ΔSigH host cell.

In a further aspect, the present inventors have improved the methods for transformation of the *Bacillus* HIL strain. Prior to the present invention, protoplast transformation has been used to introduce plasmid DNA into this strain. It has now been found that under appropriate conditions, it is possible to transform *Bacillus* HIL by electroporation. Accordingly the invention provides a method to transform a *Bacillus* HIL, including the ΔSigH and/or ΔMrsA derivatives, which method includes the step of electroporation.

We have identified a number of mersacidin variants which have activity against a range of bacteria, including two strains of methicillin resistant *S. aureus* (MRSA). Thus unlike the variants described by Szekat et al, the variants of the present invention have anti-bacterial activity which in many cases is of a comparable or even better level than that of mersacidin itself. The invention in another aspect thus provides novel antibiotic compounds, genes encoding such compounds, methods of making such compounds and their use in the treatment of human or animal subjects, particularly in conditions requiring anti-bacterial therapy. These and other aspects of the invention are described herein below.

DESCRIPTION OF THE DRAWINGS

FIG. 9 shows potential restriction sites in the mrsA gene (SEQ ID NO:1) which can be generated by silent nucleotide changes. The translation of gene sequence (SEQ ID NO:2) is also shown.

DETAILED DESCRIPTION OF THE INVENTION

Production of ΔSigH HIL

Figure 1:
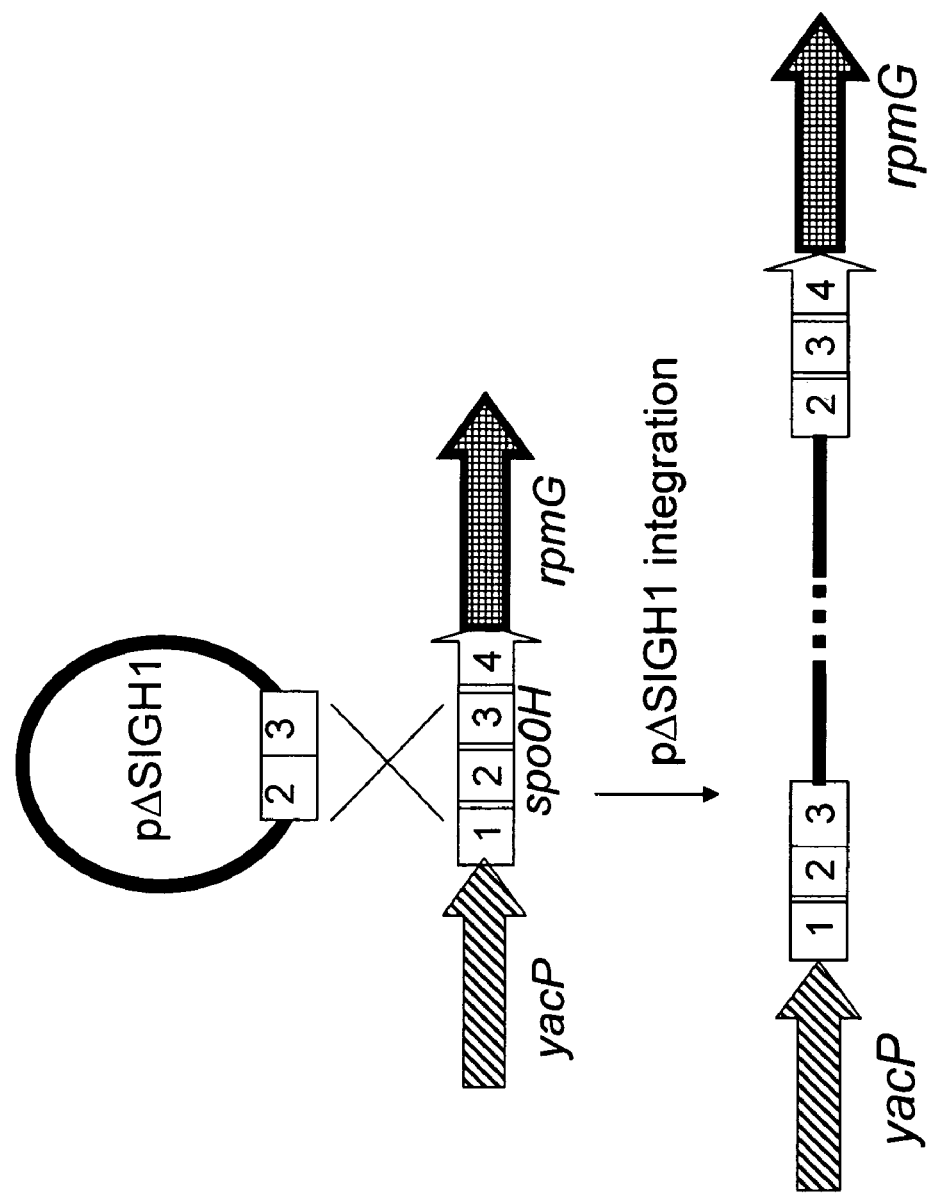
FIG. 1 shows the strategy used by the inventors to inactivate the SigH gene in the HIL strain, by integration of pΔSIGH1 into the chromosome of *Bacillus sp.* HIL Y-85, 54728 TT.

ΔSigH HIL strains of the invention may be made utilising the HIL strain deposited as NCIMB Accession Number NCIMB 41211, deposited 19th Mar. 2004. In order to make the ΔSigH derivative, the SigH gene in the HIL strain may be inactivated in accordance with standard techniques available in the art.

Typically the ΔSigH *Bacillus* can be made using targeted homologous recombination. This is a method well known in the art and there are a variety of strategies which may be used. In its simplest form, a construct such as a plasmid which contains part of a *Bacillus* SigH coding sequence is introduced into the HIL strain, e.g. by protoplast transformation. The vector contains a selectable marker such as a chloramphenicol acetyl transferase gene, and the transformed cells are selected for integration of the marker into the chromosome.

The approach described above relies on a single recombination event with an integrative vector. For this approach it is necessary for the incoming SigH gene to be defective at both ends otherwise one intact gene would be recreated.

An alternative approach is to carry out a double homologous recombination (gene replacement). With this approach only a single defect is needed. When the second recombination event occurs it can either restore the wild-type sigH or generate the mutant.

Thus, in the accompanying Example 1, a SigH gene, truncated at both the N- and C-terminal coding regions was used as the integrant. When this sequence was integrated by homologous recombination it produced a genome with two tandem partial SigH genes, neither of which produce a fully functional gene product. However it will be understood that the precise means by which the SigH gene is inactivated is not a limiting feature of the present invention. Strategies such as double homologous recombination outlined above, which can be used to delete the gene, or substantial portions thereof, from the chromosome altogether, or which inactivate promoter regions of the SigH gene may also be used. A double homologous recombination event to produce a SigH mutant with an internal deletion is illustrated in Example 2.

The SigH coding sequence is widely available in the art, and is also available in databases, such as GenBank, accession no. NC_000964.

In an alternative embodiment, the invention provides a host cell which comprises the mrs gene cluster (this cluster is described in Altena et al, 2000), wherein the host cell is a ΔSigH host cell. This host cell may be used in the practice of all aspects of the present invention described herein for ΔSigH HIL. The mrs gene cluster may be one in which the mrsA gene is inactivated or produces an inactive gene product. Such a host cell may be a low GC Gram-positive bacterium, for example any strain of *Bacillus*, such as *B. subtilis*. The laboratory strain *B. subtilis* 168 may be used.

ΔMrsA HIL Strains

In another aspect, the ΔSigH HIL may also be an HIL derivative in which the mrsA gene product is inactive, either because the mrsA gene is transcriptionally inactive, or because the gene product is a mutant which does not show antibacterial activity against bacteria which are normally killed by mersacidin. Such bacteria include *Micrococcus luteus*, such as *M. luteus* ATCC 4498.

A ΔMrsA HIL in which the mrsA gene is inactivated by insertion into the mrsA gene of an erythromycin resistance gene is disclosed in Altena et al, 2000. Another ΔMrsA HIL is the E17A HIL disclosed by Szekat et al, 2003. A further ΔMrsA HIL is one in which the mrsA gene is altered to include a stop codon resulting in a truncated and inactive gene product. One such example of this is the ΔMrsA HIL pAE4stop as set out in Example 6.

All these and other ΔMrsA HIL strains may be used to produce ΔMrsA ΔSigH HIL strains of the invention.

In addition, the ΔMrsA HIL strains may be used without the ΔSigH feature in the practice of the other aspects of the invention described herein.

Transfer of the mrs Gene Cluster into a Host Cell

A restriction map of the mrs gene cluster is shown in Altena et al, 2000. The sequence of this cluster is available as GenBank accession number: AJ250862. Using the deposited HIL strain as a source of DNA, the overlapping restriction fragments illustrated in Altena et al may be obtained by, for example, PCR amplification based on primers derived from AJ250862. These fragments are assembled using standard cloning procedures and the mrs gene cluster cloned into a suitable cloning vector. Such a vector may be pTRKH2 (O'Sullivan and Klaenhammer 1993).

The vector may be transformed into a laboratory strain of *B. subtilis* such as *B. subtilis* 168 in order to replicate, and plasmid DNA isolated from this host. The plasmid may be integrated into this host, or recovered and introduced into other host cells, particularly low-GC Gram positive host cells. These include *Bacillus* species, particularly *B. subtilis*, as well as for example *S. carnosus*.

Accordingly the present invention provides a bacterial host cell which carries a vector comprising the mrs gene cluster. The invention also provides a bacterial host cell in which the mrs gene cluster has been integrated into the genome, wherein said cell is not the HIL strain.

The bacterial host cell may be a ΔSigH, a ΔMrsA, or a ΔMrsA ΔSigH host cell.

Preferably the host cell is a *Bacillus* host cell, such as a *B. subtilis* host cell.

Expression Cassettes

An expression cassette of the invention may be based on any cloning and expression vector used in the art for the expression of genes in host cells. Such vectors will include one or more origins of replication, which may be temperature sensitive. The vectors may include a selectable marker, such as the chloramphenicol acetyl transferase gene, the erythromycin resistance gene or the tetracycline resistance gene. The vector may also contain a targeting region, this region being homologous to a genomic sequence present in the host cell outside the mrs gene cluster. Such a vector may be used to integrate the cassette into the genomic sequence homologous to the targeting region.

The expression cassette may also comprise a mrsR1 gene downstream of the mrsA gene or derivative thereof. Where the host cell is a ΔMrsA host cell in which the mrsA gene has been inactivated in a manner which also inactivates the mrsR1 gene (e.g. in the strain disclosed in Altena et al, 2000), the expression cassette may further comprise a mrsR1 gene.

As used herein, by "at or adjacent the N-terminal encoding region" it is meant that the first base of the restriction site is located at a position from six residues upstream of the ATG codon of the mrsA leader sequence to no more than six codons downstream of the first codon of the propeptide (TGT, encoding cysteine). Preferably the first base of the restriction site is located at a position from twelve, preferably six, residues upstream to six residues downstream of the first codon of the propeptide encoding sequence.

In one aspect, the first restriction site is an SphI site. FIG. 9 sets out other restriction sites which may be introduced within the leader sequence upstream of the SphI site, as well as an ApaLI site which may be made two nucleotides downstream of the SphI site.

Similarly, by "at or adjacent the C-terminal encoding region" it is meant that the first base of the restriction site either includes at least one of the nucleotides of the TAA termination codon of the propeptide or the 5' or 3' nucleotide of the restriction site is no more than twelve, preferably six, residues downstream or upstream respectively of the TAA codon.

In one aspect, the third restriction site is a HindIII site.

The second restriction site, when present, will lie between the first and third restriction sites. Preferably the restriction site includes at least one nucleotide present from codon 5 to codon 16, preferably codon 8 to 16 of the propeptide-encoding sequence. In the accompanying examples, a BsrG1 site has been introduced by altering codon 13 of the MrsA-encoding sequence. In combination with codon 12, this results in the site having the sequence 5'-TGTACA-3'. However, other changes are also contemplated by the present invention. FIG. 9 sets out other possible non-coding changes which may be made, and the restriction sites which can be created as a result. Thus the second restriction site, when present, may also be an XmaI site spanning the propeptide codons 5-7; an XmaI site at codons 6-7; a HpaI site spanning codons 13-15 or a SpeI site at codons 15-16.

It is also possible to introduce more than one of these changes such that the expression cassette includes two or more sites between the first and third restriction sites.

The cassette may include two or three non-naturally occurring restriction sites. In the accompanying example, all three sites do not normally occur in the MrsA sequence of SEQ ID NO:1.

The expression cassette simplifies the rapid production of lantibiotics which are mersacidin derivatives, as discussed further herein below.

In one aspect, the region between the first and second sites, the first and third, or the second and third sites, may be replaced by a stuffer fragment. Where two or more sites between the first and third sites are present, the region between any pair of such sites may also be replaced by a stuffer fragment. A stuffer fragment is a piece of DNA which is larger than the sequence which it replaces. The stuffer fragment may be from 50 to 5000 nucleotides in size, for example from about 500 to 2000 nucleotides in size. The value of introducing these stuffer DNA fragments is that when the region is replaced by a lantibiotic-encoding oligonucleotide there is a significant decrease in plasmid size. The resulting plasmid can thus be readily purified away from any minor population of unrestricted plasmid thus eliminating any background.

A cassette of the invention may be used to introduce specific changes to the MrsA sequence in a vector which can then be introduced into a host cell for expression of a lantibiotic. To achieve this, the sequence is desirably operably linked to the MrsA leader sequence, which in turn is operably linked to the MrsA promoter.

In addition or as an alternative, the vector comprising the cassette may also include a mrsR1 gene. The mrsR1 gene will be located downstream of, and in tandem with, the mersacidin (or derivative thereof) coding sequence.

Expression Libraries

Expression cassettes of the invention may be used to provide libraries of lantibiotic-encoding genes. Such libraries may be made by introducing into the cassette, between the first and second restriction sites, the first and third restriction sites, or the second and third restriction sites, a multiplicity of sequences each of which corresponds to the corresponding mrsA sequence apart from having from 1 to 15, for example from 1 to 10, preferably from 1 to 6, for example from 1 to 3 nucleotide changes compared to the propeptide portion of SEQ ID NO:2. Preferably such changes result in a change of the protein encoded by the sequence. However non-coding changes are not excluded.

Libraries form a further aspect of the invention. Such libraries may comprise from 10 to 100,000, such as from 10 to 10,000 for example from 10 to 1,000 different coding sequences which are variants of the mersacidin coding sequence as defined in the preceding paragraph.

An expression cassette encoding a lantibiotic derivative may be introduced into a HIL cell for expression of the lantibiotic.

In one embodiment, the library may be transformed into a Bacillus HIL or derivative thereof such as a ΔSigH HIL, a ΔMrsA HIL or a ΔMrsA ΔSigH HIL, colonies isolated and screened for antibacterial activity.

The sequences of the mersacidin variant expressed by individual colonies showing such activity can be determined.

In another embodiment, an expression library of the invention may be transformed into a host cell which comprises the mrs gene cluster, optionally wherein the cell is a ΔSigH host cell, and alternatively or in addition wherein the cell is a ΔMrsA host cell.

Production of Mersacidin

ΔSigH cells of the invention may be used to produce mersacidin. In order to do this, cells are cultured in a suitable culture medium (e.g. Bierbaum et al; 1995), and the mersacidin recovered from the culture medium, e.g. according to the methods of Szekat et al (2003).

Similarly, ΔMrsA ΔSigH HIL cells of the invention which carry an expression vector capable of expressing MrsA may be used in the production of mersacidin.

Production of Mersacidin Derivatives

The ΔSigH HIL obtained in the accompanying example produces mersacidin. Szekat et al. describe the construction of an expression system for site-directed mutagenesis of mersacidin. Similar expression systems may be used in the ΔSigH HIL host cell (or ΔSigH host cell comprising the mrs gene cluster)of the present invention in order to obtain a cell which expresses a non-wild-type lantibiotic which is a mersacidin derivative.

The ΔSigH HIL host cell (or ΔSigH host cell comprising the mrs gene cluster) may also be a ΔMrsA cell.

It will be apparent that in producing such cells, the SigH gene may be inactivated either before or after an altered mrsA gene encoding the mersacidin derivative has been introduced into the cell. In either order, the resulting product will be a ΔSigH host cell, such as the HIL Bacillus, of the present invention.

Mersacidin derivatives may be expressed by an expression vector. Such vectors may include an origin of replication, which may be temperature sensitive. The vectors may include a selectable marker, such as the chloramphenicol acetyl transferase gene, the erythromycin resistance gene or the tetracycline resistance gene.

In one embodiment, an altered mrsA gene may be introduced by targeted homologous recombination, according to the method of Szekat et al, 2003. The targeted homologous recombination may be performed as a single homologous recombination, as described herein below, or as a double homologous recombination so as to replace the mrsA gene present in the cell.

The mrsA gene present in the cell may be wild-type or may encode a mersacidin derivative, such as the E17A derivative. The advantage of targeting the E17A derivative (or other derivatives with similar properties) is that this peptide does not have anti-bacterial activity. Thus supplementing this gene with single homologous recombination or replacing it by double homologous recombination with a mersacidin derivative having anti-bacterial activity allows for convenient screening of the resulting cells. Specific mersacidin derivatives with reduced activity include in addition to the E17A, the F3L and S16I derivatives described in Szekat et al. Strains producing these derivatives may be used to generate a ΔSigH HIL of the invention in which the activity of further mrsA variants may be examined against a background of an inactive variant.

Preferred mersacidin derivatives which may be produced include mersacidin compounds which correspond to the amino acid sequence of the mersacidin propeptide set out as SEQ ID NO:2 apart from one or more, for example from 1 to 6, e.g. from 1 to 3 amino acid alterations. Alterations include substitutions, deletions and insertions.

The mersacidin derivatives may be lantibiotics expressed by members of an expression library of the invention, as described herein above. The invention thus provides a mersacidin derivative obtained by methods of the invention for use in therapy, for example in the treatment of MRSA.

Mersacidin Variants

One mersacidin derivative of the invention is mersacidin F3W. Another is mersacidin G8A. Another is mersacidin F3W G8A. These mersacidin derivatives and their use in therapy form a further aspect of the invention.

In one aspect, the invention provides a mersacidin variant wherein the variant comprises a modification to position 3, 5, 6, 7, 8, 9, 10, 11, 14 or 16 of mersacidin as set out in Table 1 below:

TABLE 1

| F3  | L5  | P6  | G7  | G8  | G9  | G10    | V11 | L14  | Dha16    |
|-----|-----|-----|-----|-----|-----|--------|-----|------|----------|
| F3W | L5A | P6H | G7A | G8A | G9A | G10A   | V11L| L14V | Dha16G   |
| F3R | L5I | P6A | G7N | G8C | G9S | G10V   | V11I| L14I | Dha16A   |
| F3D | L5M | P6N | G7Q | G8N | G9T | G10S   | V11M| L14M | Dha16Dhb |
| F3I | L5N | P6Q | G7W | G8Q | G9N | G10Dha | V11K|      | Dha16H   |
| F3P | L5H | P6V | G7S | G8H | G9R | G10M   | V11C|      |          |
| F3S |     | P6M | G7T | G8E | G9Y | G10Y   |     |      |          |
| F3C |     | P6F | G7M | G8I | G9H | G10W   |     |      |          |
| F3M |     | P6Y | G7I | G8S | G9Q | G10I   |     |      |          |
| F3N |     | P6G | G7H | G8P | G9L | G10Dhb |     |      |          |

TABLE 1-continued

| F3  | L5 | P6  | G7  | G8 | G9 | G10  | V11 | L14 | Dha16 |
|-----|----|-----|-----|----|----|------|-----|-----|-------|
| F3H |    | P6L | G7F |    |    | G10R |     |     |       |
|     |    | P6I |     |    |    | G10K |     |     |       |
|     |    | P6D |     |    |    | G10H |     |     |       |
|     |    | P6E |     |    |    | G10N |     |     |       |

Where Dha is dehydroalanine and Dhb is dehydrobutyrine. When these modified amino acid residues are present, this is due to post-translational modification of serine and threonine residues respectively, brought about by the expression of other genes of the mrsA gene cluster.

In a preferred aspect, the variant comprises a modification to position 3, 6, 7, 8, 9, 10, 11, 14 or 16 of mersacidin as set out in Table 2 below:

TABLE 2

| F3  | P6  | G7  | G8  | G9  | G10    | V11  | L14  | Dha16    |
|-----|-----|-----|-----|-----|--------|------|------|----------|
| F3W | P6H | G7A | G8A | G9A | G10A   | V11L | L14V | Dha16G   |
| F3R | P6A | G7N | G8C | G9T | G10V   | V11I | L14I | Dha16A   |
| F3D | P6N | G7Q | G8N | G9R | G10S   | V11M | L14M | Dha16Dhb |
|     | P6Q | G7W | G8Q | G9H | G10Dha | V11K |      | Dha16H   |
|     | P6V | G7T | G8H |     | G10M   | V11C |      |          |
|     | P6M | G7M |     |     | G10Y   |      |      |          |
|     | P6Y |     |     |     | G10W   |      |      |          |

In a more preferred aspect, the variant comprises a modification to position 3, 6, 7, 8, 9, 10, 11, 14 or 16 of mersacidin as set out in Table 3 below:

TABLE 3

| F3  | P6  | G7  | G8  | G9  | G10    | V11  | L14  | Dha16    |
|-----|-----|-----|-----|-----|--------|------|------|----------|
| F3W | P6H | G7A | G8A | G9A | G10A   | V11L | L14V | Dha16G   |
| F3D | P6A | G7N | G8N | G9T | G10V   | V11I | L14I | Dha16A   |
|     | P6N | G7Q | G8Q | G9R | G10S   | V11M | L14M | Dha16Dhb |
|     |     | G7T | G8H | G9H | G10Dha | V11K |      | Dha16H   |
|     |     | G7M |     |     | G10M   |      |      |          |
|     |     |     |     |     | G10Y   |      |      |          |

In an even more preferred aspect, the variant comprises a modification to position 3, 7, 8, 9, 10, 11, 14 or 16 of mersacidin as set out in Table 4 below:

TABLE 4

| F3  | G7  | G8  | G9  | G10  | V11  | L14  | Dha16    |
|-----|-----|-----|-----|------|------|------|----------|
| F3W | G7N | G8A | G9A | G10V | V11I | L14V | Dha16G   |
|     |     | G8N | G9H | G10Y | V11M | L14M | Dha16Dhb |
|     |     |     |     |      | V11L | L14I | Dha16H   |
|     |     |     |     |      |      |      | Dha16A   |

Variants which comprise a modification selected from the group F3W, G8A, G9A, G9H, V11I, V11L, L14I, L14M, L14V, Dha16G and Dha16Dhb are particularly preferred.

In one aspect, the mersacidin variants may comprise a combination of two or more of the above modifications, for example from 1 to 4, such as 2 or 3 of the modifications (with the remaining residues being that of the wild-type mersacidin sequence). Thus in one aspect, a variant comprising any one of the above-mentioned modifications may be a variant consisting of two, three or four changes in combination, or just consisting of a single positional change.

In one aspect, we have found the change F3W to provide a mersacidin variant ("mersacidin F3W") which has activity against a range of microoganisms which is more potent than mersacidin itself. Thus in one aspect, the mersacidin variant may comprise F3W together with one, two or three other changes. Such mersacidins include mersacidin F3W G8A, mersacidin F3W G9A, mersacidin F3w G9H, mersacidin F3w V11I, mersacidin F3W V11L, mersacidin F3W L14G, mersacidin F3W L14M, mersacidin F3W L14V, mersacidin F3W Dha16G and mersacidin F3W Dha16Dhb.

In another aspect, the mersacidins include mersacidin G8A G9A, mersacidin G8A G9H, mersacidin G8A V11I, mersacidin G8A V11L, mersacidin G8A L14I, mersacidin G8A L14M, mersacidin G8A L14V, mersacidin G8A Dha16G and mersacidin G8A Dha16Dhb.

In another aspect, the mersacidins include mersacidin G9A V11I, mersacidin G9H V11I, mersacidin V11I L14I, mersacidin V11I L14M, mersacidin V11I L14V, mersacidin V11I Dha16G and mersacidin V11I Dha16Dhb.

In another aspect, the mersacidins include mersacidin G9A L14I, mersacidin G9H L14I, mersacidin V11L L14I, mersacidin L14I Dha16G and mersacidin L14I Dha16Dhb.

In another aspect, the mersacidins include Dha16Dhb, mersacidin G9A Dha16Dhb, mersacidin G9H Dha16Dhb, mersacidin V11L Dha16Dhb, mersacidin L14M Dha16Dhb, and mersacidin L14V Dha16Dhb.

In-trans Complementation

In another aspect of the invention, an expression vector encoding and capable of expressing a mersacidin or a lantibiotic peptide which is a mersacidin derivative may be expressed in a ΔMrsA HIL cell, or a ΔMrsA host cell comprising the mrs gene cluster. The expression vector may have the features described in the preceding section. The expression vector may additionally comprise an MrsR1 coding sequence. This is preferred in the case of a ΔmrsA HIL in which the mrsA gene has been disrupted in such a way that the downstream mrsR1 gene is not expressed, though is not essential where the mrsA gene product is produced but in an inactive form.

In one aspect, the ΔMrsA HIL may be an E17A HIL as described by Szekat et al. Such a host cell expresses an inactive mersacidin derivative, but an active MrsR1. Introducing an expression vector which encodes mersacidin or an active derivative thereof will result in the cell having antibacterial activity.

The expression vector may be an autonomously replicating vector, or may be integrated into the host cell. In the case of the latter, integration may occur outside the mrs gene cluster.

The ΔMrsA HIL or host cell may also be ΔSigH.

The expression vector may be a vector comprising an expression cassette of the invention.

In a preferred aspect, the expression vector encodes a mersacidin derivative selected from the group mersacidin F3W, mersacidin G8A and mersacidin F3W G8A.

Homologous Recombination

Szekat et al. (2003) Appl. Env. Microbiol. 69, 3777-3783 describe the construction of an expression system for generation of variant mersacidins. Modified mrsA genes are generated by site-directed mutagenesis using a commercial phagemid system. The modified genes are then excised and ligated into a temperature sensitive plasmid which replicates in Gram-positive bacteria such as *Bacillus* sp. The plasmids are introduced into *Staphylococcus carnosus* by protoplast transformation and then introduced into the mersacidin-producing *bacillus* again by protoplast transformation. The bacilli are then grown at elevated temperature so that the plasmid cannot replicate autonomously and thus integrates into the chromosome by homologous recombination in the mrsA region. At this stage the *bacillus* now contains the entire expression plasmid inserted into the mersacidin biosynthetic pathway and hence has two copies of the mrsA gene, one of which is mutated and the other wild-type. These constructs are reported not to produce either mersacidin or the engineered variant.

The next stage is to grow these constructs for a large number of generations without selection for the plasmid in order to allow a second recombination event to occur to excise the plasmid and to leave a single copy of the mrsA gene. Depending on where the recombination events occur this can either reconstruct the wild-type mrsA gene or generate the engineered variant and clones need to be screened to identify one in which the desired event has occurred.

The net result is a direct replacement of the wild-type mrsA gene by a mutant gene in the chromosome.

In the expression system described by Szekat et al. (2003) a double recombinant must be selected. When the second recombination event occurs it can lead to recovery of the parent construct at least as efficiently as gene replacement. In order to generate the second recombination event, the strains must be grown through many generations under conditions which are not selective for maintenance of the plasmid. This procedure together with examination of the clones to select those that have performed the double cross over and have kept the mutated gene is laborious and time consuming.

This technique may be used in the present invention so as to introduce sequences encoding mersacidin variants in a ΔSigH or ΔMrsA ΔSigH host cell of the invention. In essence, the technique comprises:

providing an expression vector encoding a mersacidin variant;

introducing the vector into said host cell;

integrating the vector by homologous recombination into the mrsA locus of the host cell;

selecting for a second homologous recombination event to occur to excise the vector and to leave a single copy of the variant gene.

However, the present invention provides a simpler procedure which involves fewer manipulations and without the need to screen out large numbers of regenerated parental strains.

In the present invention a plasmid is inserted containing an intact mrsR1 gene as well as an intact mrsA (or coding region for a mersacidin derivative; for convenience in this section reference is made to mrsA but it will be understood this teaching applies to other mersacidin derivatives). Additionally the orientation of the chloramphenicol resistance gene has been inverted compared with the earlier work in order to circumvent any issues of readthrough from this gene. When this plasmid was inserted into a strain producing the inactive mersacidin E17A variant (generated by double homologous recombination; Szekat et al. 2003) active mersacidin was produced. This therefore demonstrates a system which may be used to generate variant mersacidins using a single recombination event.

In a preferred aspect, the integrative plasmid contains a selectable marker (e.g. chloramphenicol acetyl transferase), and preferably the selectable marker is transcribed in the opposite orientation to the mrsA gene of the plasmid.

Transformation

Although in practicing the present invention the *Bacillus* HIL cells may be transformed using protoplast transformation, as described in the prior art, the present invention also provides an improved transformation protocol utilising electroporation.

Prior to the present invention, it had not been demonstrated that electroporation of *Bacillus* HIL was possible, and indeed the accompanying examples demonstrate that using standard techniques gave no transformants of *Bacillus* HIL.

Accordingly, the present invention provides a method for the transformation of recipient *Bacillus* HIL cells (including ΔSigH, ΔMrsA and ΔMrsA ΔSigH cells) with plasmid DNA, which method includes the steps of:

growing plasmid DNA in a host cell such that said DNA is free of methylation;

isolating said plasmid DNA;

growing said recipient cells in a growth medium supplemented with an osmostabilizer;

harvesting said recipient cells to remove the growth medium;

resuspending said recipient cells in an electroporation medium comprising an osmostabilizer; and electroporating said recipient cells with said plasmid DNA.

The osmostabilizer may be a sugar such as sucrose or fructose, or a polyol such as glycerol, sorbitol or mannitol, or mixtures of two or more of any of these components. Sorbitol and mannitol are preferred, and particularly mixtures thereof.

The growth medium may be tryptic soy broth or other medium used in the art for culture of *Bacillus*. The osmostabilizer(s) in the growth medium may be present at a total concentration in the range of 0.5M to 2.0M preferably 1.0 M.

Preferably the growth medium includes a mixture of sorbitol in the concentration range of from 0.2 to 1.0M, preferably about 0.5M, and mannitol in the range of 0.2M to 1.0M, preferably about 0.5M.

Cells are Generally Harvested After the Start of the Stationary Phase.

The osmostabilizer(s) in the electroporation medium may be present in the range of from 0.5 to 3.0M, preferably about 1.5 to 2.0 M. Preferably the electroporation medium contains a mixture of sorbitol in range of from 0.2M to 1.0M, preferably 1M, and mannitol in the range of from 0.2 to 1.0M, preferably 0.75M. The electroporation medium may also contain glycerol, for example from 5 to 30%, preferably 10% v/v.

Electroporation may be performed using standard techniques. The conditions used in the accompanying examples are one set of suitable conditions, and may be used generally in the practice of the present invention. However these may be varied and the precise conditions will depend upon the preferences of those of skill in the art, for example depending upon the apparatus available.

Following electroporation, cells are cultured in a suitable recovery medium. In a preferred aspect, the recovery medium also comprises sorbitol and mannitol, which typically may both be within the concentration ranges set out above for the electroporation medium. The recovery medium also comprises a growth medium, such as tryptic soy broth.

In a preferred aspect, the plasmid DNA is obtained by growth of the plasmid in an $E.$ $coli$ host cell deficient in DNA methylases, such as a dam dcm strain. This embodiment assumes that the plasmid has an origin of replication functional in $E.$ $coli$. Alternatively, the plasmid DNA may be prepared from $S.$ $carnosus$ or any other natural methylation deficient host.

The process of the invention may be used to obtain frequencies of transformation of at least about 100, preferably at least about 500 and more preferably at least about 1,000 colonies per pg of DNA.

Recovery of Lantibiotics and Production of Mersacidin Variants

The invention also provides a method of making a mersacidin variant which method comprises culturing a host cell of the invention in a culture medium and recovering the mersacidin variant from the medium.

Recovering the mersacidin or other lantibiotic from the medium may be achieved by standard techniques in the art, such as separation from other components of the culture medium by chromatographic means. Such means include the use of hydrophobic resins, reversed phase chromatography, ion exchange chromatography and HPLC. The recovery of mersacidin is illustrated in U.S. Pat. No. 5,112,806.

One process which may be used is to bind the mersacidin from the culture supernatant onto a hydrophobic resin such as HP20, then elute with acetonitrile-water or methanol-water. This is followed by dilution with water so as to allow binding onto a hydrophobic column such as a C18 reversed phase resin. The mersacidin is then eluted with acetonitrile or methanol and the eluate evaporated to reduce volume. The pH is then adjusted to about pH 2.5 with phosphate buffer and the solution bound onto a strong cation exchanger such Varian SCX, followed by elution with 50% methanol, 250 mM phosphate buffer pH7. The eluate is desalted on another C18 column, eluted with methanol, then lyophilised.

This procedure may also be used to recover mersacidin variants, though where said variants have a different charge from mersacidin alterations to the process may be introduced.

For example, the ion exchange step may be altered or omitted if the charge is different and hplc might be utilised. If the mersacidin variant is partly bound to the bacteria in which it is produced the product may be released by treatment with methanol, acetonitrile or similar solvents.

Reference herein to "recovery" or "recovering" includes the purification of the mersacidin or variant thereof to a degree such that it will be suitable for pharmaceutical use. Thus generally recovery will include the steps of removal of the microorganism (e.g. by centrifugation or filtration), separating the lantibiotic from other bacterial components present in the culture medium, and optionally if desired components of the culture medium. Thus the mersacidin or variant thereof will be in substantially isolated form.

The mersacidin or variant thereof may be recovered in a solution, such as a buffer required to elute the mersacidin or variant thereof from a chromatography column, or it may be recovered in the form of a lyophilized fraction.

The mersacidin or variant thereof may be in the form of a salt, particularly a pharmaceutically acceptable salt. These include basic salts, such as an alkali or alkaline earth metal salt, e.g. a sodium, potassium, calcium or magnesium salt. The salt may also be an acid addition salt such as those formed with hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

A potassium salt is preferred. The preparation of a potassium salt is described in U.S. Pat. No. 5,112,806.

Preparation of Formulations and Compositions.

The recovered lantibiotic or salt thereof may be brought into contact with a pharmaceutically acceptable carrier or diluent to provide a pharmaceutical composition. The composition may be in the form of a liquid, gel or solid.

The mersacidin variants of the invention may be provided in substantially isolated form, e.g. free or substantially free of material with which they are associated with in a host cell used for their production.

The mersacidin variant may be in the form of a salt, particularly a pharmaceutically acceptable salt. These include basic salts, such as an alkali or alkaline earth metal salt, e.g. a sodium, potassium, calcium or magnesium salt. The salt may also be an acid addition salt such as those formed with hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. A potassium salt is preferred. The preparation of a potassium salt is described in U.S. Pat. No. 5,112,806.

The mersacidin variant may be prepared in the form of a pharmaceutical composition, The composition may be in the form of a liquid, gel or solid.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. Oral, nasal and topical administration may include administration by way of aerosols.

Topical formulations may also be present in the form of creams, ointments or gels, depending upon the site of intended use. Topical compositions of the invention may be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product. The composition may also contain the usual adjuvants in the cosmetics and dermatological fields, such as one or more of a hydrophilic or lipophilic gelling agent, hydrophilic or lipophilic active agent, preserving agent and antioxidant. When the composition of the invention is an emulsion, the proportion of the fatty phase can range from 5 to 80% by weight, and preferably from 5 to 50% by weight, relative to the total weight of the composition. The oils, the emulsifiers and the co-emulsifiers used in the composition in emulsion form are chosen from those used conventionally in the field considered. The emulsifier and the co-emulsifier are present in the composition in a proportion ranging from 0.3 to 30% by weight, and preferably from 0.5 to 20% by weight, relative to the total weight of the composition.

Oils which can be used include mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol) fatty acids and waxes (carnauba wax, ozokerite) can also be used as fatty substances.

Emulsifiers and co-emulsifiers which can be used include, for example, of fatty acid esters of polyethylene glycol, such as PEG 20 stearate, and fatty acid esters of glycerol, such as glyceryl stearate.

The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see "Remington: The Science and Practice of Pharmacy", 20th Edition, 2000, pub. Lippincott, Williams & Wilkins. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like.

In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

Another approach for parenteral administration employs the implantation of a slow-release or sustained-release system, such that a constant level of dosage is maintained. See, e.g., U.S. Pat. No. 3,710,795.

Dosage forms or compositions containing active ingredient in the range of 0.1 to 95% with the balance made up from non-toxic carrier may be prepared. Preferably, percentages of active ingredient of 0.1% to 50% in solution are employable.

Combined Preparations

Compositions of a mersacidin variant of the invention may also comprise a second active agent, including a different mersacidin variant including those described herein, a different antibacterial agent, or another agent intended to treat a second symptom or cause of a condition to be treated.

Various antibacterial agents can be used in conjunction with the mersacidin variants of the present invention. These include quinolones, tetracyclines, glycopeptides, aminoglycosides, β-lactams, rifamycins, coumermycins, macrolides, ketolides, azalides, and chloramphenicol. In particular embodiments an antibiotic of the above classes can be, for example, one of the following:

β-Lactam Antibiotics: imipenem, meropenem, biapenem, cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000 and LY206763.

Macrolides: azithromycin, clarithromycin, erythromycin, oleandomycin, rokitamycin, rosaramicin, roxithromycin, and troleandomycin.

Ketolides: ABT-773, Telithromycin (HMR 3647), HMR3562, HMR3004, HMR3787, ABT-773, CP-654,743, C2-fluoro ketolide, A1957730, and TE802.

Quinolones: amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, ΔM-1155, NM394, T-3761, rufloxacin, OPC-17116, DU-6859a, and DV-7751a.

Tetracyclines: chlortetracycline, demeclocycline, doxycycline, lymecycline, methacycline, minocycline, oxytetracycline, and tetracycline.

Glycopeptides: vancomycin and derivatives thereof.

Aminoglycosides: amikacin, arbekacin, butirosin, dibekacin, fortimicins, gentamicin, kanamycin, meomycin, netilmicin, ribostamycin, sisomicin, spectinomycin, streptomycin, tobramycin, clindamycin, and lincomycin.

Rifamycins: rifamycin SV, rifamycin O, rifabutin, rifampicin, rifampin, and rifalizil.

Instead of a second antibacterial agent, the composition may comprise a second agent intended to treat a further symptom or cause of a condition to be treated by the mersacidin variant. For example, the composition may comprise an analgesic agent, e.g. a non-steroidal anti-inflammatory compound. Particularly where the composition is for the treatment of skin infections, the composition may comprise a dermatological agent such as a steroid, for treatment of inflammation of the skin. Other agents which may be useful in dermatological applications include retinoids, bactericidal agents such as benzoyl peroxide and anti-fungal agents.

In these aspects of the invention, the mersacidin variant to be combined with a second active agent may be any one of the variants mentioned above, including mersacidin F3W, mersacidin G8A, and mersacidin F3W G8A.

Uses of Mersacidin Variants

Mersacidin variants of the invention (including compositions thereof as described above) may be administered to a human or animal subject in methods of treatment, for example in the treatment of bacterial infection, particularly MRSA (methicillin resistant *staphylococcus aureus*) infection. Such treatment may comprise the step of administering to a subject in need of treatment an effective amount of said mersacidin variant or composition thereof.

Thus the invention also provides a mersacidin variant or composition thereof for use in a method of treatment or prophylaxis of the human or animal body. The invention also provides a mersacidin variant or composition thereof for use in a specific method of treatment or prophylaxis of the human or animal body, the specific method including those described herein below. The invention also provides the use of a mersacidin variant or composition thereof for the manufacture of a medicament for use in a specific method of treatment or prophylaxis of the human or animal body, the specific method including those described herein below.

Thus the variants or compositions thereof of the invention may be used for the treatment of bacterial infections, including systemic bacterial infections, caused by bacteria including *Clostridium difficile*, *Staphylococcus* spp., *Streptococcus* spp, *Enterococcus* spp, *Propionibacterium acnes*, and *Helicobacter pylori*.

The *Staphylococcus* spp. may be coagulase-negative staphylococci. The *Staphylococcus* spp may be in particular *Staphylococcus epidermidis*. The *Staphylococcus* spp may be *Staphylococcus aureus* including drug-resistant species, such as MRSA, VISA (Vancomycin Intermediate *Staph. aureus*), VRSA (Vancomycin Resistant *Staph. aureus*), GISA (glycopeptide-intermediate *Staph. aureus*), LRSA (linezolid-resistant *Staph. aureus*), or mupirocin-resistant *Staph. aureus*. The *Streptococcus* spp. may be *Streptococcus pyogenes*, *Streptococcus agalactiae*, or *Streptococcus pneumoniae*. *Enterococcus* spp. include *Enterococcus faecium*, *Enterococcus. faecalis*.

The variants and composition may be used for systemic treatment of bacteraemia (including catheter related bacteraemia), pneumonia, skin and skin structure infections (including surgical site infections), endocarditis and osteomyelitis. The variants or compositions may also be used for topical treatment of skin infections including acne ie. *Propionibacterium acnes*. The variants and compositions thereof may also be used in the treatment of eye infections, such as conjunctivitis, and for oral treatment for gut super-infection, such as that caused by *Clostridium difficile* including multiply-resistant *C. difficile* (pseudomembranous colitis), or gut infections associated with *Helicobacter pylori*.

The variants may also be used in the treatment or prevention of infection of the skin in wounds or burns. In addition, the variants and compositions thereof may be used in prophylactic methods, such as for the clearance of the nares to prevent transmission of MRSA. This may be practiced on subjects at risk of infection (e.g. patients entering a hospital) or on health professionals or other carers at risk of being carriers of such infections. Prophylactic clearance of gut flora ahead of abdominal surgery is also contemplated.

The effective amount of the mersacidin variant to be administered will ultimately be at the discretion of the physician, taking into account the severity of the disease in a particular subject (e.g. a human patient or animal model) and the overall condition of the subject. Suitable dose ranges will typically be in the range of from 1 to 50 mg/kg, e.g. from 5 to 25 mg/kg, with doses typically being.,administered in twice daily, daily or every other day as the physician finds appropriate.

Nucleic Acids

In another aspect, the invention provides a nucleic acid, generally a DNA, coding for a peptide precursor of a mersacidin variant of the invention. By "precursor", it is meant coding for the naturally occurring amino acids which are post-translationally modified by other elements of the mrsA gene cluster to produce mersacidin. Thus for example mersacidin G10Dha may be encoded by a sequence at which codon 10 is for serine.

The nucleic acid may be fused in-frame to nucleic acid encoding the N-terminal 48 amino acids of the mrsA protein leader sequence. The nucleic acid, or its fusion may be present in a replicable vector. The vector, e.g. a plasmid vector, may contain an origin of replication (e.g. a replication origin functional in a bacterial host cell, particularly a *Bacillus* host cell), together with other elements such as an antibiotic marker gene. One or more other genes of the mrsA gene cluster may be present in the vector. For example, the mrsR1 gene may be present in the vector.

The nucleic acid sequence may also form part of the mersacidin biosynthesis gene cluster, in which it has replaced the mrsA wild-type gene. Such a replacement may be achieved by homologous recombination.

Nucleic acids of the invention may be made by any standard methodology known as such in the art. Typically, the nucleic acids are made by oligonucleotide mutagenesis of the mrsA gene, as described by Szekat et al, though any other suitable method may be used.

Host Cells

The nucleic acids of the invention may be present in a host cell, particularly a bacterial host cell such as a *Bacillus* host cell (e.g. *Bacillus* sp. HIL Y-85,54728 or a derivative thereof).

Where the nucleic acid is in the form of a vector, the host cell may comprise a mrsA gene cluster in which the mrsA gene is inactive, e.g. due to mutation of the gene sequence such that no transcription occurs, or due to the presence of a mutation which results in an inactive gene product (e.g. mersacidin E17A).

A restriction map of the mrs gene cluster is shown in Altena et al, 2000. The sequence of this cluster is available as GenBank accession number: AJ250862. Using the deposited HIL strain as a source of DNA, the overlapping restriction fragments illustrated in Altena et al may be obtained by, for example, PCR amplification based on primers derived from AJ250862. These fragments are assembled using standard cloning procedures and the mrs gene cluster cloned into a suitable cloning vector. Such a vector may be pTRKH2 (O'Sullivan and Klaenhammer 1993).

The vector may be transformed into a laboratory strain of B. subtilis such as B. subtilis 168 in order to replicate, and plasmid DNA isolated from this host. The plasmid may be integrated into this host, or recovered and introduced into other host cells, particularly low-GC Gram positive host cells. These include Bacillus species, particularly B. subtilis, as well as for example S. carnosus.

Accordingly the present invention provides a bacterial host cell which carries a vector comprising the mrs gene cluster and one of a vector of the present invention or wherein the mrs gene cluster has been modified to produce a mersacidin variant of the present invention. The invention also provides a bacterial host cell in which the mrs gene cluster has been integrated into the genome, wherein said cell produces a mersacidin variant of the present invention.

In a preferred aspect, the host cell is Bacillus sp. HIL Y-85,54728. In another aspect, the invention may be a SigH deficient Bacillus sp. HIL Y-85,54728 ("ΔSigH HIL Y-85, 54728"), or a Bacillus species carrying the mrsA gene cluster in which the mrsA gene codes for a variant mersacidin of the present invention. We have found that the use of ΔSigH HIL Y-85,54728 can provide certain advantages for improved production of mersacidin and its variants, as discussed herein below.

Sigma H is the product of the sigH (or spo0H) gene. It is essential for transcription of genes that function in the transition from exponential to stationary phase and in the induction of sporulation. Mutants deficient in SigH do not sporulate. SigmaH activates transcription of a number of other regulatory proteins e.g. spo0A, spo0F, kinA, spo0M, spoVG, spoVS and the spoIIA family as well as the phr family of secreted peptide pheromones. For further details see Britton et al. J Bacteriol. 184, 4881-90; 2002.

ΔSigH HIL strains of the invention may be made utilising the HIL strain deposited as NCIMB Accession Number NCIMB 41211, deposited 19th Mar. 2004. In order to make the ΔSigH derivative, the SigH gene in the HIL strain may be inactivated in accordance with standard techniques available in the art, including for example homologous recombination. Such techniques are described further in herein.

In another aspect, the ΔSigH HIL may also be an HIL derivative in which the mrsA gene product is inactive, either because the mrsA gene is transcriptionally inactive, or because the gene product is a mutant which does not show antibacterial activity against bacteria which are normally killed by mersacidin. Such bacteria include Micrococcus luteus, such as M. luteus ATCC 4498.

A ΔMrsA HIL in which the mrsA gene is inactivated by insertion into the mrsA gene of an erythromycin resistance gene is disclosed in Altena et al, 2000. Another ΔMrsA HIL is the E17A HIL disclosed by Szekat et al, 2003. A further ΔMrsA HIL is one in which the mrsA gene is altered to include a stop codon resulting in a truncated and inactive gene product. All these and other ΔMrsA HIL strains may be used to produce ΔMrsA ΔSigH HIL strains for use in the invention.

Having generally described this invention, the following examples are provided to further describe this invention and fully enable those skilled in the art to make and use this invention, including its best mode. However, the scope of this invention should not be interpreted as limited to the specifics of these examples, but rather, for that purpose, reference should be made to the appended claims and equivalents thereof.

EXAMPLE 1

ΔSigH HIL

Construction of the SigH Knockout Mutant:

A mutant of the mersacidin-producing strain Bacillus sp. HIL Y-85,54728 (NCIMB Accession Number NCIMB 41211, deposited 19th Mar. 2004) has been generated in which sigH was inactivated by insertion of a plasmid (pΔ-SIGH1) that carried an internal fragment of sigH (bp 165-488; accession number NC_000964, Entrez-Nucleotide). The protein that is encoded by this fragment carries a deletion in the N-terminus, which is responsible for binding to the −10 region of the σH promoter and a deletion in the C-terminus that is involved in binding to the −35 region of the σH promoter (Lonetto et al. J. Bacteriol. 174, 3843-3849). After integration of this plasmid into the chromosome, two copies of sigH will be present in the chromosome, however both copies will encode inactive proteins (see FIG. 1). The upstream copy will carry the deletion of the C-terminus (bp 489-657) and the downstream copy will encode a protein with a deletion in the N-terminus (bp 1-164). Both proteins will be inactive.

Primers used for amplification of the internal fragment of sigH:

| Primer | Sequence | Restriction site | $T_m$ |
|---|---|---|---|
| SigmaH5' | 5' TAT<u>GGTACC</u>ATAGGGGCGCACAGA GAGGATA 3' (SEQ ID NO:3) | KpnI | 68° C. |
| SigmaH3' | 5' CTT<u>TCTAGA</u>TCTCCCATTTTCATT TCAAT 3' (SEQ ID NO:4) | XbaI | 52° C. |

Template: purified chromosomal DNA of Bacillus sp. HIL Y-85,54728 (prepared according to Altena et al. Applied and Environmental Microbiology 66, 2565-2571; 2000).

PCR Conditions:

| Action | Temperature | Time | Cycle |
|---|---|---|---|
| Denaturation | 94° C. | 2 min | 1 |
| Denaturation | 94° C. | 30 sec | 30 |
| Annealing | 48.5° C. | 30 sec | |
| Extension | 72° C. | 1 min 40 sec | |
| Extension | 72° C. | 10 min | 1 |
| Cool | 4° C. | 10 min | 1 |

PCR with these primers yielded the correct product of 339 bp and another product of approximately 500 bp. The 339 bp fragment was purified from an agarose gel employing MinElute Gel extraction kits (Qiagen, Hilden), digested with KpnI and XbaI and then ligated with the similarly digested temperature-sensitive plasmid pTV0mcs (Guder et al. Applied and Environmental Microbiology 68, 106-113; 2002). The construct (pΔSIGH1) was then transformed into *Staphylococcus carnosus* TM 300 (ATCC 51365) by protoplast transformation (according to Götz & Schuhmacher FEMS Microbiol. Lett. 40, 285-288; 1987) and the transformants incubated at 30° C. The plasmid pΔSIGH1 (4,676 kb) was then isolated from *Staphylococcus carnosus* TM 300 and transformed into the mersacidin producer strain *Bacillus* sp. HIL-85,54728 by protoplast transformation (according to Grosch & Wollweber in Genetic Exchange, Streips et al. eds, pp. 97-105, Marcel Dekker Inc. 1982). Transformants were cultivated at 30° C. on tryptic soy agar containing chloramphenicol (20 mg/l). For integration of the plasmid into the chromosome, a preculture was carried out in tryptic soy broth containing chloramphenicol (20 mg/l) at 30° C., 180 rpm. Diluted aliquots were then plated onto tryptic soy agar containing chloramphenicol (20 mg/l) and the plates were incubated at 42° C. in order to select clones that had integrated the plasmid into the chromosome.

Integration of pΔSIGH1 was verified by PCR using the following primers:

| Primer | Sequence | $T_m$ |
|---|---|---|
| SigH1 | 5' GTGAATCTACAGAACAAC 3' (SEQ ID NO:5) | 50° C. |
| SigH2 | 5' GTACTTCTCCAGCTTGCG 3' (SEQ ID NO:6) | 58° C. |
| pTV0Ins-1 | 5' GATTTACATATGAGTTATGCAG 3' (SEQ ID NO:7) | 58° C. |
| pTV0Ins-2 | 5' CTACTATAACTGGTACTCGC 3' (SEQ ID NO:8) | 58° C. | pTV0Ins-1 and pTV0Ins-2 anneal within pTV0mcs and produce an amplification product of 496 bp that contains the insert and the neighbouring parts of the vector. A PCR product with this primer combination would indicate the presence of free plasmid in the cell. Integration would be indicated by a 596 bp product amplified with SigH1 and pTV0Ins-1 and a 404 bp product amplified with SigH2 and pTV0Ins-2. The bands obtained with the various primer combinations were consistent with integration of pΔSIGH1 in the expected manner.

Properties of the SigH Deficient Strain:

When grown at 42° C. in the presence of the appropriate antibiotic (Mueller-Hinton broth plus 20 mg/l chloramphenicol, 180 rpm, 72 h), the pΔSIGH1 plasmid remained integrated. In contrast to the parent strain, no spores were formed, to test for spore formation, 1 ml of culture was incubated for 1 h at 90° C. in order to kill all vegetative cells. Aliquots of this suspension were then plated on nutrient agar. No colonies were formed by the sigH mutant, whereas $5 \times 10^9$ CFU/ml were counted for the parent strain treated in the same way. The mutant is also characterised by the formation of translucent colonies on LB agar plates after storage at 4C, and sensitivity to chloroform: a colony is overlayed with a drop of chloroform, when the chloroform has evaporated, the plate is incubated at 37° C. Vegetative cells are killed by chloroform, while spores are not sensitive to chloroform. Colonies from the mutant strain were killed by this procedure whereas the parent strain survived.

Antibiotic Production by the SigH Deficient Strain:

The SigH deficient strain was grown for 72 h in production broth (Bierbaum et al. FEMS Microbiol. Lett. 127, 121-126) containing chloramphenicol (20 mg/l) at 42° C. and 190 rpm. Production of mersacidin was similar to the *Bacillus* sp. HIL Y-85,54728 control. Zones of inhibition of growth of *Micrococcus luteus* ATCC 4498 produced by four separate ΔsigH transformants were similar to those obtained with the parent *Bacillus* sp. HIL Y-85,54728 whereas no zone was observed with a strain (rec1; described in Altena et al. 2000) which is deficient in mersacidin production.

The production of (an) antibacterial substance(s) other than mersacidin (see Altena et al. 2000) was inhibited in the SigmaH deficient strains. The SigmaH deficient strain and the parent strain were incubated in LB-broth for 16 hours and the sterilised (filtration) culture supernatant was tested for antibiotic activity against *M. luteus* ATCC 4498 as indicator strain in an agar diffusion assay on a blood agar plate. No significant mersacidin production occurs under these conditions as judged by hplc (on Phenomenex Luna 3μ C18 150 mm×4.6 mm; solvent A: 30% acetonitrile in 20 mM potassium phosphate buffer pH 7.0, solvent B: 65% acetonitrile in 20 mM potassium phosphate buffer pH 7.0. Gradient: 0%B to 100%B in 10 minutes, held at 100%B for 1 minute, then returned to 0% B in 20 seconds. Flow rate: 1 ml/minute, 10 μl injection, UV detection at 268nm). However, the parent strain *Bacillus* sp. HIL Y-85,54728 shows a zone of activity against *M. luteus* under these conditions which is due to one or more other antibiotics. In contrast no inhibition zones were formed by the SigH deficient strain under the same conditions.

Application of the SigH Deletion Strain in an Overlay Assay:

The SigH deletion strain was incubated on production agar (i.e. production broth plus 1.5% agar) for 72 h. The colonies were killed by overlaying with a drop of chloroform. This was then allowed to evaporate and the plate was overlayed with soft agar containing *M. luteus* ATCC 4498. Large inhibition zones were observed (diameter 3.6 cm). When the parent strain was used in a similar fashion the agar overlay was overgrown by bacilli as the spores survive the chloroform treatment.

Figure 2:
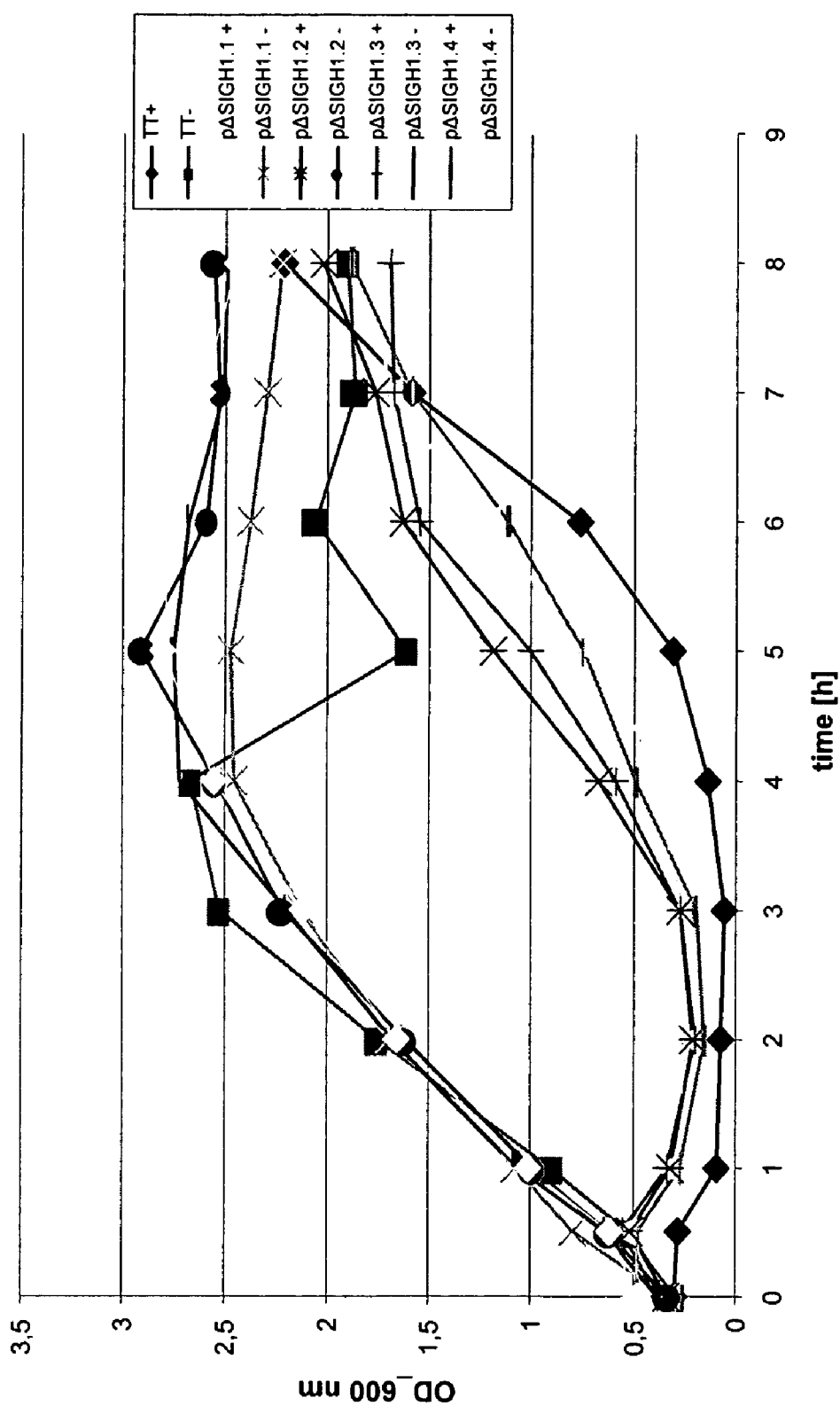
FIG. 2 shows growth curves of of sigH-knockout strains of the invention after addition of 10 mg/ml mersacidin. The symbols + and − in the legend refer to with and without addition of mersacidin.

Immunity of the SigH Deficient Strain to Mersacidin:

The mersacidin biosynthetic cluster contains genes which confer immunity to mersacidin (Altena et al. 2000; Guder et al., 2002). The immunity of the SigH deficient strain was tested in half-strength Mueller Hinton medium after addition of 10 mg/ml mersacidin to the culture at an optical density of about 0.4. The SigH deficient strain resumed growth at least as quickly as the parent strain, indicating that, like mersacidin production, immunity is also unaffected (FIG. 2).

EXAMPLE 2

Stable SigH Deletion Mutant

This example illustrates the construction of a sigh mutant via double homologous recombination. The mutant of Example 1 above is prepared by single homologous recombination. As such it is necessary to use antibiotic selection to maintain the integrant, whereas the new sigH is a stable gene replacement obtained by deletion of a portion of the SigH gene from the bacterial chromosome.

Construction of plasmid pNB029 for Obtaining a SigH Deletion Mutant of Bacillus HIL.

(a) Construction of Plasmid pΔyacP2.

A PCR product containing from base 116152 to base 116766 of the corresponding region of Bacillus HIL chromosome (numbering according to Bacillus subtilis 168 genome sequence NC_000964) was obtained using oligonucleotides yacPEcoRI: 5'-AATGAATTCCAGGAAACAGGGTTATTGTTG (SEQ ID NO:9) and yacPHindIII: 5'-TCCAAGCTTCCTATTAAGAAATAGGATCTTGC (SEQ ID NO:10) and chromosomal DNA of Bacillus HIL as template. The PCR product was purified by agarose gel electrophoresis and eluted from the agarose gel by using the QIAquick Gel Extraction Kit (Qiagen). The purified PCR product was digested with EcoRI and HindIII and ligated to pBT2 previously digested with EcoRI and HindIII and the ligation mixture was used to transform Escherichia coli DH10B (Invitrogen). Ampicillin resistant colonies were selected and the containing plasmids were isolated and characterised by restriction analysis. Plasmids with the expected restriction pattern were further characterised by sequencing. Plasmid containing the expected insert sequence was selected and called pΔyacP2.

(b) Construction of Plasmid pΔrpmG.

A PCR product containing from base 117137 to base 117767 of the corresponding region of Bacillus HIL chromosome (numbering according to Bacillus subtilis 168 genome sequence NC_000964) was obtained using oligonucleotides rpmGHindIII: 5'-GACAAGCTTAGTTACCAAGAGATTTCTGATGA (SEQ ID NO:11) and
rpmGEcoRV: 5'-ATAGATATCCCGCTGAACGGGTTTTGGC (SEQ ID NO:12) and chromosomal DNA of Bacillus HIL as template. The PCR product was purified by agarose gel electrophoresis and eluted from the agarose gel by using the QIAquick Gel Extraction Kit (Qiagen). The purified PCR product was ligated to pUC18 previously digested with SmaI and the ligation mixture was used to transform Escherichia coli DH10B (Invitrogen). Ampicillin resistant colonies were selected and the containing plasmids were isolated and characterised by restriction analysis. Plasmids with the expected restriction pattern were further characterised by sequencing. Plasmid containing the expected insert sequence was selected and called pΔrpmG.

(c) Construction of plasmid pNB029.

Figure 3:
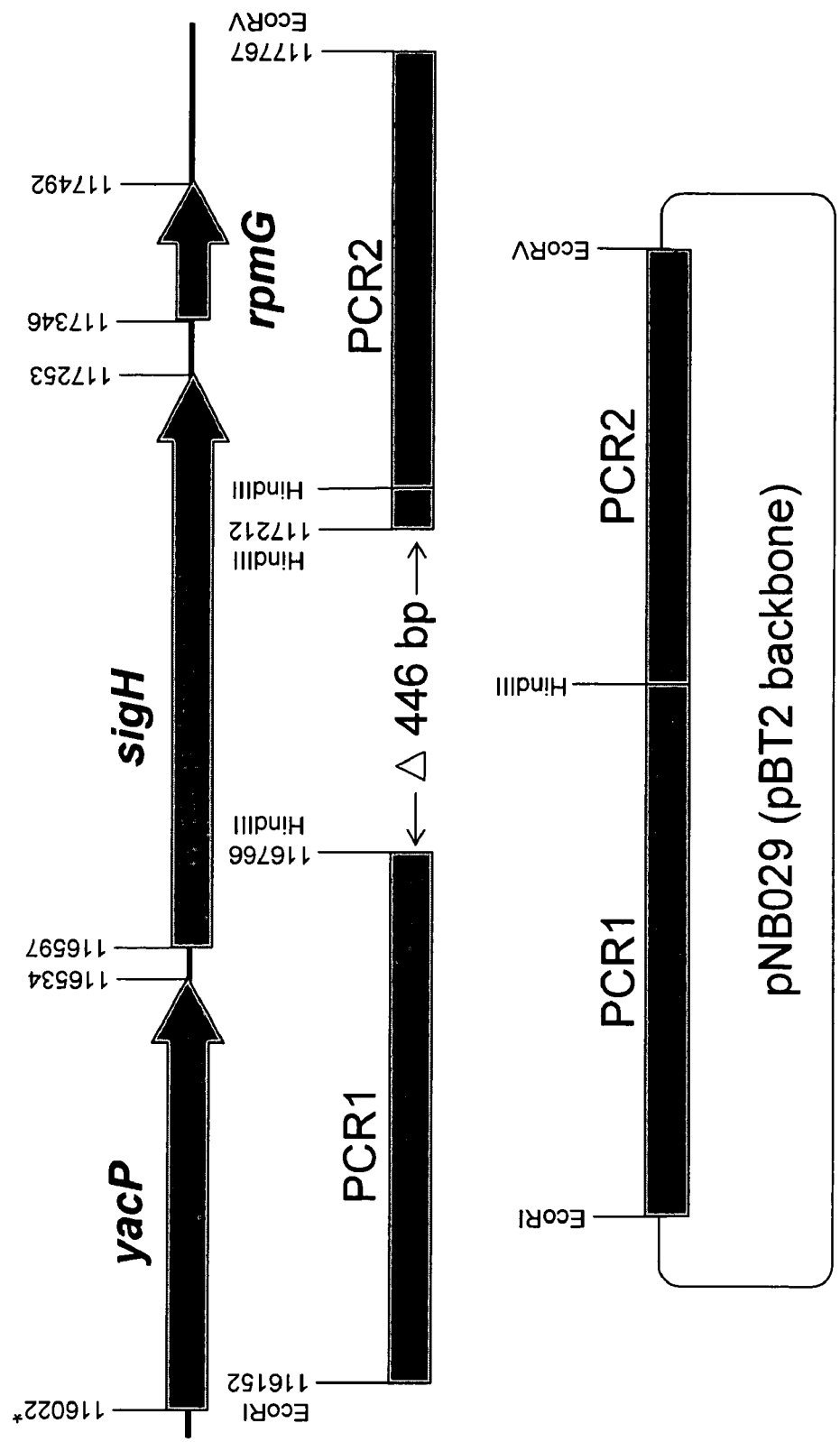
FIG. 3 shows the construction of plasmid pNB029. The numbering indicated is according to *B. subtilis* 168 genome sequence NC_000964.

Plasmid pΔrpmG was digested with HindIII and EcoRV and the insert of approximately 550 bp was purified by agarose gel electrophoresis and eluted from the agarose gel by using the QIAquick Gel Extraction Kit (Qiagen). This insert was ligated to pΔyacP2 previously digested with HindIII and EcoRV and the ligation mixture was used to transform Escherichia coli DH10B (Invitrogen). Ampicillin resistant colonies were selected and the containing plasmids were isolated and characterised by restriction analysis. Plasmid displaying the expected restriction pattern was selected and called pNB029 (FIG. 3).

Generation of Bacillus HIL ΔSigH.

Protoplasts from Bacillus HIL were prepared according to Szekat et al., 2003 and transformed with plasmid pNB029. Chloramphenicol resistant colonies were transferred to tryptic soy agar containing chloramphenicol (20 mg/l) and grown at 30° C. for 24 h. For integration of the plasmid into the chromosome, a preculture in tryptic soy broth plus chloramphenicol (20 mg/l) was carried out at 30° C. and 200 rpm. Diluted aliquots of this preculture were plated onto tryptic soy agar containing chloramphenicol (20 mg/l) and the plates were incubated at 42° C. to select clones that had integrated the plasmid into the chromosome. One colony was selected and grown at 42° C. and 200 rpm on tryptic soy broth containing chloramphenicol (20 mg/l) for 24 hours. Serial dilutions of this culture were plated on tryptic soy agar containing chloramphenicol (20 mg/l) to obtain isolated colonies which have pNB029 integrated into the chromosome of Bacillus HIL. One colony was selected and grown at 42° C. and 200 rpm on 50 ml of tryptic soy broth, after 12 h of growth, 0.05ml of this culture were transferred to 50 ml of tryptic soy broth and grown in the same conditions of the previous culture, 5 consecutive subcultures were carried out and samples of the sixth subculture were titrated and frozen. Colonies from this culture were grown on tryptic soy agar at 30° C. for 24 h and replicated into tryptic soy agar containing chloramphenicol (20 mg/l). Chloramphenicol sensitive colonies were isolated and chromosomal DNA was prepared. DNA samples were analysed by PCR and the colonies that have a deletion in sigH were isolated.

EXAMPLE 3

Cassette Expression System

Figure 4:
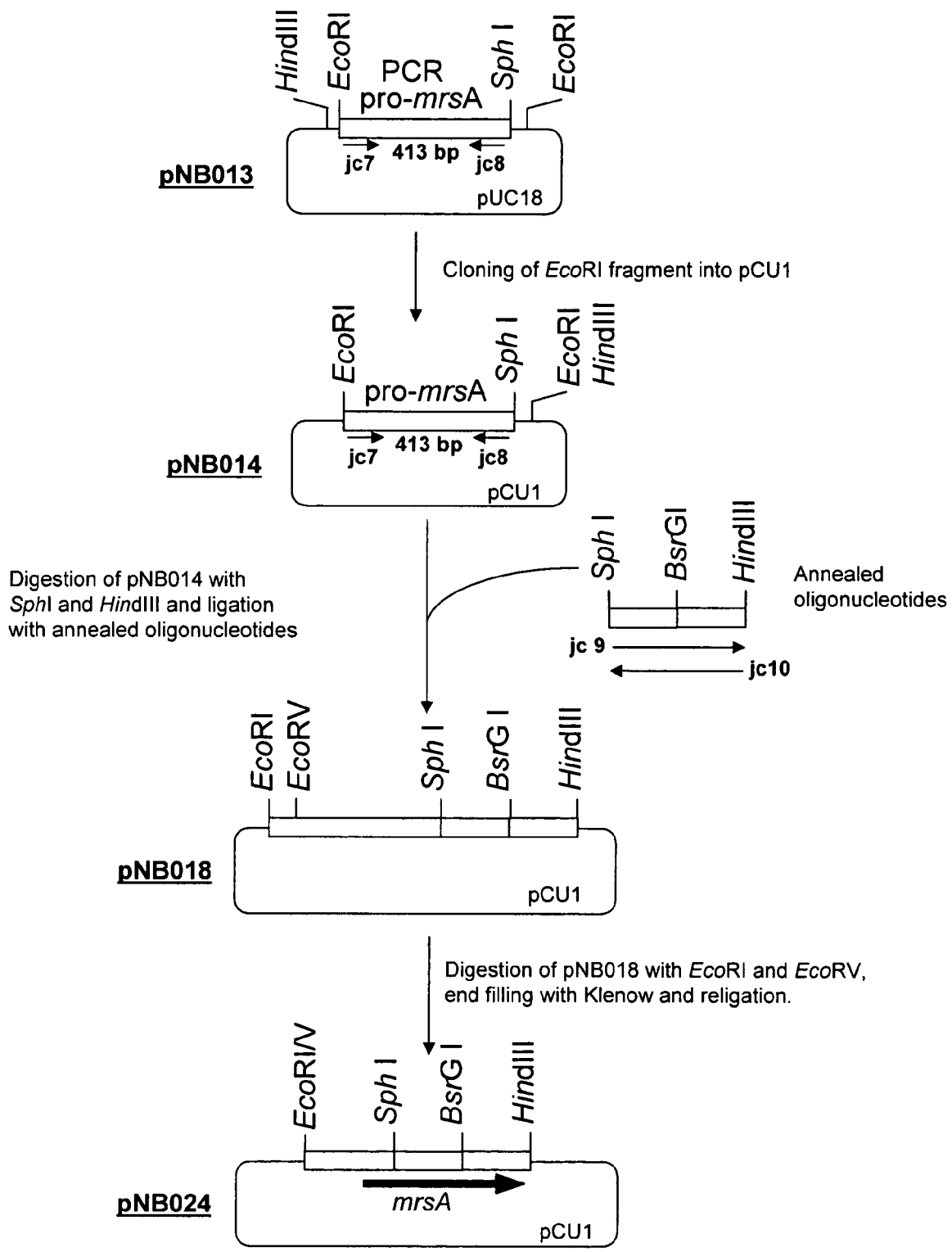
FIG. 4 shows the construction of expression plasmids for a mrsA library.

Construction of Plasmid pNB013:

A PCR product containing from base 4836 to base 5249 of the mersacidin gene cluster (accession number: AJ250862) representing the promoter and leader sequence of mrsA was obtained using oligonucleotides:
jc7 5' CTTATGAGAATTCGAGACAAGGTAAACT (SEQ ID NO:13) and
jc8 5' GCATGCTGCTTCCATGTCTCCCGCACCTACT (SEQ ID NO:14) and plasmid pMER1 (Altena et al., Appl. Env. Microbiol. 66, 2565-2571; 2000) as template. PCR was carried out using a Robocycler Gradient 96 (Stratagene) and the reaction conditions were as follows: Cycle 1; denaturation at 95C for 3 min, annealing at 45C for 1 min, extension at 72C for 1 min, cycle2-26; denaturation at 95C for 1 min, annealing at 45C for 1 min, extension at 72C for 1 min, and a further incubation at 72C for 10 min. The enzyme used was Pfu polymerase (Promega) and the buffer and dNTPs composition and concentration used was the recommended by the suppliers. The PCR product was purified by agarose gel electrophoresis and eluted from the agarose gel by using the QIAquick Gel Extraction Kit (Qiagen). The purified PCR product was ligated to pUC18 (Norrander, J., Kempe, T. and Messing, J. (1983) Construction of improved M13 vectors using oligodeoxynucleotide-directed mutagenesis. Gene 26:101-106.) previously digested with SmaI and the ligation mixture was used to transform Escherichia coli DH10B (Invitrogen). Ampicillin resistant colonies were selected and the contained plasmids were isolated and characterised by restriction analysis. Plasmids with the expected restriction pattern were further characterised by sequencing using M13mp18 reverse and forward primers. Plasmid containing the expected insert sequence and ligated into pUC18 in the orientation that the insert can be excised by digesting with EcoRI was selected and called pNB013 (FIG. 4).

Construction of Plasmid pNB014.

Plasmid pNB013 was digested with EcoRI and the 425 bp DNA fragment generated in this reaction was purified by agarose gel electrophoresis and eluted using the QIAquick Gel Extraction Kit (Qiagen). The purified fragment was ligated to pCU1 (Augustin et al. Eur. J. Biochem. 204, 1149-1154; 1992) previously digested with EcoRI and treated with shrimp alkaline phosphatase (Amersham Life Sciences). The ligation mixture was used to transform E. coli DH10B (Invitrogen), ampicillin resistant colonies were selected and the contained plasmids were isolated and characterised by restriction analysis. Plasmid with the expected restriction pattern where the 425 bp fragment can be excised by digesting with EcoRI and not with SphI was selected and called pNB014 (FIG. 4).

Construction of Plasmid pNB018.

Plasmid pNB014 was digested with SphI and HindIII and the 5.6 kbp DNA fragment generated in this reaction was purified by agarose gel electrophoresis and eluted using the QIAquick Gel Extraction Kit (Qiagen). This DNA fragment was ligated to the annealed complementary oligonucleotides representing the coding sequence for the propeptide region of mrsA into which a silent mutation has been introduced to create a BsrG1 site which is not present in the natural sequence:

```
jc9:
5' CACTTTTACATTGCCTGGTGGCGGCGGTGTTTG (SEQ ID NO:15)
TACACTAACTTCTGAATGTATTTGTTA jc10:
5' AGCTTAACAAATACATTCAGAAGTTAGTGTACA (SEQ ID NO:16)
AACACCGCCGCCACCAGGCAATGTAAAAGTGCATG
```

The ligation mixture was used to transform *E. coli* DH10B (Invitrogen), ampicillin resistant colonies were selected and the contained plasmids were isolated and characterised by restriction analysis. The plasmids containing the newly introduced BsrGI site were selected and sequenced using M13mp18 reverse primer. The plasmid containing the expected sequence was called pNB018 (FIG. 4). This plasmid is a pCU1 derivative containing the promoter of mrsA and the structural gene mrsA modified in a way that the area encoding the propeptide region of mersacidin from amino acid 1 to 12 can be removed by digestion with the restriction enzymes SphI and BsrGI, the area between amino acids 12-20 with the restriction enzymes BsrGI and HindIII, and the area between amino acids 1-20 with the enzymes SphI and HindIII (FIG. 4).

Plasmid pNB018 may be used for generating libraries of mersacidin variants which will complement, in trans, strains which have a fully active mersacidin biosynthetic cluster including an expressed mrsR1 gene. It is particularly useful for complementing derivatives in which the mrsA gene as been mutated to produce an antibacterially-inactive lantibiotic, or 'knocked out' without affecting mrsR1 expression.

Construction of pNB026.

In order to generate a plasmid for construction of libraries of mutations in the first 11 amino acids of mersacidin with no background wild type mrsA gene, plasmid pNB018 was digested with SphI and BsrGI and the 5.6 kbp DNA fragment generated in this reaction was purified by agarose gel electrophoresis and eluted using the QIAquick Gel Extraction Kit (Qiagen). This DNA fragment was ligated to a purified 1.5 kbp SphI/BsrGI fragment obtained from pNB2008. Plasmid pNB2008 is a pUC18 derivative containing a PCR product from base 5826 to 9353 of the mrs gene cluster (accession number: AJ250862) cloned in the orientation such that base 5826 is close to the EcoRI site and base 9353 to the HindIII in the multiple cloning site of this vector.

Figure 5:
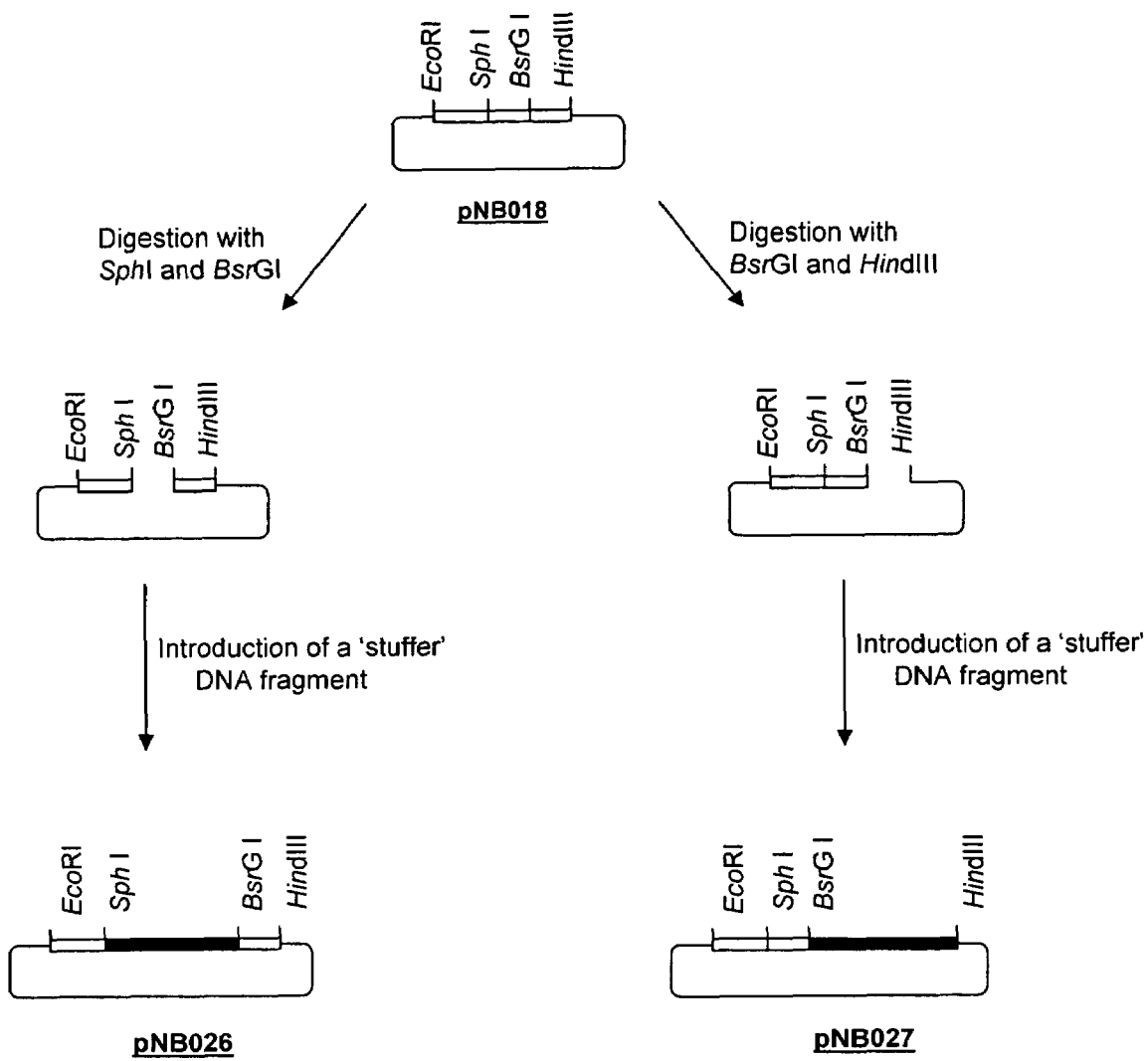
FIG. 5 shows the construction of plasmids of the invention containing stuffer fragments.

The ligation mixture was used to transform *Escherichia coli* DH10B (Invitrogen). Ampicillin resistant colonies were selected and the contained plasmids were isolated and characterised by restriction analysis. Plasmid with the expected restriction pattern was called pNB026 (FIG. 5).

Construction of pNB027.

In order to generate a plasmid for construction of libraries of mutations from amino acid 12 to 20 of mersacidin with no background wild type mrsA gene, plasmid pNB018 was digested with BsrGI and HindIII and the 5.6 kbp DNA fragment generated in this reaction was purified by agarose gel electrophoresis and eluted using the QIAquick Gel Extraction Kit (Qiagen). This DNA fragment was ligated to a purified 930 bp BsrGI/HindIII fragment (from base 7841-8774 of mrs gene cluster) obtained from pNB3002. Plasmid pNB3002 is a pUC18 derivative containing from base 7841 of the mrs gene cluster to the next EcoRI site outside the cluster, downstream of mrsT. The ligation mixture was used to transform *Escherichia coli* DH10B (Invitrogen). Ampicillin resistant colonies were selected and the contained plasmids were isolated and characterised by restriction analysis. Plasmid with the expected restriction pattern was called pNB027 (FIG. 5).

The value of introducing these 'stuffer' DNA fragments is that when the region is replaced by the annealed oligonucleotides to generate the variant library there is a significant decrease in plasmid size. The resulting plasmids can thus be readily purified away from any minor population of unrestricted plasmid thus eliminating any 'background' which would otherwise generate wildtype mersacidin.

Construction of a Library of mrsA Genes.

Plasmid pNB026 was digested with SphI and BsrGI and the 5.6 kbp DNA fragment generated in this reaction was purified by agarose gel electrophoresis and eluted using the QIAquick Gel Extraction Kit (Qiagen). This DNA fragment was ligated to the annealed complementary, degenerate oligonucleotides:

```
jc27:
5' CACTTTTACADTGCCTGBTGBCGBCGBTGBTT  (SEQ ID NO:17)

jc28:
5' GTACAAVCAVCGVCGVCAVCAGGCAHTGTAAAA (SEQ ID NO:18)
GTGCATG
D = A or G or T; B = C or G or T; V = A or C or G;
H = A or C or T.
```

The ligation mixture was used to transform *E. coli* DH10B (Invitrogen). One tenth of the volume of the transformation mixture (0.1 ml) was used to titrate the library by plating on LA+ampicillin (100 mg/l). After growth for 12 h at 37C, ampicillin resistant colonies were counted and a sample of the contained plasmids were isolated and characterised by sequence analysis to assess the diversity of the library. The 0.9 ml remaining of the transformation mixture was inoculated into 100 ml LB+ampicillin (100 mg/l) and incubated at 30C, 250 rpm. After 12 h growth, plasmid DNA was prepared.

The plasmid library is introduced into dcm dam *E. coli* and grown, the plasmid DNA recovered and used to transform E17A HIL. Transformants are screened for anti-bacterial activity.

Construction of Plasmid pNB024.

Plasmid pNB018 was digested with EcoRI and EcoRV and incubated with Klenow fragment of DNA polymerase in the presence of DATP, dTTP, dGTP and dCTP. The 5.4 kbp DNA fragment generated in this reaction was separated and purified by agarose gel electrophoresis and elution using the QIAquick Gel Extraction Kit (Qiagen). The purified fragment was religated and used to transform *E. coli* DH10B (Invitrogen). Ampicillin resistant colonies were selected and the contained plasmids were isolated and characterised by restriction analysis. The plasmid that lost the DNA sequence comprised between EcoRI and EcoRV in positions 4843 and 4997 of the mersacidin gene cluster (accession number: AJ250862) respectively was called pNB024 (FIG. 4). This plasmid is a pNB018 derivative containing a 150 bp deletion at the 5' end of the promoter of mrsA.

Plasmid pNB024 has similar utility to pNB018 but lacks the putative operator site upstream of mrsA and thus gives lower expression of the introduced mrsA variant.

Figure 6:
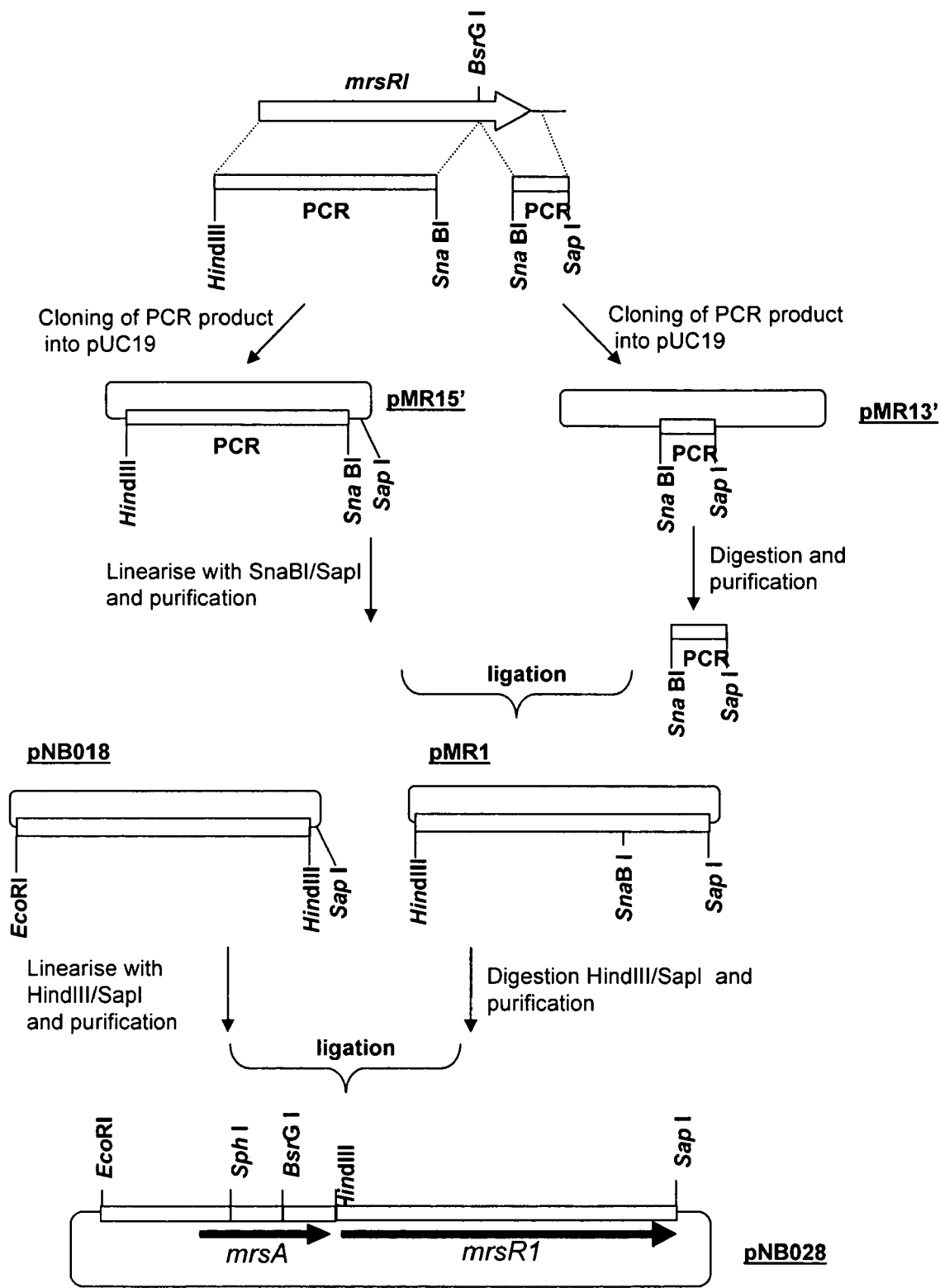
FIG. 6 shows the construction of plasmid pNB028.

Construction of Plasmid pNB028 (see FIG. 6)

A PCR product containing from base 5313 to base 5905 of the mersacidin gene cluster (accession number: AJ250862), representing the 5' end of the mrsR1 gene as far as the BsrG1 site, was obtained using oligonucleotides:

jc36: 5'AAGCTTGATTTATATAGGCTGTTTCCC (SEQ ID NO:19) and jc37: 5'GTGTACGTAAAGACTTGACCTACC (SEQ ID NO:20) and plasmid pMER1 (Altena et al., 2000) as template. PCR was carried out using a Robocycler Gradient 96 (Stratagene) and the reaction conditions were as follows: Cycle 1; denaturation at 95C for 3 min, annealing at 45C for 1 min, extension at 72C for 1 min, cycle 2-26; denaturation at 95C for 1 min, annealing at 45C for 1 min, extension at 72C for 1 min, and a further incubation at 72C for 10 min. The enzyme used was Pfu polymerase (Promega) and the buffer and dNTPs composition and concentration used was the recommended by the suppliers. The PCR product was purified by agarose gel electrophoresis and eluted from the agarose gel by using the QIAquick Gel Extraction Kit (Qiagen). The purified PCR product was ligated to pUC19 (Yanisch-Perron, C., Vieira, J. and Messing, J. (1985) Improved M13 phage cloning vectors and host strains: Nucleotide sequences of the M13mp18 and pUC19 vectors. Gene 33:103-119) previously digested with SmaI and the ligation mixture was used to transform Escherichia coli DH10B (Invitrogen). Ampicillin resistant colonies were selected and the containing plasmids were isolated and characterised by restriction analysis. Plasmids with the expected restriction pattern were further characterised by sequencing using M13mp18 reverse and forward primers. Plasmid containing the expected insert sequence and ligated into pUC19 in the orientation that the insert can be excised by digesting with HindIII was selected and called pMR15'.

A PCR product containing from base 5894 to base 6130 of the mersacidin gene cluster (accession number:AJ250862), representing the 3' end of the mrsR1 gene beyond the BsrG1 site, was obtained using oligonucleotides:

jc32: 5' CTTTACGTACACATTAGTTCTCTTAGAG (SEQ ID NO:21)and jc33: 5' GGAAGCGGAAGAGCTTTAAAGAAAGAA-CAAAACACCCC (SEQ ID NO:22) and plasmid pMER1 (Altena et al., 2000) as template. PCR was carried out using a Robocycler Gradient 96 (Stratagene) and the reaction conditions were as follows: Cycle 1; denaturation at 95C for 3 min, annealing at 45C for 1 min, extension at 72C for 1 min, cycle2-26; denaturation at 95C for 1 min, annealing at 45C for 1 min, extension at 72C for 1 min, and a further incubation at 72C for 10 min. The enzyme used was Pfu polymerase (Promega) and the buffer and dNTPs composition and concentration used was the recommended by the suppliers. The PCR product was purified by agarose gel electrophoresis and eluted from the agarose gel by using the QIAquick Gel Extraction Kit (Qiagen). The purified PCR product was ligated to pUC19 previously digested with SmaI and the ligation mixture was used to transform Escherichia coli DH10B (Invitrogen). Ampicillin resistant colonies were selected and the contained plasmids were isolated and characterised by restriction analysis. Plasmids with the expected restriction pattern were further characterised by sequencing using M13mp18 reverse and forward primers. Plasmid containing the expected insert sequence was selected and called pMR13'.

Plasmid pMR13' was digested with SnaBI and SapI, the 250 bp DNA fragment generated in this reaction was purified by agarose gel electrophoresis and eluted using the QIAquick Gel Extraction Kit (Qiagen). Plasmid pMR15' was linearised by digestion with SnaBI and SapI and ligated to the 250 bp fragment isolated from pMR13'. The ligation mixture was used to transform Escherichia coli DH10B (Invitrogen). Ampicillin resistant colonies were selected and the contained plasmids were isolated and characterised by restriction analysis. Plasmid with the expected restriction pattern was selected and called pMR1. pMR1 contains the entire mrsR1 gene but with a silent mutation to remove the internal BsrG1 site.

Plasmid pMR1 was digested with HindIII and SapI, the 828 bp DNA fragment generated in this reaction was purified by agarose gel electrophoresis and eluted using the QIAquick Gel Extraction Kit (Qiagen). Plasmid pNB018 was linearised by digestion with HindIII and SapI and ligated to the 828 bp DNA fragment isolated from pMR1. The ligation mixture was used to transform Escherichia coli DH10B (Invitrogen). Ampicillin resistant colonies were selected and the contained plasmids were isolated and characterised by restriction analysis. Plasmid with the expected restriction pattern was selected and called pNB028. This plasmid is a derivative of pNB018 containing downstream of the modified mrsA gene, the regulatory gene mrsR1 with a silent mutation to eliminate the BsrGI site present within the sequence of this gene.

Plasmid pNB028 has similar utility to pNB018, but it will also complement strains in which mrsR1 is defective eg due to polar effects of a knockout of mrsA gene (as in rec1 Altena et al. 2000).

EXAMPLE 4

In Trans Complementation

Complementation of Bacillus sp. HIL Y-85,54728 E17A in Trans using pNB018 and pNB024

This strain is a gene replacement mutant where the mrsA gene has been substituted for a mutant mrsA that produces the mersacidin variant E17A with no antibacterial activity (Szekat et al. (2003) Appl. Env. Microbiol. 69, 3777-3783). Plasmids pNB018 and pNB024 were introduced into E. coli dam. dcm strain ET12567 by electroporation. Ampicillin resistant colonies were selected, plasmid DNA was prepared using the Promega Wizard mini-prep kit and concentrated by ethanol precipitation. These plasmid preparations were used to transform electrocompetent cells of Bacillus sp. HIL Y-85, 54728 E17A by the method described previously for Bacillus sp. HIL.

Two transformants from each plasmid were selected and streaked to L-agar containing 20 mg/l chloramphenicol and incubated at 30C for 24 hours. A loopful of growth was used from each to inoculate 7 ml of tryptic soy broth containing 20 mg/l chloramphenicol in a miniaturised culture vessel. These seed cultures were incubated at 30C with shaking at 250 rpm for approximately 24 hours, 0.3 ml of each culture was used to inoculate 7 ml of production medium containing 20 mg/l chloramphenicol in miniaturised culture vessels, which were incubated at 30C with shaking at 250 rpm for 5 days. The composition of the production medium is shown below.

Mersacidin production medium (2× BPM + 300 mM glucose)

| Ingredient | mM | g/l |
|---|---|---|
| (NH4)H2SO4 | 50 | 6.6 |
| MgSO4•7H2O | 2 | 0.492 |
| CaCl2•7H2O | 1 | 0.14 |
| FeSO4•7H2O | 0.2 | 0.06 |
| MnSO4•H2O | 1.0 | 0.18 |
| 1 M potassium phosphate buffer pH 7.0 | 40 | (40 ml of 1 M) |
| 1 M Tris maleate buffer pH 7.0 | 100 | (100 ml of 1 M) |
| Glucose | 400 | 72.8 |

The cultures were assayed for production of mersacidin by HPLC and bioassay against *Micrococcus luteus* ATCC4698. Samples of production cultures (1 ml) were centrifuged at 14000 rpm for 10 minutes. Supernatants were decanted and used undiluted for HPLC and bioassay.

For bioassays, *M.luteus* was inoculated from frozen stock into 10 ml half-strength Muller-Hinton broth in a 50 ml conical flask, and incubated at 30C with shaking at 250 rpm for approximately 7 hours, 0.3 ml of this culture was used to inoculate 300 ml of Muller-Hinton agar which was poured into a bioassay plate. Wells (6 mm diameter) were made with a cork-borer. Samples of 50 µl of supernatants were added to these wells. The concentration of mersacidin in the samples was calculated by comparing the diameter of inhibition zones of samples against a range of concentrations of a pure mersacidin standard.

For HPLC analysis, a gradient system was used. The column was a Phenomenex Luna 3µ C18 150 mm×4.6 mm. Solvent A was 30% acetonitrile in 20 mM potassium phosphate buffer pH 7.0, solvent B was 65% acetonitrile in 20 mM potassium phosphate buffer pH 7.0. The gradient increased from 0%B to 100%B in 10 minutes, held at 100%B for 1 minute, then returned to 0% B in 20 seconds. Total run time was 15 minutes at 1ml/minute, 10 µl injection, detection at UV 268 nm.

The results are shown in the table below, and show that both pNB018 and pNB024 restore mersacidin production in *Bacillus* HIL E17A. Plasmid pNB018 gives mersacidin production levels comparable to the original (wild-type) HIL, but pNB024 gives reduced production.

| Strain | Plasmid | Transformant | Mersacidin mg/L | |
|---|---|---|---|---|
| | | | HPLC | Bioassay |
| E17A | pNB024 | 1 | 15 | 18 |
| E17A | pNB024 | 2 | 13 | 11 |
| E17A | pNB018 | 1 | 52 | 64 |
| E17A | pNB018 | 2 | 36 | 50 |
| E17A | None | | 0 | 0 |
| HIL | None | | 49 | 56 |

Complementation of *Bacillus* sp. HIL Y-85,54728 rec1 by pNB028

This strain is a gene replacement mutant, the mrsA gene has been substituted for an erythromycin resistance gene (ermB) placed in the opposite orientation to mrsR1 (Altena et al., 2000). Plasmid pNB028 was prepared from *E.coli* ET12567, introduced into *Bacillus* HIL Y-85,54728 rec1 by electroporation, and five transformants were tested for mersacidin production using the same conditions and procedure as used for pNB018 and pNB024 previously.

The results are shown below.

| Strain | Transformant | Mersacidin mg/l | |
|---|---|---|---|
| | | HPLC | Bioassay |
| rec1/pNB028 | 1 | 0 | 0 |
| rec1/pNB028 | 2 | 83 | 93 |
| rec1/pNB028 | 3 | 80 | 93 |
| rec1/pNB028 | 4 | 68 | 81 |
| rec1/pNB028 | 5 | 29 | 41 |
| HIL | | 137 | 142 |
| rec1 | | 0 | 0 |

Plasmid pNB028 restored mersacidin production in 4 of 5 transformants tested, to levels of 29-65% compared to wild type levels (i.e. the parental HIL strain). No production was seen in one transformant, and generally in these experiments, approximately 10-20% of transformants failed to make mersacidin. The reason for this is not known, but presumably reflects instability in the strain or in the plasmid construct.

Construction of Mersacidin Derivative Genes and in Trans Complementation.

Plasmid pNB026 was digested with SphI and BsrGI and the 5.6 kbp DNA fragment generated in this reaction was purified by agarose gel electrophoresis and eluted using the QIAquick Gel Extraction Kit (Qiagen). This DNA fragment was ligated to the annealed complementary, degenerate oligonucleotides:

jc15:
5' CACTTTTACATTGCCTGGTGYCGGCGGTGTTT (SEQ ID NO:23)

jc16:
5' GTACAAACACCGCCGRCACCAGGCAATGTAAAA (SEQ ID NO:24)
GTGCATG
R = A or G; Y = C or T

These oligonucleotides are designed so they would produce a mixture of mutant mrsA genes encoding for mersacidin variants G8A or G8V.

The ligation mixture was used to transform *E. coli* DH10B (Invitrogen). Six ampicillin resistant colonies were selected, grown in LB+ampicillin (100 mg/l) and plasmids were isolated and characterised by sequence analysis. From the six clones analysed, four encoded the mutation G8A (pNB2026) and two the mutation G8V. Plasmids encoding each mutant were used to transform *E. coli* ET12567. Plasmids obtained from these strains were used to transform *Bacillus* sp. HIL Y-85,54728 E17A.

Chloramphenicol resistant colonies were selected and grown in 3 ml Tryptic Soy Broth at 30C for 24 hours, 250 rpm and 0.3 ml of these cultures were used to inoculate 7 ml of 2×BPM+300 mM glucose+chloramphenicol (20 mg/l). After five days of incubation at 30C and 250 rpm, a 1 ml sample was collected and centrifuged at 13000 rpm for 10 min, the supernatant was removed, extracted with 1 volume of chloroform and the aqueous phase used for bioassay and HPLC-MS analysis (see accompanying disclosure for method). LC-MS showed for wildtype mersacidin peaks at m/z=913 $(M+2H)^{2+}$, m/z=924 $(M+H+Na)^{2+}$, m/z=932 $(M+H+K)^{2+}$. For G8A peaks were observed at 920, 931, 939 and for G8V at 934, 945, 953. These masses are consistent with production of the expected mature lantibiotic products. Production of G8A was comparable to mersacidin while the production of G8V was considerably lower. Bioassays against *M. luteus* showed that mersacidin variant G8A has antibiotic activity while the variant G8V was inactive.

Production of a Mersacidin Variant using in Trans Complementation.

Plasmid pNB026 was digested with SphI and BsrGI and the 5.6 kbp DNA fragment generated in this reaction was purified by agarose gel electrophoresis and eluted using the QIAquick Gel Extraction Kit (Qiagen). This DNA fragment was ligated to the annealed complementary oligonucleotides:

```
O/SB34F:
5' CACTTGGACATTGCCTGGTGGCGGCGGTGTTT  (SEQ ID NO:25)

O/SB35R:
5' GTACAAACACCGCCGCCACCAGGCAATGTCCAA (SEQ ID NO:26)
GTGCATG
```

These oligonucleotides are designed so they would produce a mutant mrsA gene encoding for the mersacidin variant F3W.

The ligation mixture was used to transform *E. coli* DH10B (Invitrogen). Ampicillin resistant colonies were selected, grown in LB+ampicillin (100 mg/l) and plasmids were isolated and characterised by sequence analysis. Plasmid encoding the expected mutant (pNB2024) was used to transform *E. coli* ET12567 and the plasmid obtained from this strains was used to transform *Bacillus* sp. HIL Y-85,54728 E17A. Chloramphenicol resistant colonies were selected and grown in 3 ml Tryptic Soy Broth at 30C for 24 hours, 250 rpm and 0.3 ml of these cultures were used to inoculate 7 ml of 2×BPM+ 300 mM glucose+chloramphenicol (20 mg/l). After five days of incubation at 30C and 250 rpm, 1 ml sample was collected and centrifuged at 13000 rpm for 10 min, the supernatant was removed extracted with 1 volume of chloroform and the aqueous phase used for bioassay and HPLC-MS analysis. LC-MS results showed that the mersacidin variant F3W (m/z=932.5 $(M+2H)^{2+}$, m/z=943.5 $(M+H+Na)^{2+}$, m/z=951.5 $(M+H+K)^{2+}$) was produced at concentration comparable to the wild type production of mersacidin. Bioassays against *M. luteus* showed that mersacidin variant F3W has antibiotic activity comparable to mersacidin.

EXAMPLE 5

Single Homologous Recombination

Figure 7:
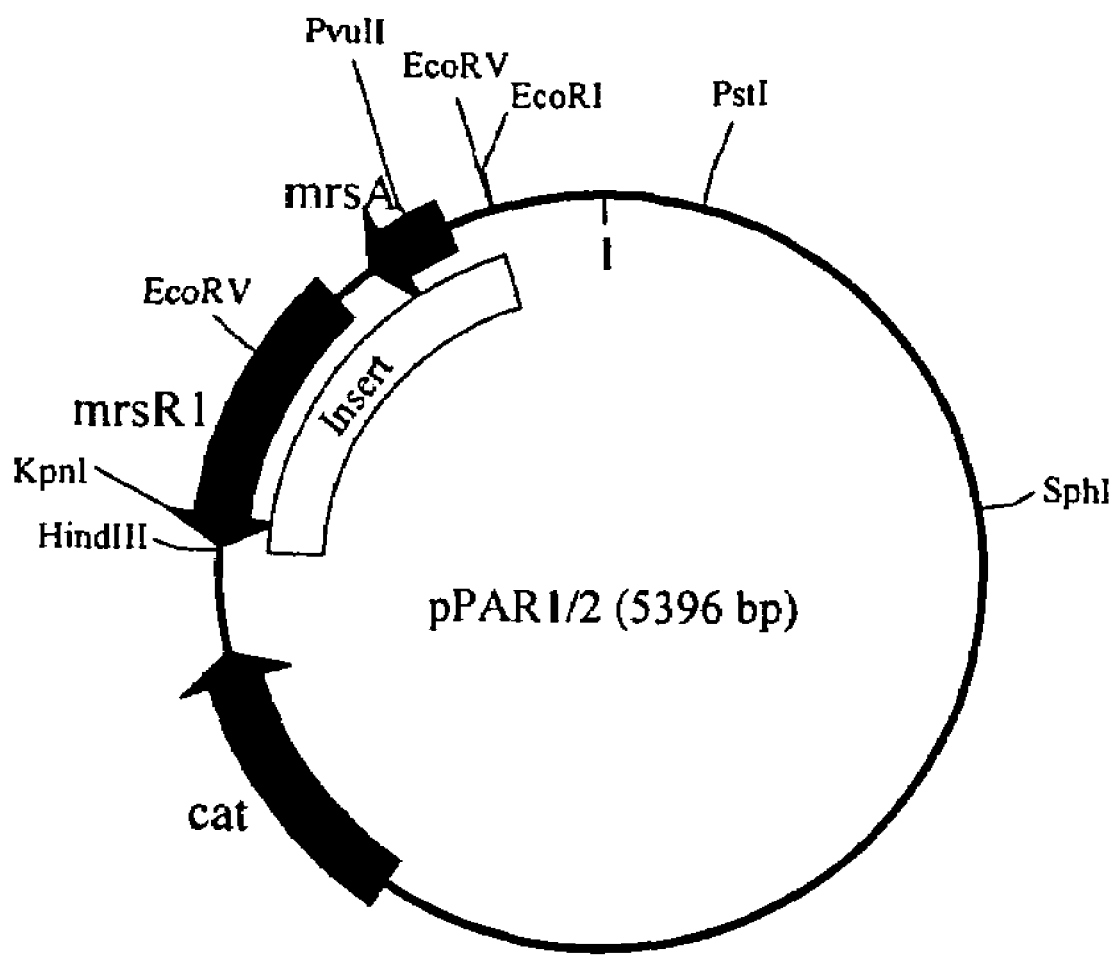
FIG. 7 shows a map of pPAR1/2.

Construction of pPAR1/2:

In order to test the effect of insertion of a plasmid harbouring a functional mrsR1 gene on the expression of mersacidin, the plasmid pPAR1/2 was constructed. Plasmid pPAR1/2 comprises mrsA, mrsR1 and the promoter of mrsA (see below) but not the EcoRI-EcoRV (putative operator) region upstream of mrsA in a temperature-sensitive insertion vector (pTV0mcs; Guder et al. Applied and Environmental Microbiology 68, 106-113; 2002). A map is shown in FIG. 7. The EcoRI site was introduced by the amplification primer 5'mrsAR1.

PCR of the mrsAmrsR1 region from the plasmid pMER1 (Altena et al., 2000) with the primers 5'mrsAR1 and 3'mrsAR1 yielded the expected product of 1078 bp.

Primer used for amplification of the insert (promoter, mrsA and mrsR1) of pMer2

| Primer | Sequence | Restriction site | $T_m$ |
|---|---|---|---|
| 5' mrsAR1 | 5' AGAAATATG<u>GAATTC</u>ATCTTAAGA CTCTTTATTTAAAC 3' (SEQ ID NO:27) | EcoRI | 61° C. |
| 3' mrsAR1 | 5' TTGGGTCAAGCTTTTTACACGAC 3' (SEQ ID NO:28) | HindIII | 59° C. |

PCR Conditions:

| Action | Temperature | Time | Cycle |
|---|---|---|---|
| Denaturation | 94° C. | 1 min | 1 |
| Denaturation | 94° C. | 30 sec | 30 |
| Annealing | 48° C. | 30 sec | |
| Extension | 72° C. | 1 min 30 sec | |
| Extension | 72° C. | 10 min | 1 |
| Cool | 4° C. | 10 min | 1 |

The fragment was purified by agarose gel electrophoresis employing MinElute Gel extraction kits (Qiagen, Hilden), digested with EcoR1 and HindIII and then ligated with the similarly digested temperature-sensitive plasmid pTV0mcs (Guder et al., 2002). The construct was used to transform *Staphylococcus carnosus* TM 300 protoplasts (according to Götz and Schuhmacher FEMS Microbiol. Lett. 40, 285-288; 1987) and the transformants were incubated at 30° C. The plasmid pPAR1/2 was then isolated from *Staphylococcus carnosus* TM 300 and used to transform protoplasts of the E17A mersacidin producer strain *Bacillus* HIL E17A (Szekat et al., 2003) according to Grosch and Wollweber (in Genetic Exchange, Streips et al. eds, pp. 97-105, Marcel Dekker Inc. 19821982). The variant E17A mersacidin does not show antibacterial activity and simplifies detection of production of mersacidin variants with antibacterial activity.

Figure 8:
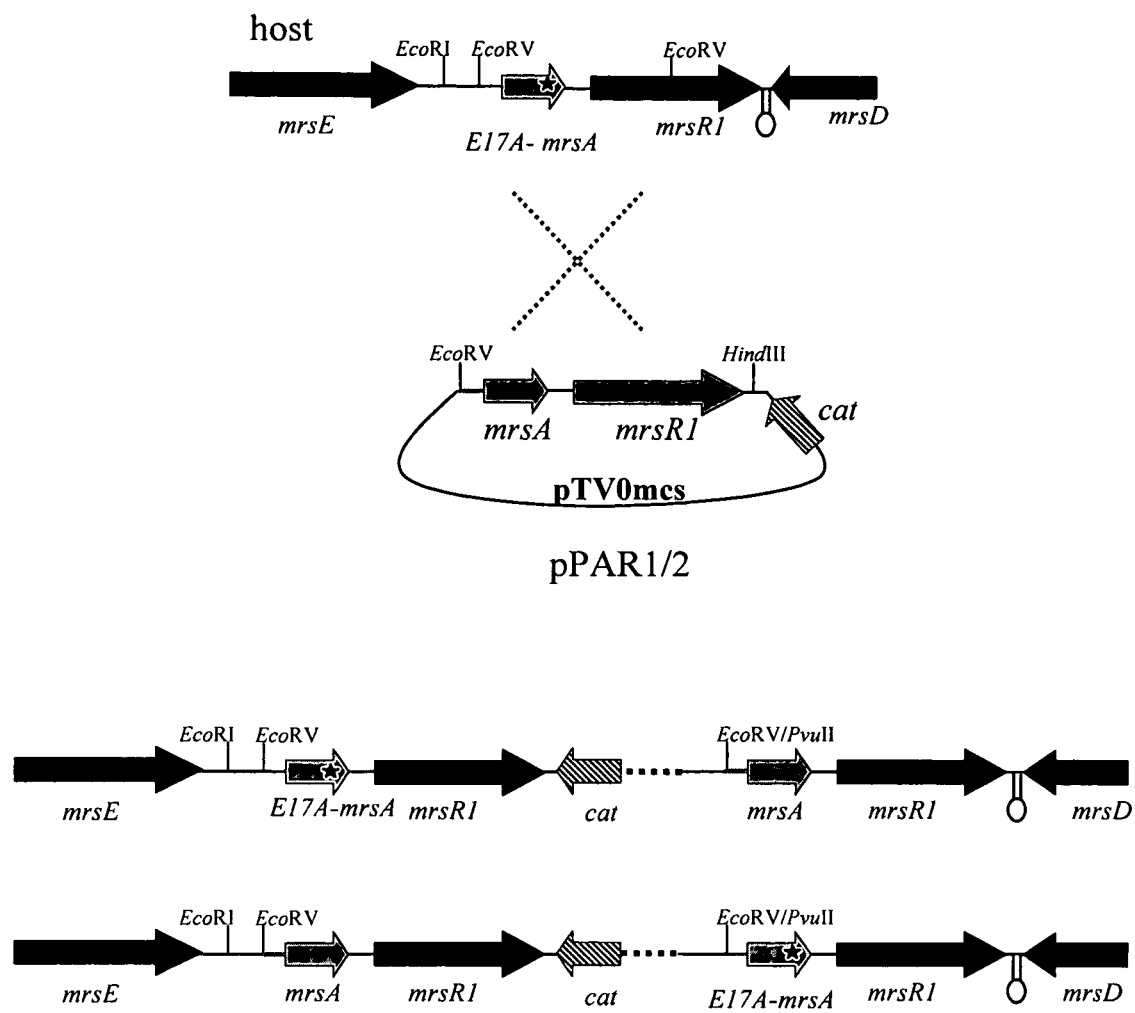
FIG. 8 shows insertion of pPAR1/2 into the mrs gene cluster. Insertion of pPAR1/2 into the gene cluster (top). The possible locations of the two copies of mrsA, E17AmrsA or the wildtype gene are shown.
Figure 10:
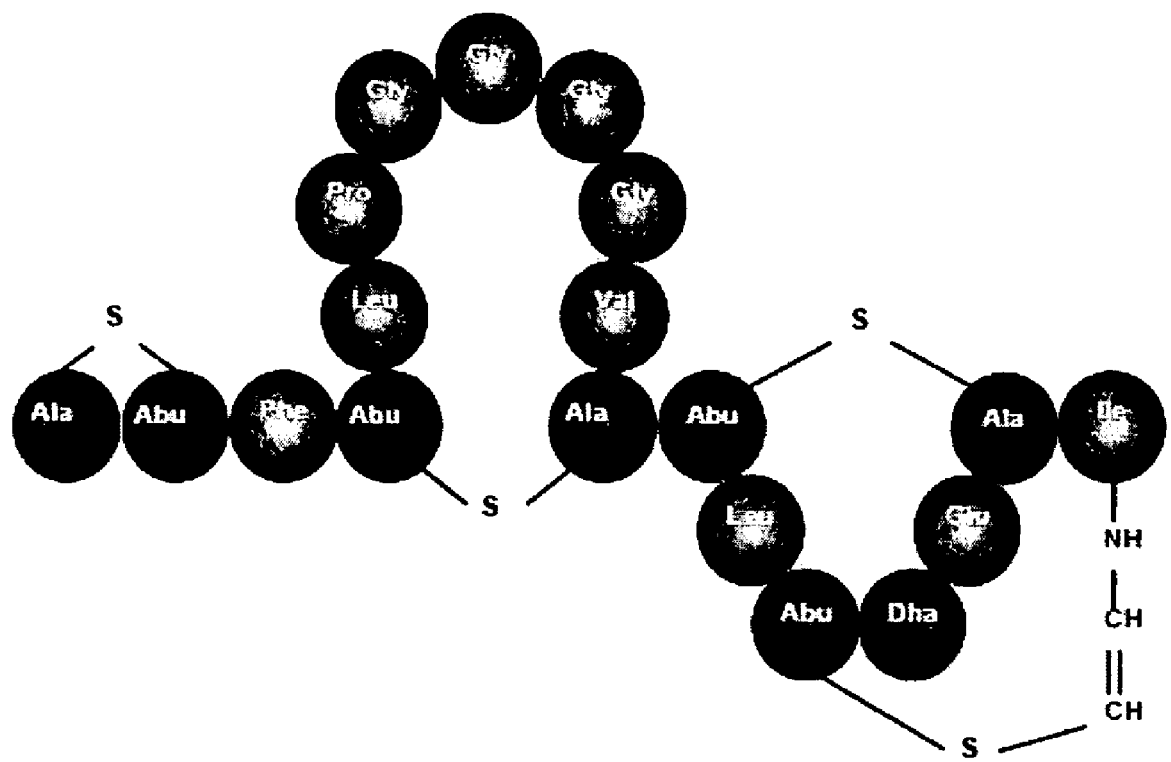
FIG. 10 shows the structure of mersacidin (SEQ ID NO:44). The compound is produced from 20 amino acids, 8 of which, including the Cterminal cysteine, are involved in lanthionine bridge formation. The compound includes the non-naturally occurring amino acids dehydroalanine (Dha) and [2-aminobutyric acid] (Abu), which are produced by post-translational modification of serine and threonine respectively. The 2-aminobutyric acid moieties are further combined with cysteine moieties to form thioether crosslinks known as methyllanthionines.

Integration of pPAR1/2 into the Chromosome of *Bacillus* HIL E17A:

Transformants were grown at 30° C. on tryptic soy agar containing chloramphenicol (20 mg/l). For integration of the plasmid into the chromosome, a preculture in tryptic soy broth plus chloramphenicol (20 mg/l) was carried out at 30° C. and 180 rpm. Diluted aliquots of this preculture were plated onto tryptic soy agar containing chloramphenicol (20 mg/l) and the plates were incubated at 42° C. to select clones that had integrated the plasmid into the chromosome. There are two possible points of integration for the plasmid so the location of the incoming wildtype gene depends on whether the cross over takes place upstream or downstream of the point mutation (T→G) that leads to the E17A exchange (FIG. 8). There are promoter regions in front of both structural genes, however the EcoRI-EcoRV region that might fulfil the role of an operator is only present upstream of the first (upstream) copy of the structural gene. It was therefore not clear, whether both copies would be transcribed.

The resulting colonies and the strains bearing the free plasmid were tested for production of active mersacidin and characterized by PCR:

Overnight cultures (1 ml tryptic soy broth plus 20 mg/l chloramphenicol at 42° C.) of each transformant were harvested and washed with sterile water. The pellet was resuspended in 0.1 ml water and 1 μl was used as template for PCR analysis. The templates were denatured for 10 min at 94° C. A competitive PCR using Taq polymerase (Qiagen, Hilden) and E17A Mut or E17A Umut as reverse primers and primer5', which anneals upstream of the EcoRI site on the chromosome as forward primer, was used to determine the location of the mutant and wild type gene (Szekat et al., 2003). The expected size of the PCR product is 509 bp.

Primers used for competitive PCR:

| Primer | Sequence | $T_m$ |
|---|---|---|
| E17A Mut | 5' CTATATAAATCAAATTAACAAATACATG-3' (SEQ ID NO:29) | 59.5 |
| E17A Umut | 5' CTATATAAATCAAATTAACAAATACATT-3' (SEQ ID NO:30) | 66 |
| primer5' | 5' GGGTATATGCGGTATAAACTTATG-3' (SEQ ID NO:31) | 66 |

PCR Conditions:

| Action | Temperature | Time | Cycle |
|---|---|---|---|
| Denaturation | 94° C. | 10 min | 1 |
| Denaturation | 94° C. | 1 min | 30 |
| Annealing | 59.5° C. | 30 sec | |
| Extension | 72° C. | 40 sec | |
| Extension | 72° C. | 10 min | 1 |
| Cool | 4° C. | 10 min | 1 |

The transformants were tested for the presence of free plasmid by PCR with the primer pair pTV0Ins-1 and pTV0Ins-2 using Taq polymerase (Qiagen, Hilden). The primers anneal with pTV0mcs and amplify a fragment of 1.2 kb that contains the insert and the neighbouring parts of the vector.

| Primer | Sequence | $T_m$ ° C. |
|---|---|---|
| pTV0Ins-1 | 5' GATTTACATATGAGTTATGCAG-3' (SEQ ID NO:32) | 50 |
| pTV0Ins-2 | 5' ACTACTATAACTGGTACTCGC-3' (SEQ ID NO:33) | 58 |

PCR Conditions:

| Action | Temperature | Time | Cycle |
|---|---|---|---|
| Denaturation | 94° C. | 10 min | 1 |
| Denaturation | 94° C. | 1 min | 30 |
| Annealing | 58° C. | 30 sec | |
| Extension | 72° C. | 1 min 30 sec | |
| Extension | 72° C. | 10 min | 1 |
| Cool | 4° C. | 10 min | 1 |

In order to determine whether multiple insertions had occurred, a long range PCR employing BIO-X-ACT long DNA-polymerase (Bioline, Luckenwalde) was performed with primer5' and 3'mrsD. Primer5' anneals upstream of the EcoRI site and primer 3'mrsD anneals in the 3' terminus of mrsD. The PCR product should comprise all of the inserted plasmid.

| Primer | Sequence | Temp ° C. |
|---|---|---|
| primer5' | 5' GGGTATATGCGGTATAAACTTATG-3' (SEQ ID NO:34) | 66 |
| 3' mrsD | 5' AAGAACAAAACACCCCTCAC-3' (SEQ ID NO:35) | 55.3 |

PCR Conditions:

| Action | Temperature | Time | Cycle |
|---|---|---|---|
| Denaturation | 94° C. | 10 min | 1 |
| Denaturation | 94° C. | 1 min | 10 |
| Annealing | 51° C. | 30 sec | |
| Extension | 68° C. | 15 min | |
| Denaturation | 94° C. | 1 min | 15 |
| Annealing | 51° C. | 30 sec | |
| Extension | 68° C. | 15 min 10 sec add/cycle | |
| Extension | 68° C. | 10 min | 1 |
| Cool | 4° C. | 10 min | 1 |

Antibacterial activity was tested after 72 h incubation in double strength production medium (Bierbaum et al. FEMS Microbiol. Lett. 127, 121-126). The supernatant was sterilised by filtration and 50 µl were plated on blood agar plates with *M. luteus* as indicator organism.

The following correlation was observed between mersacidin production and the nature of the construct:

| Construct | Inhibition zone |
|---|---|
| free plasmid | none |
| plasmid inserted, E17A gene in front position | as wild type producer |
| plasmid inserted, wild type gene in front position | large zones |

Where inhibition zones were detected production of wild type mersacidin was confirmed by hplc-MS:

| | |
|---|---|
| Column: | Phenomenex Luna C18(2) 150 × 4.6 mm 3µ |
| Flow rate: | 1 ml/min |
| Mobile phase: | A 10% acetonitrile, 0.1% formic acid 90% water |
| | B 90% acetonitrile, 0.1% formic acid, 90% water |
| | Linear gradient A to B over 10 minutes, hold 1 min, B → A |
| Wavelength: | 200-400 nm |
| Injection volume: | 10 µl |
| Post column split: | 1:10 |
| Mass spectrometer: | Micromass Platform LC |
| Mode: | Electrospray positive |
| Nitrogen flow: | 380 l/hr |
| Capillary voltage: | 3.15 KV |
| Cone voltage: | 40 V |
| Skimmer lens offset: | 5 V |

Mersacidin was detected as a doubly charged ion m/z=913 $(M+2H)^{2+}$, together with its sodium and potassium adducts m/z=924 $(M+H+Na)^{2+}$, m/z=932 $(M+H+K)^{2+}$.

These results indicate that the wild type mrsA gene was expressed after integration in the upstream or downstream position. There was no production of antibacterial activity when the plasmid was autonomous (i.e. not integrated into the chromosome). One clone (number 2, which produced a large inhibition zone) was characterised further using long range PCR covering the region where the insertion had taken place. All colonies tested gave the expected 6.7 kb band corresponding to a single insertion, as well as a 12.1 kb band, indicating a double integration and a small band (1.3 kb) corresponding to the intact mersacidin biosynthetic gene cluster.

This example illustrates complementation by this approach, and may also be used for the production of mersacidin derivatives. The approach based on the plasmid used herein would also complement the mrsA knockout strain rec1 (Altena et al. 2000) which would be beneficial as there would be no background lantibiotic at all. Because the rec1 strain has had the mrsA gene inactivated by replacement of the gene by the erm gene, the presence of the mrsR1 gene on the plasmid used is required due to the "polar" effect of the mrsA lesion in rec1—in other words, it is believed that the mrsR1 gene is produced by read-through of a transcript from the mrsA gene and that by disrupting the mrsA in this way there is no read through into the mrsR1 gene.

EXAMPLE 6

Construction of *Bacillus* HIL mrsA E4stop

An alternative means to provide a *Bacillus* ΔMrsA of the invention is illustrated by this example, in which a stop codon is introduced into the mrsA gene by homologous recombination.

Construction of Plasmid pAE4stop

For construction of *Bacillus* HIL mrsA E4stop a stop codon was introduced into the mrsA gene by substituting the DNA encoding the fourth amino acid of mrsA for a TAA codon. This mutation was introduced using the method described by Szekat et al., 2003. A plasmid for mutagenesis was created by subcloning the 1.1 kb EcoRI-KpnI fragment that harbours mrsA and nearly all of mrsR1 into the pALTER-1 vector of the Altered Sites in vitro Mutagenesis System (Promega). Single strand DNA of the recombinant plasmid was purified and used for the synthesis of the second strand. The mutation was introduced by using the mutagenic oligonucleotide GAATACA ATG AGT CAA TAA GCT ATC ATT CGT T (SEQ ID NO:36) as primer. The exchange, that introduces the stop codon, has been printed in bold. A second primer (provided in the mutagenesis kit) repairs a mutation in the ampicillin resistance gene of the vector which serves as a selection marker. The mutagenesis reaction was used to transform *E. coli* JM109. Plasmids obtained from *E. coli* JM109 were sequenced to verify that the mutant gene was created. The plasmid with the expected sequence was called pIN1.

The mutant mrsA gene with the exchange E4stop was then amplified from pIN1 by PCR. The following primers were used for amplification:

pIN1HIN: GGC <u>GAATTC</u>GAG ACA AGG TAA AC (SEQ ID NO:37; the natural Eco RI site upstream of mrsA is underlined, the GGC is sequence of pALTER-1).

pIN1RÜCK: TTT <u>CTGCAG</u> AGA ATT TTC TAA TAG TTT ATA TAA (SEQ ID NO:38; the undelined PstI site was introduced for cloning and is not present in the original sequence).

The amplified 652 bp fragment covers the operator and promoter region of mrsA, mrsA-E4stop and the downstream region of mrsA and ends just 4 bp upstream of the ribosome binding site of mrsR1. This fragment was digested with EcoRI/PstI and ligated to pBT2 previously digested with EcoRI/PstI, the ligation mixture was used to transform *E. coli* SCS110. Ampicillin resistant colonies were obtained and plasmid was isolated. Plasmids were characterised by restriction analysis and the plasmid with the expected restriction pattern was selected. The recombinant plasmid pAE4stop was then sequenced in order to verify that the mutation was present and that no other exchanges had occurred.

Generation of *Bacillus* HIL mrsA E4stop.

Plasmid pAE4stop was introduced into *Bacillus* HIL by electroporation. The transformation mixture was plated on Luria Agar containing chloramphenicol (20 mg/l) and the plates were incubated at 30° C. to allow replication of the (temperature sensitive) vector. The recombinant *Bacillus* HIL/pAE4stop was then plated on tryptone soy agar containing chloramphenicol (20 mg/l) and incubated at 42° C. in order to select integrants of pAE4stop into the chromosome. Integration in *Bacillus* HIL/pAE4stop was monitored by PCR using the primers:

```
pBT2reverse:
5' CCT GAC TGC GTT AGC AAT TTA ACT    (SEQ ID NO:39)
GTG 3'

Primer 5':
5' GGG TAT ATG CGG TAT AAA CTT ATG    (SEQ ID NO:40)
3'
```

The integrant *Bacillus* HIL/pAE4stop was cultured for at least 100 generations at 42° C. in the absence of chloramphenicol in order to obtain strains that had performed the second cross over. A 10% glycerol stock was made from this culture and used to obtain isolated colonies for identification of possible double recombinants. Approximately 10000 colonies were tested for growth on tryptic soy agar containing chloramphenicol (20 mg/l) and stored on nutrient agar. Colonies that didn't grow on chloramphenicol containing agar after incubation for 48 h were tested for mersacidin production. Six out of thirteen tested colonies did not produce antibacterial activity. Chromosomal DNA of this strains was prepared and analysed by competitive PCR using the primers:

```
MutE4stop    5' GGG GTG AAT ACA ATG    (SEQ ID NO:41)
             AGT CAA T3'

UmutE4stop   5' GGG GTG AAT ACA ATG    (SEQ ID NO:42)
             AGT CAA G 3'

RT5          5' ATT AAC AAA TAC ATT    (SEQ ID NO:43)
             CAG AAG TTA GAG TAC 3'
```

Two clones carrying E4stop-mrsA gene were identified and verified by DNA sequencing. One of these clones carrying the E4stop mutation in mrsA was selected and called *Bacillus* HIL mrsA E4stop.

EXAMPLE 7

Expression of Mersacidins in *Bacillus* HIL mrsA E4stop

The plasmids pNB018 (contains wild-type mrsA; see example 3), pNB2024 (contains F3W mutant mrsA; see example 4) and pNB2026 (contains G8A mutant mrsA; see example 4) were introduced into *E. coli* dam dcm strain ET12567 by electroporation. Ampicillin resistant colonies were selected, plasmid DNA was prepared using the Promega Wizard miniprep kit and concentrated by ethanol precipitation. These plasmid preparations were used to transform electrocompetent cells of *Bacillus* sp. HIL mrsA E4stop by the method described in Example 10 below.

Two transformants from each plasmid were selected and streaked to L Agar containing 20 mg/l chloramphenicol and incubated at 30° C. for 24 hours. A loopful of growth was used from each to inoculate 3 ml of tryptic soy broth containing 20 mg/l chloramphenicol in a 15 ml culture tube. These seed cultures were incubated at 30° C. with shaking at 250 rpm for 24 hours, 0.5 ml of each culture was used to inoculate 10 ml of production medium (2×BPM+300 mM glucose) containing 20 mg/l chloramphenicol in 50 ml conical flasks, which were incubated at 30° C. with shaking at 250 rpm for five days. The cultures were analysed for production of mersacidin or the appropriate variants. Samples of the cultures (1 ml) were centrifuged at 14000 rpm for 10 minutes. Supernatants were decanted and used undiluted for HPLC-MS, and bioassay. These data showed that in supernatants of *Bacillus* sp. HIL ΔmrsA E4stop/pNB018, mersacidin was produced at a concentration comparable to the wild type *Bacillus* sp. HIL. In supernatants of *Bacillus* sp. HIL ΔmrsA E4stop/pNB2024, the mersacidin variant F3W was produced at a concentration comparable to the wild type *Bacillus* sp. HIL, and in supernatants of *Bacillus* sp. HIL ΔmrsA E4stop/pNB2026 the mersacidin variant G8A was produced at a concentration comparable to the wild type *Bacillus* sp. HIL.

EXAMPLE 8

Isolation of Mersacidin F3W

Growth Conditions

*Bacillus* sp.ΔmrsA E4stop/pNB2024 was inoculated from a single colony on *Luria Agar* containing chloramphenicol (20 mg/l) into 50 ml tryptic soy broth containing chloramphenicol (20 mg/l) in a 250 ml conical flask and incubated at 30° C. and 250 rpm. After 24 hours, 4×10 ml of this culture were used to inoculate 4×500 ml of 2× BPM+300 mM glucose containing chloramphenicol (20 mg/l) in 4×2 litres conical flasks, and the cultures were incubated for 5 days at 30° C. and 200 rpm.

Harvesting

After five days growth, the cultures were harvested by centrifugation at 4000 rpm and 4° C. for 30 minutes. The supertant was decanted and stored for further analysis and the cell pellet was discarded.

Isolation

Diaion HP20 (70 g) (Supelco) was suspended in 150 ml of methanol, mixed by swirling and left for 20 minutes. Methanol was decanted, the resin was suspended in 150 ml of water by swirling and left for 20 minutes. Water was decanted and the resin was suspended in 600 ml of water. The resin was collected in bond elut reservoirs (PK/100 60 ml, Varian) and excess water flushed through by passing air via a syringe.

Conditioned diaion HP20 resin (76 g) was added to 1840 ml of culture broth, mixed by swirling and left overnight at 4° C. The Broth-Diaion HP20 mixture was dispensed into three bond elute reservoirs (60 ml reservoir, Varian), the resin was washed with four bed volumes of water; three bed volumes of each of 25, 50, 75 and 100% methanol and samples of each fraction were taken for HPLC analysis. Fractions containing mersacidin F3W (75-100% methanol) were pooled and concentrated using a rotary evaporator from 1 litre to 325 ml (approx.50% MeOH).

Reverse phase chromatography was carried out using two C18 Bond Elut columns (Mega BE-C18, 10 ml, Varian ). The columns were conditioned with two bed volumes of 100% methanol followed by 1.5 bed volumes of water. The concentrate containing mersacidin F3W was loaded evenly onto the two columns. The columns were eluted in sequence with two bed volumes of 50%, 75% and 100% methanol. Finally the columns were washed by addition of a further two bed volumes of methanol. Samples were taken from each fraction for HPLC analysis. Fractions containing significant amounts of mersacidin F3W were pooled and concentrated by evaporation to 50-60 ml.

Cation Exchange chromatography was carried out using four 1 g columns of SCX Bond Elut (Varian). The columns were conditioned by equilibrating with 1.5 bed volumes of 100% methanol followed by one bed volume of 40 mM potassium phosphate buffer pH 2.0 in 50% methanol. The concentrate containing mersacidin F3W was mixed 1:1 with 40 mM potassium phosphate buffer pH 2.0 in 50% methanol, loaded evenly onto the 4 columns and the flow through was collected. The column was eluted sequentially with one bed volume of 40 mM potassium phosphate buffer pH 2.0 in 50% methanol. Mersacidin F3W was eluted with two bed volumes of 250 mM potassium phosphate buffer pH 7.0 in 50% methanol. The eluate was concentrated by evaporation.

Preparative HPLC was used for purification of mersacidin F3W, the conditions were as follows:

| | |
|---|---|
| Column | Capitol HPLC Ltd C18 - BDS - HL5 - 26052 15 cm × 20 mm |
| Solvent A | 30% ACN in 20 mM KPi pH 7.0 |
| Solvent B | 65% ACN in 20 mM KPi pH 7.0 |
| Detection | 268 nm |
| Injection Vol. | 1 ml |
| Flow Rate | 10 ml/min |
| T = 0 min | 100% A |
| T = 1 min | 100% A |
| T = 20 min | 100% B |
| T = 25 min | 100% B |
| T = 26 min | 100% A |
| T = 30 min | 100% A |
| Collection | Start 8 min; End 20 min; 1 min fractions |

Fractions containing significant amounts of mersacidin F3W (retention time=12-14 min) were pooled and concentrated by evaporation.

After preparative HPLC the sample was desalted using a C18 bond elut column (1 g)(Varian). The column was conditioned with two bed volumes of 100% methanol followed by 1.5 bed volumes of water. The concentrate containing mersacidin F3W was loaded onto the column and the column was eluted in sequence with two bed volumes of 50% methanol and 2-3 bed volumes of 100% methanol. Samples were taken from each fraction for HPLC analysis. Fractions from the elution with 100% methanol were evaporated to give mersacidin F3W (m/z=933.5 $(M+2H)^{2+}$; m/z=944 $(M+H+Na)^{2+}$)

EXAMPLE 9

SigH Deletion of *Bacillus* HIL mrsA E4stop

Protoplasts from *Bacillus* HIL ΔmrsA E4stop were prepared according to Szekat et al., 2003 and transformed with plasmid pNB029 (see Example 2). Chloramphenicol resistant colonies were transferred to tryptic soy agar containing chloramphenicol (20 mg/l) and grown at 30° C. for 24 h. For integration of the plasmid into the chromosome, a preculture in tryptic soy broth plus chloramphenicol (20 mg/l) was carried out at 30° C. and 200 rpm. Diluted aliquots of this preculture were plated onto tryptic soy agar containing chloramphenicol (20 mg/l) and the plates were incubated at 42° C. to select clones that had integrated the plasmid into the chromosome. One colony was selected and grown at 42° C. and 200 rpm on tryptic soy broth containing chloramphenicol (20 mg/l) for 24 hours. Serial dilutions of this culture were plated on tryptic soy agar containing chloramphenicol (20 mg/l) to obtain isolated colonies which have pNB029 integrated into the chromosome of Bacillus HIL ΔmrsA. One colony was selected and grown at 42° C. and 200 rpm on 50 ml of tryptic soy broth, after 12 h of growth, 0.05 ml of this culture were transferred to 50 ml of tryptic soy broth and grown in the same conditions of the previous culture, 5 consecutive subcultures were carried out and samples of the sixth subculture were titrated and frozen. Colonies from this culture were grown on tryptic soy agar at 30° C. for 24 h and replicated into tryptic soy agar containing chloramphenicol (20 mg/l). Chloramphenicol sensitive colonies were isolated and chromosomal DNA was prepared. DNA samples were analysed by PCR and the colonies that have a deletion in sigH were isolated.

EXAMPLE 10

Transformation by Electroporation

The only published methods for the introduction of DNA into Bacillus sp. HIL, the producer of mersacidin, involve protoplast transformation and the use of an intermediate host, Staphylococcus carnosus (eg Szekat, C. et al. Applied and Environmental Microbiology 69, 3777-3783; 2003).

In the published work plasmids for genetic manipulation of Bacillus HIL were constructed in the general cloning host Escherichia coli and then introduced by protoplast transformation into S. carnosus. The authors found that plasmids could not be transformed directly into HIL Y-85,54728 using DNA prepared from E.coli, but that it was necessary to use S.carnosus as an intermediate host (unpublished results). Plasmid DNA prepared from S.carnosus transformants was introduced into Bacillus HIL by protoplast transformation. Each transformation gave from 0 to 10 transformants per experiment. This procedure is laborious and time-consuming, and the number of transformants generated is very low.

In addition to protoplast transformation, electroporation has been used extensively as a means of transforming a wide variety of microorganisms including Bacillus species. Electroporation is generally considered to be a more convenient method of transformation than protoplast transformation. It has been demonstrated that using high osmolarity in the growth, electroporation and recovery media increases transformation efficiency for plasmid DNA in Bacillus subtilis and Bacillus licheniformis (Xue, G-P et al. Journal of Microbiological Methods 34, 183-191; 1999). There have been no reports of electroporation of Bacillus HIL.

A procedure has been developed for transformation of Bacillus HIL using electroporation of plasmid DNA prepared from strains of E.coli. This involved preparing plasmid DNA for transformation from E.coli strains deficient in DNA methylases, ie dam dcm mutants. In contrast to the procedure used by Xue et al, which gave no transformants of Bacillus HIL, electroporation was achieved by using DNA prepared from S. carnosus or E.coli dam dcm strains, and altering the media and conditions used for growth and electroporation of the Bacillus strain. Using the procedure of the invention, 100-1,000 transformants could be generated in a single electroporation, using DNA prepared directly from E.coli without the need of an intermediate host. This represents a much more efficient and convenient method for transformation.

Preparation of Plasmid DNA

The Gram-positive/E.coli shuttle vector pCU1 (Augustin, J. et al (1992), European Journal of Biochemistry 204, p1149-1154) was introduced into chemically-competent E.coli BL21* (DE3) cells obtained from Invitrogen. This strain carries dam and dcm mutations. Transformants were selected on L agar containing 100 μg/ml ampicillin. A transformant was picked and used to inoculate 10 ml of L broth. This culture was grown at 37° C. for approximately 16 hours with shaking at 250 rpm. The culture was centifuged at 10,000 rpm for 10 minutes and the pellet resuspended in 750 μl of resuspension buffer. This suspension was divided into 3 eppendorf tubes and plasmid DNA was prepared using the Promega Wizard mini-prep plasmid isolation kit using the manufacturer's instructions. Plasmid DNA was recovered in 300 μl sterile de-ionised water, concentrated by ethanol precipitation and re-dissolved in 25 μl of sterile water. 1.5 μl of this DNA was used to electroporate 60 μl of an electrocompetent cell suspension of Bacillus HIL.

Preparation of Electrocompetent Cells of HIL Y-85,54728.

A frozen cell suspension of Bacillus HIL(maintained at −80° C. in 10% glycerol) was used to inoculate 10 ml of L broth and the culture was incubated at 30° C. with shaking (250 rpm) for approximately 16 hours. 3.125 ml of this culture was used to inoculate 50 ml of tryptic soy broth supplemented with sorbitol and mannitol (both to 0.5M) in a 250 ml conical flask. This culture was shaken at 250 rpm at 30° C. for 4.5 hours (reaching an OD at 600 nm of approximately 2.0) then cooled on ice for 10 mins before centrifuging at 2,500 rpm for 30 minutes. The pellet was resuspended in 6 ml of ice-cold electroporation medium (10% glycerol in 1M sorbitol, 0.75M mannitol) and then centrifuged for 3 minutes at 12,000 rpm. The cells were washed another three times in 3 ml ice-cold electroporation medium (with centrifugation for 3 mins at 12,000 rpm) before finally resuspending in 1 ml of ice-cold electroporation medium. 60 μl aliquots were used for electroporation, either immediately or after storage at −80° C. (and thawing on ice).

Electroporation of Bacillus HIL.

1.5 μl of plasmid DNA was added to 60 μl of ice-cold electrocompetent cells, mixed, and transferred to a pre-cooled electroporation cuvette with a 1 mm gap. The voltage used for electroporation was 2500V on an electroporator preset for capacitance (10 μF) and resistance (600Ω). Time constants were typically in the range of 3-6. Immediately following electroporation, 1 ml of recovery medium was added (tryptic soy broth supplemented with sorbitol to 1M and mannitol to 0.75M), mixed, then the suspension was transferred to an eppendorf tube and incubated at 30° C. for 3 hours in a waterbath. Following recovery the suspension was centrifuged at 12,000 rpm for 3 minutes, the pellet was resuspended in 200 μl tryptic soy broth and then plated on L agar containing 20 μg/ml chloramphenicol to select for transformants. Typically, approximately 1,000 transformants were obtained in each electroporation.

Electroporation using Plasmid DNA from Methylating E.coli Strains or from Staphylococcus carnosus.

The electroporation method given by Xue, G-P et al. (Journal of Microbiological Methods 34, 183-191; 1999) when initially tested with Bacillus HIL and Bacillus subtilis 168 (the commonly-used laboratory strain of B. subtilis) gave a modest number of transformants with B. subtilis 168 in our hands, but none with Bacillus HIL. A number of modifications were made to the method which improved electroporation efficiencies in B. subtilis 168, but not Bacillus HIL.

In one experiment, cells were prepared from both strains. The basic method was similar to that described above, but with the following differences:

The growth medium used was L-broth containing 0.5M sorbitol

The electroporation medium comprised 0.5M sorbitol, 0.5M mannitol and 10% glycerol The recovery medium was L-broth containing 1M sorbitol and 0.75M mannitol Cells were grown for 4.5 hours and prepared and electroporated as before, with 1.5 µl of pCU1 prepared from *E.coli* DH10B. A total of 505 transformants were obtained from *B.subtilis* 168, but none from *Bacillus* HIL.

Electroporation of *Bacillus* HIL was also attempted using plasmid prepared from *Staphylococcus carnosus*. In this experiment the method was as used above, except that the electroporation medium consisted of 1M sorbitol, 0.75M mannitol and 10% glycerol. Two plasmid preps were used, pCU1 prepared from *E.coli* DH10B, as above, and pTVOmcs prepared from *S.carnosus*. pTVOmcs is a Gram-positive vector which cannot replicate in *E.coli* (Guder, A. et al. (2002), Applied and Environmental Microbiology 68, p. 106-113). No transformants were obtained from pCU1, but 406 transformants were obtained from pTVOmcs. This is taken as further indication that the methylated DNA from *E.coli* DH10B is restricted by a methylation-specific system in *Bacillus* HIL, but that *S.carnosus*-prepared DNA is not methylated and therefore gives a much higher transformation frequency.

EXAMPLE 11

Production of Mersacidin Variants.

Bioactive Mersacidin Variants

Site-directed mutagenesis of mersacidin may be performed using methods known per se in the art, e.g. as disclosed by Szekat et al, ibid. Mersacidin variants having antibacterial activity as determined by a bioassay using agar plates containing *Micrococcus luteus* ATCC 4698 as indicator strain were made.

These variants are set out in Table 1:

inoculate 10 ml of 2×BPM supplemented with chloramphenicol (25 mg/L) in a 50 ml conical flask. Mersacidin variants production was assessed after 5 days incubation at 30° C. and 250 rpm. Fermentation samples were spun down at 4000 rpm for 10 min in 15 ml centrifuge tubes. The supernatants were transferred to 50 ml centrifuge tubes containing 100 mg of conditioned resin Diaion HP-20 (Supelco). After incubation at room temperature for 6 hours with shaking, the supernatants were discarded and the resin containing the mersacidin variant was washed with 2×10 ml of water. A second washing step was carried out with 2×10 ml of methanol:water (1:1). Mersacidin variants were eluted from the resins with 1 ml of 100% methanol. The eluates were evaporated to dryness and resuspended in 0.250 ml of methanol:water (1:1) and analysed by LC-MS, HPLC and bioassay.

Fermentation broth samples and/or the concentrated resin eluates were transferred to HPLC vials and 20 µl of each sample was analysed by LC-MS using the HPLC gradient conditions listed in Table 5 and the mass spectrometry conditions listed in Table 6. Prior to bioassay of the components in broth samples and fermentation concentrate, samples were fractionated using an analytical HPLC coupled to a 96 well microtitre plate fraction collector. In general, 0.2 ml of broth sample or fermentation concentrate was loaded onto the column and the components were resolved and collected as described in Table 7. The fractions in the 96 well microtitre plates were evaporated to dryness and the resulting residues were dissolved in 50 µl of methanol:water (1:1). For each variant the resuspended residues from fractions 36 to 43 were loaded onto bioassay agar plates containing *Micrococcus luteus* ATCC 4698 as indicator strain. The bioassay plates containing the mersacidin variant samples were left at room temperature for 1 hour to allow diffusion of the sample into the agar prior to incubation at 30° C. overnight.

TABLE 5

HPLC conditions used in the analysis of broth samples and fermentation concentrate samples by LC-MS

| Column | Phenomenex Luna HPLC column (5µ, C18(C2), 150 × 4.6 mm) |
|---|---|
| Mobile Phase A | 10% Acetonitrile/0.1% Formic Acid |

TABLE 1

| F3 | L5 | P6 | G7 | G8 | G9 | G10 | V11 | L14 | Dha16 |
|---|---|---|---|---|---|---|---|---|---|
| F3D | L5A | P6H | G7A | G8A | G9A | G10A | V11L | L14V | Dha16G |
| F3R | L5I | P6A | G7N | G8C | G9S | G10V | V11I | L14I | Dha16A |
| F3W | L5M | P6N | G7Q | G8N | G9T | G10S | V11M | L14M | Dha16Dhb |
| F3I | L5N | P6Q | G7W | G8Q | G9N | G10Dha | V11K | | Dha16H |
| F3P | L5H | P6V | G7S | G8H | G9R | G10M | V11C | | |
| F3S | | P6M | G7T | G8E | G9Y | G10Y | | | |
| F3C | | P6F | G7M | G8I | G9H | G10W | | | |
| F3M | | P6Y | G7I | G8S | G9Q | G10I | | | |
| F3N | | P6G | G7H | G8P | G9L | G10Dhb | | | |
| F3H | | P6L | G7F | | | G10R | | | |
| | | P6I | | | | G10K | | | |
| | | P6D | | | | G10H | | | |
| | | P6E | | | | G10N | | | |

Expression and Analysis of Variants in *Bacillus* HIL ΔmrsA:

After four days incubation at 30° C., four random colonies obtained from each transformation were tested for production of the respective mersacidin variant. Seed cultures were carried out by growing the colonies in a 15 ml centrifuge tube (Falcon) containing 3 ml of Tryptic Soy Broth supplemented with chloramphenicol (25 mg/L). After 24 hours incubation at 30° C. and 250 rpm, 0.5 ml of the seed culture was used to TABLE 5-continued HPLC conditions used in the analysis of broth samples and fermentation concentrate samples by LC-MS

| Mobile Phase B | 90% Acetonitrile/0.1% Formic Acid |
|---|---|
| Flow Rate | 1 ml/min |

TABLE 5-continued

HPLC conditions used in the analysis of broth samples
and fermentation concentrate samples by LC-MS

| Gradient | Time 0 minutes | 100% A | 0% B |
|---|---|---|---|
| | Time 10 minutes | 0% A | 100% B |
| | Time 11 minutes | 0% A | 100% B |
| | Time 11.1 minutes | 100% A | 0% B |
| | Time 15 minutes | 100% A | 0% B |
| | Cycle time 15 minutes | | |

TABLE 6

Mass Spectrometer Parameters used in the analysis of
broth samples and fermentation concentrate by LC-MS

| Ionisation | Electrospray + ve mode |
|---|---|
| Mass Range | 250 to 1500 m/z |
| Capillary Voltage | 3.10 KV |
| Cone Voltage | 40 V |
| Skimmer Lens Offset | 5 V |
| Ion Energy | 1.4 |

TABLE 7

Analytical HPLC conditions used to fractionate
broth samples and fermentation concentrate:

| Column | Phenomenex Luna HPLC column (3µ, C18(C2), 150 × 4.6 mm) | | |
|---|---|---|---|
| Mobile Phase A | 30% Acetonitrile | | |
| Mobile Phase B | 65% Acetonitrile | | |
| Flow Rate | 1 ml/min | | |
| Gradient | Time 0 minutes | 100% A | 0% B |
| | Time 10 minutes | 0% A | 100% B |
| | Time 11 minutes | 0% A | 100% B |
| | Time 11.2 minutes | 100% A | 0% B |
| | Time 15 minutes | 100% A | 0% B |
| | Cycle time 15 minutes | | |
| Injection Volume | 200 µl | | |
| Detection | 254 and 210 nm | | |
| Fraction Collection | 0.2 min/fraction | | |
| Fractions Collected | 60 fractions | | |

EXAMPLE 12

MIC Data for Isolated Mersacidin Variants

A selection of the variants produced in Example 1 above were tested further for activity against a range of bacteria. Minimum inhibitory concentrations (MICs) for all organisms with the exception of *Streptococcus pneumoniae* were determined by two-fold serial antibiotic dilutions in Mueller-Hinton broth (MHB) supplemented with 50 µg/ml calcium as calcium chloride dihydrate. Minimum inhibitory concentrations (MICs) for *S. pneumoniae* were determined by two-fold serial antibiotic dilutions in Brain Heart Infusion (BHI) broth supplemented with 50 µg/ml calcium as calcium chloride dihydrate. Antimicrobial agent stock solutions were prepared and stored according to NCCLS standard M7-A6.

Actively growing broth cultures were diluted to contain $10^5$ to $10^6$ CFU/ml by adjusting to an absorbance of 0.2-0.3 at 600 nm, equivalent to the McFarland 0.5 standard. They were then diluted a further 1:100 in broth. The assays were performed in duplicate in sterile 96-well microtitre plates in a total volume of 200 µl (160 µl broth, 20 µl antibiotic, 20 µl inoculum) in a concentration range from 64 µg/ml to 0.06 µg/ml. The $12^{th}$ well of the microtitre plate contained no antimicrobial agent. Vancomycin was used as a reference antibiotic for quality control. Plates were incubated aerobically, shaking, for 18-20 hours at 37° C. with the MIC defined as the lowest concentration of drug that produced no visible growth.

The results for the variants F3W, G7N, G8N, G8Q, G9H, G9A, G9S, G10V, G10Y, V11I, V11L, V11M, L14M, L14V, S16G, Dha16Dhb, Dha16A, L14I, G10A, G10N, G9R, G9N, P6H and G7A are set out in Tables 8A and 8B below (figures in µg/ml):

TABLE 8A

| Compound | E. faecium 7131121 | E. faecium 19579 | E. faecalis 29212 | S. aureus R33 | S. aureus SH1000 |
|---|---|---|---|---|---|
| G7N | | 64, 64 | >64, >64 | 32, 16 | 64, 64 |
| G8N | | >64, >64 | >64, >64 | 16, 32 | >64, >64 |
| G9H | | 64, 64 | >64, >64 | 16, 8 | 32, 32 |
| G9A | | 64, 64 | >64, >64 | 8, 8 | 32, 32 |
| G10V | | >64, >64 | >64, >64 | >64, >64 | >64, >64 |
| G10Y | | 64, 64 | 32, 32 | 64, 64 | >64, >64 |
| Dha16G | 64, 64 | 32, 32 | 64, 64 | 16, 16 | 32, 32 |
| V11M | 64, 64 | 32, 32 | 64, 64 | 32, 32 | 64, 64 |
| L14M | 64, 64 | 64, 64 | 64, 64 | 16, 16 | 32, 32 |
| L14V | >64, >64 | 64, 64 | 64, 64 | 16, 16 | 32, 32 |
| Dha16Dhb | 64, 64 | | 32, 32 | 8, 8 | 32, 32 |
| V11I | 16, 16 | | 16, 16 | 16, 16 | 32, 32 |
| F3W | 34, 34 | 8.5, 8.5 | 8.5, 17 | 8.5, 8.5 | 17, 34 |
| G9S | >64, >64 | >64, >64 | >64, >64 | >64, >64 | >64, >64 |
| G8Q | >64, >64 | >64, >64 | >64, >64 | 32, 32 | >64, >64 |
| V11L | 32, 32 | 32, 32 | 64, 32 | 16, 16 | 64, 64 |
| Dha16A | 64, 64 | 32, 32 | 64, 64 | 32, 16 | 32, 32 |
| L14I | 32, 64 | 16, 16 | 32, 32 | 8, 8 | 32, 32 |
| G10A | >64, >64 | >64, >64 | >64, >64 | >64, >64 | >64, >64 |
| G10N | >64, >64 | >64, >64 | >64, >64 | >64, >64 | >64, >64 |
| G9R | >64, >64 | >64, >64 | >64, >64 | >64, >64 | >64, >64 |
| G9N | >64, >64 | >64, >64 | >64, >64 | 64, >64 | >64, >64 |
| P6H | >64, >64 | >64, >64 | >64, >64 | 32, 64 | 64, 64 |
| G7A | >64, >64 | 64, 64 | >64, >64 | 32, 64 | >64, >64 |
| Mersacidin | 64, 32 | 32, 16 | 32, 32 | 16, 16 | 32, 32 |

TABLE 8B

| Compound | S. epidermidis 11047 | M. luteus 4698 | S. pneumoniae R6 | E. coli SM1411 | E. faecium 11.4103A |
|---|---|---|---|---|---|
| G7N | 32, 32 | <4, <4 | 16, 16 | | 32, 64 |
| G8N | 64, 64 | 8, 8 | >64, >64 | | 64, 64 |
| G9H | 32, 32 | <4, <4 | 16, 16 | | 32, 16 |
| G9A | 32, 32 | <4, <4 | 8, 8 | | 16, 16 |
| G10V | 64, 64 | <4, <4 | 16, 16 | | >64, >64 |
| G10Y | 16, 8 | <4, <4 | <4, <4 | | 64, 64 |
| Dha16G | 16, 16 | 2, 4 | 2, 2 | | |
| V11M | 32, 16 | 16, 16 | 32, 32 | | |
| L14M | 32, 16 | 2, 2 | 4, 4 | | |
| L14V | 16, 16 | 8, 4 | 4, 4 | | |
| Dha16Dhb | 16, 16 | 1, 1 | 32, 32 | | |
| V11I | 16, 16 | .5, .5 | 16, 16 | | |
| F3W | 8.5, 8.5 | 4.25, 2.13 | 4.25, 2.13 | | |
| G9S | >64, >64 | 64, 64 | >64, >64 | | |
| G8Q | 32, 64 | 32, 64 | NYD | | |
| V11L | 16, 16 | 8, 4 | 4, 4 | | |
| Dha16A | 16, 16 | 8, 4 | 4, 4 | | |
| L14I | 16, 8 | 1, 2 | | | |
| G10A | >64, 64 | 8, 8 | | | |
| G10N | >64, >64 | 8, 8 | >64, >64 | | |
| G9R | >64, >64 | 16, 16 | >64, >64 | | |
| G9N | 64, 64 | 64, >64 | >64, >64 | | |
| P6H | 64, 32 | 16, 16 | >64, 64 | | |
| G7A | 64, 64 | 64, 64 | >64, >64 | | |
| Mersacidin | 16, 8 | | <4, <4 | >64, >64 | 16, 16 |

EXAMPLE 13

Further MIC Data

MIC tests were performed with some of the variants of Example 2 on a range of other organisms. The results are shown in Tables 9 and 10 (figures in µg/ml):

TABLE 9

| | S. pyogenes 16205 | S. aureus CS | S. pyogenes 13608 | S. aureus SG511 |
|---|---|---|---|---|
| G8A | 1 | 8 | 1 | 8 |
| P6A | 8 | 32 | 4 | 8 |
| F3W | 0.125 | 4 | 0.125 | 2 |
| Dha16H | 4 | 64 | 4 | 8 |
| Mersacidin | 0.5 | 4 | 0.25 | 2 |

| | S. aureus COL MRSA | S. aureus 1012-13 MRSA | M. luteus 4698 | E. faecium 4147 VRE | E. faecium 4147-1 |
|---|---|---|---|---|---|
| G8A | 32 | 16 | 4 | 64-16 h, 128-24 h | 128 |
| P6A | 64 | 32 | 4 | 128-16 h, 256-24 h | 256 |
| F3W | 16 | 4 | 0.5 | 32 | 32-16 h, 64-23 h |
| Dha16H | 64 | 64 | 4 | 128 | 128-16 h, 256-23 h |
| Mersacidin | 16 | 8 | 0.5 | 64 | 64 |

TABLE 10

| | S. pyogenes 16205 | S. aureus Mu50 | Streptococcus G 017882 | S. aureus SG511 | S. aureus COL | S. aureus LT 1012-13 | M. luteus 4698 | E. faecium BM4147 |
|---|---|---|---|---|---|---|---|---|
| G9A | 16, 8 | >64, >64 | 32, 32 | 8, 16 | 64, >64 | >64, >64 | 8, 8 | >64, >64 |
| G9H | 16, 8 | >64, >64 | 16, 16 | 8, 16 | >64, >64 | >64, >64 | 8, 4 | >64, >64 |
| G8N | 64, 64 | >64, >64 | 64, 64 | 32, 64 | >64, >64 | >64, >64 | 32, 32 | >64, >64 |
| P6H | 8, 8 | >64, >64 | 16, 8 | 8, 16 | >64, >64 | >64, >64 | 4, 2 | >64, >64 |
| P6N | 8, 16 | >32, >32 | 16, 8 | 8, 8 | >32, >32 | >32, >32 | 8, 4 | >32, >32 |

EXAMPLE 14

Activity of G8H.

The G8H variant was tested as described in Example 2. The MIC (in µg/ml) against eight of the Example 2 strains was as set out in Table 11:

TABLE 11

| | E. faecium 7131121 | E. faecium 19579 | E. faecalis 29212 | S. aureus R33 |
|---|---|---|---|---|
| G8H | >64, >64 | >64, >64 | >64, >64 | 64, 64 |

| | S. aureus SH1000 | S. epidermidis 11047 | M. luteus 4698 | S. pneumoniae R6 |
|---|---|---|---|---|
| G8H | 64, >64 | 64, 64 | 8, 8 | 16, 16 |

EXAMPLE 15

Activity Against Fusidic Acid Resistant Staphylococcus aureus

MICs (in µg/ml) were determined, as described in Example 2, for three variants against fusidic acid resistant strains of Staphylococcus aureus. The results are shown in Table 12:

TABLE 12

| | mersacidin | F3W | Dha16Dhb | Dha16G |
|---|---|---|---|---|
| S. aureus 8325-4 | 8, 8 | 4, 4 | 8, 8 | 16, 16 |
| S. aureus CS1116 | 4, 2 | 4, 2 | 2, 2 | 4, 4 |
| S. aureus CS957 | 8, 8 | 4, 4 | 16, 16 | 16, 16 |
| S. aureus CS767 | 16, 16 | 8, 8 | 16, 16 | 16, 16 |
| S. aureus CS858 | 16, 16 | 8, 8 | 16, 16 | 32, 16 |
| S. aureus CS741 | 8, 8 | 8, 8 | 8, 8 | 16, 16 |
| S. aureus CS1145 | 4, 4 | 4, 4 | 16, 16 | 16, 16 |
| S. aureus CS872 | 8, 8 | 4, 4 | 8, 8 | 16, 16 |
| S. aureus CS866 | 8, 8 | 4, 4 | 16, 16 | 16, 16 |
| S. aureus CS607 | 16, 16 | 8, 8 | 16, 16 | 16, 16 |
| S. aureus CS22 | 8, 8 | 4, 4 | 16, 16 | 16, 16 |

EXAMPLE 16

Activity Against Mupirocin Resistant Staphylococcus aureus

MICs were determined, as described in Example 2, for three variants against mupirocin resistant strains of Staphylococcus aureus. Results are shown in Table 13 in µg/ml:

TABLE 13

| | mersacidin | F3W | Dha16Dhb | Dha16G |
|---|---|---|---|---|
| S. aureus 8325-4 | 8, 8 | 4, 4 | 8, 8 | 16, 16 |
| S. aureus GISA-2 | 16, 16 | 4, 4 | 8, 8 | 16, 16 |
| S. aureus LZ6 | 8, 8 | 8, 8 | 16, 16 | 16, 16 |
| S. aureus LZ8 | 8, 8 | 8, 8 | 16, 16 | 16, 16 |
| S. aureus LZ9 | 16, 16 | 16, 16 | 32, 32 | 16, 16 |
| S. aureus LZ10 | 16, 16 | 16, 16 | 16, 16 | 16, 16 |
| S. aureus 420 | 8, 8 | 4, 4 | 8, 16 | 16, 16 |
| S. aureus 1205 | 16, 16 | 16, 16 | 32, 32 | 32, 32 |
| S. aureus 1120 | 16, 16 | 8, 8 | 16, 16 | 16, 16 |
| S. aureus 1454 | 8, 16 | 8, 8 | 16, 16 | 16, 16 |
| S. aureus 1086 | 16, 16 | 16, 16 | 16, 16 | 16, 16 |

EXAMPLE 17

Activity Against *Streptococcus pyogenes*

MICs were determined, as described in Example 2, for five variants against strains of *Streptococcus pyogenes*. Results are shown in Table 14 in µg/ml:

TABLE 14

|  | mersacidin | F3W | V11I | L14I | Dha16Dhb | Dha16G |
|---|---|---|---|---|---|---|
| *S. pyogenes* 7755441 | 2, 2 | 1, 1 | 2, 2 | 2, 2 | 2, 2 | 8, 8 |
| *S. pyogenes* 7713283 | 2, 1 | 1, 1 | 1, 1 | 2, 4 | 2, 2 | 8, 8 |
| *S. pyogenes* 7865844 | 2, 1 | 1, 2 | 1, 1 | 2, 2 | 2, 2 | 8, 8 |
| *S. pyogenes* 7753040 | 2, 2 | 1, 1 | 1, 1 | 2, 2 | 2, 2 | 8, 8 |
| *S. pyogenes* 7755255 | 1, 1 | 1, 1 | 1, 2 | 2, 2 | 2, 2 | 8, 8 |
| *S. pyogenes* 7756725 | 1, 1 | 0.5, 1 | 1, 1 | 1, 1 | 1, 2 | 4, 4 |
| *S. pyogenes* 7757080 | 1, 1 | 1, 1 | 0.5, 1 | 1, 2 | 2, 2 | 8, 4 |
| *S. pyogenes* GRL05045 | 1, 1 | 1, 1 | 2, 1 | 2, 2 | 2, 2 | 8, 8 |
| *S. pyogenes* 7865253 | 0.5, 1 | 0.5, 1 | 0.5, 1 | 1, 2 | 1, 2 | 4, 4 |
| *S. pyogenes* GRL05046 | 1, 2 | 0.5, 1 | 1, 2 | 1, 2 | 2, 4 | 4, 8 |

EXAMPLE 18

Activity Against Viridans *Streptococcus*

MICs, were,determined, as described in Example 2, for five variants against strains of viridans *Streptococcus*. Results are shown in Table 15 in µg/ml:

TABLE 15

|  | mersacidin | F3W | V11I | L14I | Dha16Dhb | Dha16G |
|---|---|---|---|---|---|---|
| *S. salivarius* GRL05064 | 1, 1 | 0.5, 0.5 | 1, 1 | 1, 1 | 2, 2 | 4, 8 |
| *S. mitis* 1 7722543 | 1, 2 | 1, 1 | 2, 2 | 4, 4 | 4, 4 | 8, 8 |
| *S. mitis* 1 7863547 | 2, 2 | 1, 1 | 2, 2 | 4, 4 | 2, 2 | 8, 8 |
| *Aerococcus viridans* 2 BC6008.2 | 4, 2 | 2, 2 | 4, 4 | 8, 8 | 4, 4 | 8, 16 |
| *S. oralis* 5823 | 4, 4 | 2, 4 | 4, 4 | 8, 8 | 8, 8 | 16, 16 |
| *S. salivarius* GRL05063 | 4, 8 | 1, 2 | 4, 8 | 4, 4 | 4, 4 | 8, 8 |
| *S. constellatus* GRL05065 | 8, 8 | 4, 4 | 8, 8 | 16, 16 | 16, 16 | 16, 16 |
| *S. oralis* GRL05066 | 4, 4 | 2, 2 | 2, 2 | 4, 4 | 8, 4 | 16, 8 |
| *S. oralis* GRL05069 | 32, 32 | 16, 16 | 16, 16 | 16, 16 | 32, 32 | 32, 32 |

EXAMPLE 19

Activity Against *Propionibacterium acnes*

Test organisms were selected from 3-7 day growth on Wilkens-Chalgren agar (WCA) supplemented with furazolidone (1-2 µg/ml). Fresh Wilkens-Chalgren broth (WCB) was inoculated by direct colony suspension with single colonies of *P. acnes* and adjusted to a density equivalent to the McFarland 0.5 standard ($1 \times 10^8$ CFU/ml), then further diluted in sterile WCB, supplemented with 50 µg/ml $Ca^{2+}$ (as calcium chloride dihydrate), for a final inoculum in sterile 96-well microtitre plates of approximately $10^5$ CFU/ml. Two-fold serial antibiotic dilutions were performed in sterile water with stock solutions prepared and stored according to NCCLS standards (M11-A5, 2001). The assays were performed in duplicate with Vancomycin and Clindamycin used as reference antibiotics for quality control. Plates were incubated anaerobically for 48-72 hours at 37° C. with the MIC defined as the concentration of drug where a marked reduction occurred in the appearance of growth on the test plate compared to growth on the control plate. All manipulations were performed in duplicate in ambient atmosphere in pre-reduced media with only brief exposure to air.

MICs (in µg/ml) of three variants against strains of *P. acnes* was as shown in Table 16:

TABLE 16

|  | mersacidin | F3W | Dha16Dhb | Dha16G |
|---|---|---|---|---|
| *P. acnes* P37 | 2, 2 | 1, 1 | 4, 8 | 4, 4 |
| *P. acnes* AT1 | 2, 2 | 1, 1 | 4, 4 | 4, 4 |

TABLE 16-continued

|  | mersacidin | F3W | Dha16Dhb | Dha16G |
|---|---|---|---|---|
| *P. acnes* AT26 | 2, 2 | 1, 1 | 2, 2 | 2, 2 |
| *P. acnes* 101897d | 2, 2 | 1, 0.5 | 2, 2 | 1, 1 |
| *P. acnes* PF284 | 2, 2 | 1, 1 | 2, 2 | 2, 2 |
| *P. acnes* PF286 | 2, 2 | 1, 1 | 2, 2 | 2, 2 |
| *P. acnes* PF289 | 2, 2 | 1, 2 | 8, 8 | 4, 4 |
| *P. acnes* PF290 | 4, 2 | 0.5, 1 | 1, 2 | 2, 2 |
| *P. acnes* PF291 | 4, 2 | 0.5, 0.5 | 0.5, 1 | 2, 2 |
| *P. acnes* 1348 | 2, 2 | 2, 2 | 4, 4 | 8, 8 |
| *P. acnes* 1431 | 4, 4 | 2, 2 | 4, 4 | 2, 2 |

EXAMPLE 20

Activity Against *Clostridium difficile*

Minimum inhibitory concentrations (MICs) for *C. difficile* were determined and antimicrobial agent stock solutions were prepared and stored according to the NCCLS reference agar dilution method for anaerobic bacteria (M11-A5, 2001). Two-fold serial antibiotic dilutions were prepared in Wilkens-Chalgren agar (WCA). Test organisms were selected from 48 hour growth on Braziers (C.C.E.Y.) agar, subcultured in Schaedler broth to a density equivalent to a McFarland 0.5 standard ($1\times10^8$ CFU/ml), with a final inoculum onto WCA plates supplemented with 50 μg/ml $Ca^{2+}$ (as calcium chloride dehydrate) of approximately $10^5$ CFU/spot. *Bacteroides fragilis* ATCC 25285 was included as a reference control strain and Metronidazole was used as a reference antibiotic for quality control. All manipulations were performed in duplicate in ambient atmosphere in pre-reduced media with only brief exposure to air. Plates were incubated anaerobically for 48 hours at 37° C. with the MIC defined as the concentration of drug where a marked reduction occurred in the appearance of growth on the test plate compared to growth on the control plate.

MICs of the F3W and F3W-L14I variants are shown in Table 17 in μg/ml:

TABLE 17

|  | mersacidin | F3W | F3W-L14I |
|---|---|---|---|
| *C. difficile* ATCC 43594 | 2, 4 | 2, 2 | 2, 2 |
| *C. difficile* ATCC 43255 | 2, 4 | 2, 2 | 2, 2 |

EXAMPLE 21

Activity of Double Variants

MICs of double variants were determined as in Example 2 against eight of the example 2 strains. The MICs are shown in Table 18 in μg/ml:

TABLE 18

|  | *E. faecium* 7131121 | *E. faecium* 19579 | *E. faecalis* 29212 | *S. aureus* R33 |
|---|---|---|---|---|
| L14I Dha16G | 32, 32 | 32, 32 | 16, 8 | 8, 8 |
| L14I Dha16Dhb | >64, >64 | 32, 64 | >64, >64 | 8, 8 |
| V11I Dha16G | 64, 64 | 32, 32 | 64, 64 | 16, 16 |
| F3W L14I | 8, 8 | 8, 8 | 8, 8 | 2, 2 |
| V11I L14I | 16, 16 | 16, 8 | 8, 16 | 4, 4 |

|  | *S. aureus* SH1000 | *S. epidermidis* 11047 | *M. luteus* 4698 | *S. pneumoniae* R6 |
|---|---|---|---|---|
| L14I Dha16G | 16, 32 | 16, 16 | 16, 8 | 32, 32 |
| L14I Dha16Dhb | 32, 64 | 32, 64 | 1, 1 | 4, 4 |
| V11I Dha16G | 32, 32 | 32, 32 | 0.5, 0.5 | 4, 4 |
| F3W L14I | 8, 8 | 4, 4 | 0.125, 0.125 | 0.5, 0.25 |
| V11I L14I | 16, 16 | 4, 8 | 0.25, 0.25 | 0.5, 0.5 |

REFERENCES

Altena et, al., Appl. Env. Microbiol. 66, 2565-2571; 2000
Bierbaum et al. (1995) FEMS Microbiol. Lett. 127, 121-126
Britton et al. J Bacteriol. 184, 4881-90; 2002.
Guder et al. Applied and Environmental Microbiology 68, 106-113; 2002
Lonetto et al. J. Bacteriol. 174, 3843-3849; 1992
Marahiel et al. Mol. Microbiol. 7, 631-636; 1993
O'Sullivan, D. J. and Klaenhammer, T. R. (1993) Gene, 137: 227-231.
Szekat et al. (2003) Appl. Env. Microbiol. 69, 3777-3783
Sequences:
The present application includes reference to the following sequences:
SEQ ID NO:1
MrsA gene sequence of the MrsA encoding sequence including the leader sequence and the propeptide region. The propeptide encoding region is shown underlined:

```
      atgagtca agaagctatc attcgttcat ggaaagatcc tttttcccgt gaaaattcta
 5161 cacaaatcc agctggtaac ccattcagtg agctgaaaga agcacaaatg gataagttag
 5221 taggtgcggg agacatggaa gcagcatgta cttttacatt gcctggtggc ggcggtgttt
 5281 gtactctaac ttctgaatgt atttgttaa
```

SEQ ID NO:2—Translation of SEQ ID NO:1. The propeptide region is underlined.

MSQEAIIRSWKDPFSRENSTQNPAGNPFSELKEAQMDKLVGAGDMEAA<u>CT
FTLPGGGGVCTLTSECIC</u>

Further sequences (SEQ ID NO:3 to SEQ ID NO:43) are set out in the description.

The invention claimed is:

1. A mersacidin variant, or a pharmaceutically acceptable salt thereof, wherein the variant is mersacidin F3W of the structure (SEQ ID NO:45)

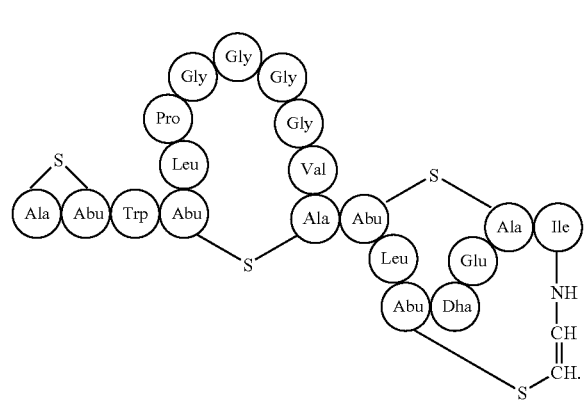

2. A mersacidin variant of SEQ ID NO:45, or a pharmaceutically acceptable salt thereof, wherein the variant differs by one amino acid substitution at one of position 5, 6, 7, 8, 9, 10, 11, 14 or 16 set out in the following Table

TABLE 1

| L5  | P6  | G7  | G8  | G9  | G10  | V11  | L14  | Dha16    |
|-----|-----|-----|-----|-----|------|------|------|----------|
| L5A | P6H | G7A | G8A | G9A | G10A | V11L | L14V | Dha16G   |
| L5I | P6F | G7N | G8N | G9S | G10V | V11I | L14I | Dha16A   |
| L5M |     | G7S | G8Q | G9T | G10S | V11M |      | Dha16Dhb |
| L5H |     | G7T | G8H | G9N | G10M | V11K |      | Dha16H   |
|     |     | G7H | G8E | G9R | G10Y |      |      |          |
|     |     |     | G8P | G9Y | G10R |      |      |          |
|     |     |     |     | G9H | G10K |      |      |          |
|     |     |     |     | G9Q | G10H |      |      |          |
|     |     |     |     | G9L | G10N.|      |      |          |

3. The variant of claim 2 selected from the group consisting of G9A, G9H, V11I, V11L, L14I, L14V, Dha16G and Dha16Dhb.

4. A composition comprising a mersacidin variant according to claim 1 together with a pharmaceutically acceptable carrier.

5. A composition according to claim 4 wherein said carrier is in the form of an aqueous, aqueous-alcoholic or oily solution, an oil-in-water or water-in-oil or multiple emulsion, an aqueous or oily gel, a liquid, pasty or solid anhydrous product suitable for topical administration.

6. A method of treatment of a bacterial infection in a human or animal subject which comprises administering to said subject the mersacidin variant of claim 1.

7. The method of claim 6, wherein said treatment is selected from: treatment of systemic bacterial infections; systemic treatment of bacteraemia; treatment of pneumonia; treatment of skin and skin structure infections; treatment of endocarditis, treatment of osteomyelitis; treatment of acne; treatment of an eye infection; treatment of a gut super-infection; treatment of infection of the skin in wounds or burns.

8. The method of claim 6, wherein said treatment of the human or animal body is of a bacterial infection selected from an infection caused by one of *Clostridium difficile, Streptococcus* spp, *Enterococcus* spp., *Staphylococcus* spp., *Propionibacterium acnes*, and *Helicobacter pylori*.

9. The method of claim 8 wherein said *Staphylococcus spp.* are coagulase-negative staphylococci, or said *Staphylococcus* spp. is *S. aureus* or a drug-resistant species selected from the group consisting of MRSA, VISA, VRSA, GISA, LRSA, and mupirocin-resistant *Staph. aureus*.

10. The method of claim 8 wherein said *Streptococcus* spp. are selected from the group consisting of *Streptococcus pyogenes, Streptococcus agalactiae*, and *Streptococcus pneumoniae*.

11. The method of claim 8 wherein said *Enterococcus* spp is *E. faecium* or *E. faecalis*.

12. The method of claim 9 wherein said *Staphylococcus* spp. is coagulase-negative *Staphylococcus epidermidis*.

* * * * *

SEQUENCE LISTING

<160> NUMBER OF SEQ ID NOS: 43

<210> SEQ ID NO 1

```
<211> LENGTH: 207
<212> TYPE: DNA
<213> ORGANISM: Bacillus sp. HIL Y-85,54728

<400> SEQUENCE: 1
atgagtcaag aagctatcat tcgttcatgg aaagatcctt tttcccgtga aaattctaca      60
caaaatccag ctggtaaccc attcagtgag ctgaaagaag cacaaatgga taagttagta     120
ggtgcgggag acatggaagc agcatgtact tttacattgc ctggtggcgg cggtgttttgt    180 actctaactt ctgaatgtat ttgttaa                                         207

<210> SEQ ID NO 2
<211> LENGTH: 68
<212> TYPE: PRT
<213> ORGANISM: Bacillus sp. HIL Y-85,54728

<400> SEQUENCE: 2

Met Ser Gln Glu Ala Ile Ile Arg Ser Trp Lys Asp Pro Phe Ser Arg
1               5                   10                  15

Glu Asn Ser Thr Gln Asn Pro Ala Gly Asn Pro Phe Ser Glu Leu Lys
            20                  25                  30

Glu Ala Gln Met Asp Lys Leu Val Gly Ala Gly Asp Met Glu Ala Ala
        35                  40                  45

Cys Thr Phe Thr Leu Pro Gly Gly Gly Gly Val Cys Thr Leu Thr Ser
    50                  55                  60

Glu Cys Ile Cys
65

<210> SEQ ID NO 3
<211> LENGTH: 31
<212> TYPE: DNA
<213> ORGANISM: Artificial sequence
<220> FEATURE:
<223> OTHER INFORMATION: Primer SigmaH5prime

<400> SEQUENCE: 3
tatggtacca tagggggcgca cagagaggat a                                    31

<210> SEQ ID NO 4
<211> LENGTH: 29
<212> TYPE: DNA
<213> ORGANISM: Artificial sequence
<220> FEATURE:
<223> OTHER INFORMATION: Primer SigmaH3prime

<400> SEQUENCE: 4
ctttctagat ctcccatttt catttcaat                                        29

<210> SEQ ID NO 5
<211> LENGTH: 18
<212> TYPE: DNA
<213> ORGANISM: Artificial sequence
<220> FEATURE:
<223> OTHER INFORMATION: Primer SigH1

<400> SEQUENCE: 5
gtgaatctac agaacaac                                                    18

<210> SEQ ID NO 6
<211> LENGTH: 18
<212> TYPE: DNA
<213> ORGANISM: Artificial sequence
<220> FEATURE:
<223> OTHER INFORMATION: Primer SigH2
```

```
<400> SEQUENCE: 6
gtacttctcc agcttgcg                                                18

<210> SEQ ID NO 7
<211> LENGTH: 22
<212> TYPE: DNA
<213> ORGANISM: Artificial sequence
<220> FEATURE:
<223> OTHER INFORMATION: Primer pTV0Ins-1

<400> SEQUENCE: 7
gatttacata tgagttatgc ag                                           22

<210> SEQ ID NO 8
<211> LENGTH: 20
<212> TYPE: DNA
<213> ORGANISM: Artificial sequence
<220> FEATURE:
<223> OTHER INFORMATION: Primer pTV0Ins-2

<400> SEQUENCE: 8
ctactataac tggtactcgc                                              20

<210> SEQ ID NO 9
<211> LENGTH: 30
<212> TYPE: DNA
<213> ORGANISM: Artificial sequence
<220> FEATURE:
<223> OTHER INFORMATION: Oligonucleotide yacPEcoRI

<400> SEQUENCE: 9
aatgaattcc aggaaacagg gttattgttg                                   30

<210> SEQ ID NO 10
<211> LENGTH: 32
<212> TYPE: DNA
<213> ORGANISM: Artificial sequence
<220> FEATURE:
<223> OTHER INFORMATION: Oligonucleotide yacPHindIII

<400> SEQUENCE: 10
tccaagcttc ctattaagaa ataggatctt gc                                32

<210> SEQ ID NO 11
<211> LENGTH: 32
<212> TYPE: DNA
<213> ORGANISM: Artificial sequence
<220> FEATURE:
<223> OTHER INFORMATION: Oligonucleotide rpmGHindIII

<400> SEQUENCE: 11
gacaagctta gttaccaaga gatttctgat ga                                32

<210> SEQ ID NO 12
<211> LENGTH: 28
<212> TYPE: DNA
<213> ORGANISM: Artificial sequence
<220> FEATURE:
<223> OTHER INFORMATION: Oligonucleotide rpmGEcoRV

<400> SEQUENCE: 12
atagatatcc cgctgaacgg gttttggc                                     28

<210> SEQ ID NO 13
<211> LENGTH: 28
```

```
<212> TYPE: DNA
<213> ORGANISM: Artificial sequence
<220> FEATURE:
<223> OTHER INFORMATION: Oligonucleotide jc7

<400> SEQUENCE: 13
cttatgagaa ttcgagacaa ggtaaact                                        28

<210> SEQ ID NO 14
<211> LENGTH: 31
<212> TYPE: DNA
<213> ORGANISM: Artificial sequence
<220> FEATURE:
<223> OTHER INFORMATION: Oligonucleotide jc8

<400> SEQUENCE: 14
gcatgctgct tccatgtctc ccgcacctac t                                    31

<210> SEQ ID NO 15
<211> LENGTH: 60
<212> TYPE: DNA
<213> ORGANISM: Artificial sequence
<220> FEATURE:
<223> OTHER INFORMATION: Oligonucleotide jc9

<400> SEQUENCE: 15
cacttttaca ttgcctggtg gcggcggtgt ttgtacacta acttctgaat gtatttgtta     60

<210> SEQ ID NO 16
<211> LENGTH: 68
<212> TYPE: DNA
<213> ORGANISM: Artificial sequence
<220> FEATURE:
<223> OTHER INFORMATION: Oligonucleotide jc10

<400> SEQUENCE: 16
agcttaacaa atacattcag aagttagtgt acaaacaccg ccgccaccag gcaatgtaaa     60
agtgcatg                                                              68

<210> SEQ ID NO 17
<211> LENGTH: 32
<212> TYPE: DNA
<213> ORGANISM: Artificial sequence
<220> FEATURE:
<223> OTHER INFORMATION: Degenerate oligonucleotide jc27

<400> SEQUENCE: 17
cacttttaca dtgcctgbtg bcgbcgbtgb tt                                   32

<210> SEQ ID NO 18
<211> LENGTH: 40
<212> TYPE: DNA
<213> ORGANISM: Artificial sequence
<220> FEATURE:
<223> OTHER INFORMATION: Degenerate oligonucleotide jc28

<400> SEQUENCE: 18
gtacaavcav cgvcgvcavc aggcahtgta aaagtgcatg                           40

<210> SEQ ID NO 19
<211> LENGTH: 27
<212> TYPE: DNA
<213> ORGANISM: Artificial sequence
<220> FEATURE:
<223> OTHER INFORMATION: Oligonucleotide jc36

<400> SEQUENCE: 19
```
aagcttgatt tatataggct gtttccc                                    27

<210> SEQ ID NO 20
<211> LENGTH: 24
<212> TYPE: DNA
<213> ORGANISM: Artificial sequence
<220> FEATURE:
<223> OTHER INFORMATION: Oligonucleotide jc37

<400> SEQUENCE: 20
gtgtacgtaa agacttgacc tacc                                       24

<210> SEQ ID NO 21
<211> LENGTH: 28
<212> TYPE: DNA
<213> ORGANISM: Artificial sequence
<220> FEATURE:
<223> OTHER INFORMATION: Oligonucleotide jc32

<400> SEQUENCE: 21
ctttacgtac acattagttc tcttagag                                   28

<210> SEQ ID NO 22
<211> LENGTH: 38
<212> TYPE: DNA
<213> ORGANISM: Artificial sequence
<220> FEATURE:
<223> OTHER INFORMATION: Oligonucleotide jc33

<400> SEQUENCE: 22
ggaagcggaa gagctttaaa gaaagaacaa aacacccc                        38

<210> SEQ ID NO 23
<211> LENGTH: 32
<212> TYPE: DNA
<213> ORGANISM: Artificial sequence
<220> FEATURE:
<223> OTHER INFORMATION: Degenerate oligonucleotide jc15

<400> SEQUENCE: 23
cacttttaca ttgcctggtg ycggcggtgt tt                              32

<210> SEQ ID NO 24
<211> LENGTH: 40
<212> TYPE: DNA
<213> ORGANISM: Artificial sequence
<220> FEATURE:
<223> OTHER INFORMATION: Degenerate oligonucleotide jc16

<400> SEQUENCE: 24
gtacaaacac cgccgrcacc aggcaatgta aaagtgcatg                      40

<210> SEQ ID NO 25
<211> LENGTH: 32
<212> TYPE: DNA
<213> ORGANISM: Artificial sequence
<220> FEATURE:
<223> OTHER INFORMATION: Oligonucleotide O/SB34F

<400> SEQUENCE: 25
cacttggaca ttgcctggtg gcggcggtgt tt                              32

<210> SEQ ID NO 26
<211> LENGTH: 40
<212> TYPE: DNA
<213> ORGANISM: Artificial sequence

```
<220> FEATURE:
<223> OTHER INFORMATION: Oligonucleotide O/SB35R

<400> SEQUENCE: 26
gtacaaacac cgccgccacc aggcaatgtc caagtgcatg                          40

<210> SEQ ID NO 27
<211> LENGTH: 37
<212> TYPE: DNA
<213> ORGANISM: Artificial sequence
<220> FEATURE:
<223> OTHER INFORMATION: Primer 5primemrsAR1

<400> SEQUENCE: 27
agaaatatga attcatctta agactctttta tttaaac                            37

<210> SEQ ID NO 28
<211> LENGTH: 23
<212> TYPE: DNA
<213> ORGANISM: Artificial sequence
<220> FEATURE:
<223> OTHER INFORMATION: Primer 3primemrsAR1

<400> SEQUENCE: 28
ttgggtcaag cttttacac gac                                             23

<210> SEQ ID NO 29
<211> LENGTH: 28
<212> TYPE: DNA
<213> ORGANISM: Artificial sequence
<220> FEATURE:
<223> OTHER INFORMATION: Primer E17A Mut

<400> SEQUENCE: 29
ctatataaat caaattaaca aatacatg                                       28

<210> SEQ ID NO 30
<211> LENGTH: 28
<212> TYPE: DNA
<213> ORGANISM: Artificial sequence
<220> FEATURE:
<223> OTHER INFORMATION: Primer E17A Umut

<400> SEQUENCE: 30
ctatataaat caaattaaca aatacatt                                       28

<210> SEQ ID NO 31
<211> LENGTH: 24
<212> TYPE: DNA
<213> ORGANISM: Artificial sequence
<220> FEATURE:
<223> OTHER INFORMATION: Primer primer5prime

<400> SEQUENCE: 31
gggtatatgc ggtataaact tatg                                           24

<210> SEQ ID NO 32
<211> LENGTH: 22
<212> TYPE: DNA
<213> ORGANISM: Artificial sequence
<220> FEATURE:
<223> OTHER INFORMATION: Primer pTV0Ins-1

<400> SEQUENCE: 32
gatttacata tgagttatgc ag                                             22
```

```
<210> SEQ ID NO 33
<211> LENGTH: 21
<212> TYPE: DNA
<213> ORGANISM: Artificial sequence
<220> FEATURE:
<223> OTHER INFORMATION: Primer pTV0Ins-2

<400> SEQUENCE: 33
actactataa ctggtactcg c                                              21

<210> SEQ ID NO 34
<211> LENGTH: 24
<212> TYPE: DNA
<213> ORGANISM: Artificial sequence
<220> FEATURE:
<223> OTHER INFORMATION: Primer primer5prime

<400> SEQUENCE: 34
gggtatatgc ggtataaact tatg                                           24

<210> SEQ ID NO 35
<211> LENGTH: 20
<212> TYPE: DNA
<213> ORGANISM: Artificial sequence
<220> FEATURE:
<223> OTHER INFORMATION: Primer 3prime mrsD

<400> SEQUENCE: 35
aagaacaaaa cacccctcac                                                20

<210> SEQ ID NO 36
<211> LENGTH: 32
<212> TYPE: DNA
<213> ORGANISM: Artificial sequence
<220> FEATURE:
<223> OTHER INFORMATION: Mutagenic oligonucleotide

<400> SEQUENCE: 36
gaatacaatg agtcaataag ctatcattcg tt                                  32

<210> SEQ ID NO 37
<211> LENGTH: 23
<212> TYPE: DNA
<213> ORGANISM: Artificial sequence
<220> FEATURE:
<223> OTHER INFORMATION: Primer pIN1HIN

<400> SEQUENCE: 37
ggcgaattcg agacaaggta aac                                            23

<210> SEQ ID NO 38
<211> LENGTH: 33
<212> TYPE: DNA
<213> ORGANISM: Artificial sequence
<220> FEATURE:
<223> OTHER INFORMATION: Primer pIN1RUCK

<400> SEQUENCE: 38
tttctgcaga gaattttcta atagtttata taa                                 33

<210> SEQ ID NO 39
<211> LENGTH: 27
<212> TYPE: DNA
<213> ORGANISM: Artificial sequence
<220> FEATURE:
<223> OTHER INFORMATION: Primer pBT2reverse

<400> SEQUENCE: 39
```

```
cctgactgcg ttagcaattt aactgtg                                        27

<210> SEQ ID NO 40
<211> LENGTH: 24
<212> TYPE: DNA
<213> ORGANISM: Artificial sequence
<220> FEATURE:
<223> OTHER INFORMATION: Primer 5prime

<400> SEQUENCE: 40
gggtatatgc ggtataaact tatg                                           24

<210> SEQ ID NO 41
<211> LENGTH: 22
<212> TYPE: DNA
<213> ORGANISM: Artificial sequence
<220> FEATURE:
<223> OTHER INFORMATION: Primer MutE4stop

<400> SEQUENCE: 41
ggggtgaata caatgagtca at                                             22

<210> SEQ ID NO 42
<211> LENGTH: 22
<212> TYPE: DNA
<213> ORGANISM: Artificial sequence
<220> FEATURE:
<223> OTHER INFORMATION: Primer UmutE4stop

<400> SEQUENCE: 42
ggggtgaata caatgagtca ag                                             22

<210> SEQ ID NO 43
<211> LENGTH: 30
<212> TYPE: DNA
<213> ORGANISM: Artificial sequence
<220> FEATURE:
<223> OTHER INFORMATION: Primer RT5

<400> SEQUENCE: 43
attaacaaat acattcagaa gttagagtac                                     30
```